US 7,696,161 B2
Apr. 13, 2010

(12) United States Patent
Beeley et al.

(10) Patent No.: US 7,696,161 B2
(45) Date of Patent: *Apr. 13, 2010

(54) EXENDIN AGONIST COMPOUNDS

(75) Inventors: Nigel Robert Arnold Beeley, San Diego, CA (US); Kathryn S. Prickett, Hillsborough, CA (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 102 days.

This patent is subject to a terminal disclaimer.

(21) Appl. No.: 11/807,031

(22) Filed: May 25, 2007

(65) Prior Publication Data
US 2008/0119393 A1 May 22, 2008

Related U.S. Application Data

(63) Continuation of application No. 09/554,533, filed as application No. PCT/US98/24210 on Nov. 13, 1998, now Pat. No. 7,223,725.

(60) Provisional application No. 60/065,442, filed on Nov. 14, 1997.

(51) Int. Cl.
A61K 38/28 (2006.01)
A61K 38/30 (2006.01)
A61K 38/00 (2006.01)

(52) U.S. Cl. .......................... 514/3; 530/303; 530/300; 530/363; 424/278.1

(58) Field of Classification Search ........................ None
See application file for complete search history.

(56) References Cited

U.S. PATENT DOCUMENTS

| 5,118,666 | A | 6/1992 | Habener |
| 5,120,712 | A | 6/1992 | Habener |
| 5,424,286 | A | 6/1995 | Eng |
| 5,512,549 | A | 4/1996 | Chen |
| 5,545,618 | A | 8/1996 | Buckley |
| 5,574,008 | A | 11/1996 | Johnson |
| 5,686,511 | A | 11/1997 | Bobo |
| 5,705,483 | A | 1/1998 | Galloway et al. |
| 5,846,937 | A | 12/1998 | Drucker |
| 6,191,102 | B1 | 2/2001 | DiMarchi et al. |
| 6,399,601 | B1 | 6/2002 | Du Bois |
| 6,506,724 | B1 | 1/2003 | Hiles et al. |
| 6,767,887 | B1 * | 7/2004 | Hoffmann et al. ............... 514/2 |
| 6,956,026 | B2 | 10/2005 | Beeley et al. |
| 7,220,721 | B1 * | 5/2007 | Beeley et al. .................. 514/12 |
| 7,223,725 | B1 * | 5/2007 | Beeley et al. .................. 514/2 |

FOREIGN PATENT DOCUMENTS

| WO | WO 9011296 | 10/1990 |
| WO | WO 9111457 | 8/1991 |
| WO | WO 9318786 | 9/1993 |
| WO | WO 9325579 | 12/1993 |
| WO | WO 9805351 | 2/1998 |
| WO | WO 9819698 | 5/1998 |
| WO | WO 9830231 | 7/1998 |
| WO | WO 9907404 | 2/1999 |

OTHER PUBLICATIONS

WebMD (2008, updated) "Hyperglycemia and Diabetes"http://diabetes.webmd.com/diabetes-hyperglycemia, pp. 1-2.*
Buchanan et al. (2005) Gestational diabetes mellitus, J. Clin. Invest., vol. 115, No. 3, pp. 485-491.*
Fibromyalgia Symptoms (2009, updated ) Fibromyalgia Associated Conditions: Hypoglycemia, http://www.fibromyalgia-symptoms.org/fibromyalgia-hypoglycemia.html, pp. 1-3.*
Byrne et al., Diabet. Med. 13(1):854-860 (1996).
Conn & Stumpf, Outlines in Biochemistry, Third Edition, John Wiley & Sons, pp. 69-74 (1972).
Dupre et al, Diabetes, 44:626-630 (1995).
Gutniak et al, The New England Journal of Medicine, 326:1316-1322 (1992).
Harris, Gut, Supplement 3, pp. S1-S4 (1994).
Hunt et al, British Medical Journal, 4(5576):386-387 (1967).
Nauk, Diabetic Medicine, 13:S39-S43 (1996).
Neidigh et al, Biochemistry, 40(44):13188-13200 (2001).
EPO Communication of Notice of Opposition and Opposition to European Patent No. 1 019 077 by Strawman Limited (EPO Communication dated Sep. 5, 2008).
The Bachem internet website, (product No. U-1160, downloaded Dec. 13, 2007).
Chen et al, The Journal of Biological Chemistry, 272(7):4108-4115 (Feb. 14, 1997).
Nielsen et al, Current Opinion in Investigational Drugs, 4(4):401-405 (2003).
Nielsen et al, Regulatory Peptides, 117:77-88 (2004).
Adelhorst, K., et al., "Structure-activity Studies of Glucagon-like Peptide-1 (GLP-1)," J. Biol. Chem. 269 (9):6275-8 (1994).
Bartlett, et al., "Inhibition of Chymotrypsin by Phosphonate and Phosphonamidate Peptide Analogs," Bioorg. Chem., 14:356-377 (1986).
Bhavsar, "Inhibition of Gastric Emptying and of Food Intake Appear to Be Independently Controlled in Rodents," Soc. Neurosci. Abst., 21:460 (188.8)(1995).
Cohen, et al.. The Pico Tag Method: A Manual of Advanced Techniques for Amino Acid Analysis, pp. 11-52, Millipore Corporation (1989).
D'Alessio, et al., "Elimination of the Action of Glucagon-like Peptide 1 Causes an Impairment of Glucose Tolerance after Nutrient Ingestion by Healthy Baboons." J. Clin. Invest., 97:133-38 (1996).
Eissele, et al., "Rat Gastric Somatostatin and Gastrin Release: Interactions of Exendin-4 and Truncated Glucagon-Like Peptide-1 (GLP-1) Amide." Life Sci., 55:629-34(1994).

(Continued)

Primary Examiner—Anand U Desai
Assistant Examiner—Samuel Liu

(57) ABSTRACT

Novel exendin agonist compounds are provided. These compounds are useful in treating diabetes and conditions which would be benefited by lowering plasma glucose or delaying and/or slowing gastric emptying.

48 Claims, 9 Drawing Sheets

OTHER PUBLICATIONS

Eng, et al., "Isolation and Characterization of Exendin-4, an Exendin-3 Analogue, from *Heloderma suspectum* Venom." J. Biol. Chem., 267:7402-05 (1992).

Eng, et al., "Purification and Structure of Exendin-3, a New Pancreatic Secretogogue Isolated from *Heloderma horridum* Venom," J. Biol. Chem. 265:20259-62 (1990).

Fehmann, et al., "Stable Expression of the Rat GLP-1 Receptor in CHO Cells:Activation and Binding Characteristics Utilizing GLP-l(7-36)-Amide, Oxyntomodulin, Exendin-4, and Exendin(9-39)," Peptides, 15(3):453-6 (1994).

Ferguson, et al., "Cell-Surface Anchoring of Proteins Via Glvcosvlphosphatidvlinositol Structures." Annu. Rev. Biochem.. 57:285-320 (1988).

Goke, et al., "Exendin-4 Is a High Potency Agonist and Truncated Exendin-(9-39)-amide an Antagonist at the Glucagon-like Peptide l-(7-36)-amide Receptor of Insulin-secreting β-Cells," J. Biol. Chem., 268:19650-55 (1993).

Goldstone, et al., "Leptin Interacts with Glucagon-like Peptide-1 Neurons to Reduce Food Intake and Body Weight in Rodents." FEBS Letters. 415:134-138 (1997).

Halaas, J.L., et al., "Weight-Reducing Effects of the Plasma Protein Encoded by the Obese Gene." Science, 269:543-546 (1995).

Kodama, J., et al., "Effect of Captopril on Glucose Concentration Possible Role of Augmented Postprandial Forearm Blood Flow." Diabetes Care. 13(11): 1109-1111 (1990).

Kolligs, et al., "Reduction of the Incretin Effect in Rats by the Glucagon-like Peptide-1 Receptor Antagonist Exendin (9-39) Amide." Diabetes. 44:16-19 (1995).

Leibel, R.L., et al., "Changes in Energy Expenditure Resulting from Altered Body Weight." New England Journal of Medicine. 332(10):621-628 (1995).

Lithell, et al., "Insulin Sensitivity in Newly Detected Hypertensive Patients: Influence of Captopril and Other Antihypertensive Agents on Insulin Sensitivity and Related Biological Parameters." J. Cardiovasc. Pharmacol.. 15 (Supp 5):S46-S52 (1990).

Malhotra, et al., "Exendin-4, a New Peptide from *Heloderma suspectum* Venom, Potentiates Cholecystokinin-induced Amylase Release from Rat Pancreatic Acini." Regulatory Peptides, 41:149-56 (1992).

Montrose-Rafizadeh, et al., "Structure-function Analysis of Exendin-4/GLP-1 Analoes." Diabetes, 45 (Suppl. 2):152A (1996).

Navarro, M. et al., "Colocalization of Glucagon-Like Peptide-1 (GLP-1)Receptors, Glucose Transporter GLUT-2, and Glucokinase mRNAs in Rat Hypothalamic Cells: Evidence for a Role of GLP-1 Receptor Agonists as an Inhibitory Signal for Food and Water Intake," Jounral of Neurochemistry, 67: 1982-1991 (1996).

O'Halloran, et al., "Glucagon-like Peptide-1 (7-36)-NH2: a Physiological Inhibitor of Gastric Acid Secretion in Man." J. Endocrinol.. 126(I):169-73 (1990).

Ørskov, et al., "Biological Effects and Metabolic Rates of Glucagon-like Peptide-1 7-36 Amide and Glucagonlike Peptide-1 7-37 in Healthy Subjects Are Indistinguishable." Diabetes. 42:658-61 (1993).

Peeters, et al. (1983) Proline-rich polypeptides bound to rat prostate binding protein. The primary structure of the two main components, proline-rich polypeptides IV and V. J. Biol. Chem. 258, No. 23,14206-14211.

Pelleymounter, et al., "Effects of the Obese Gene Product on Body Weight Regulation in ob/ob Mice." Science. 269:540-543 (1995).

Raufman, et al., "Truncated Glucagon-like Peptide-1 Interacts with Exendin Receptors in Dispersed Acini from Guinea Pig Pancreas." J. Biol. Chem. 267:21432-37(1992).

Raufman, et al., "Exendin-3, a Novel Peptide from *Heloderma horridum* Venom, Interacts with Vasoactive Intestinal Peptide Receptors and a Newly Described Receptor on Dispersed Acini from Guinea Pig Pancreas." J. Biol. Chem., 266:2897-902 (1991).

Schepp, et al., "Exendin-4 and exendin-(9-39)NH2: Agonist and Antagonist, Respectively, at the Rat Parietal Cell Receptor for Glucagon-like Peptide-1-(7-36)NH," Eur. J. Pharm., 269:183-91 (1994).

Schjoldager, et al., "GLP-1 (Glucagon-like Peptide 1) and Truncated GLP- 1, Fragments of Human Proglucagon, Inhibit Gastric Acid Secretion in Humans," Die. Dis. Sci., 34 (5):703-8 (1989).

Singh, et al., "Use of 125I-[Y39] Exendin-4 to Characterize Exendin Receptors on Dispersed Pancreatic Acini and Gastric Chief Cells from Guinea Pig." Regul.Pept., 53:47-59 (1994).

Thorens, "Expression Cloning of the Pancreatic B Cell Receptor for the Gluco-Incretin Hormone Glucagon-like Peptide 1." Proc. Natl. Acad. Sci. USA. 89:8641-45 (1992).

Thorens, et al., "Cloning and Functional Expression of the Human Islet GLP-1 Receptor." Diabetes. 42 (11):1678-82 (1993).

Turton, et al., "A Role for Glucagon-Like Peptide-1 in the Central Regulation of Feeding," Nature. 379:69-72 (1996).

Veale, P.R., et al., The Presence of Islet Amyloid Polypeptide/Calcitonin Gen-Related Peptide/Salmon Calcitonin Binding Sites in the Rat Nucleus, Eur. J. Pharmacol., 262, 133-141 (1994).

Wang, et al., "Glucagon-like Peptide-1 Is a Physiological Incretin in Rat," J. Clin. Invest., 95:417-21 (1995).

Watson, N., et al., "Effects of Captopril on Glucose Tolerance in Elderly Patients with Congestive Cardiac Failure," Current Medical Research and Opinion. 12(6):374-378 (1991).

Wettergren, et al., "Truncated GLP-1 (Proglucagon 78-107-Amide) Inhibits Gastric and Pancreatic Functions in Man." Dig. Pis. Sci., 38(4):665-73 (1993).

Willms, et al., "Gastric Emptying, Glucose Responses, and Insulin Secretion after a Liquid Test Mel: Effects of Exogenous Glucagon-Like Peptide-1 (GLP-1)-(7-36) Amide in Type 2 (Noninsulin-Dependent) Diabetic Patients," J. Clin. Endocrinol. Metab., 81(I):327-32 (1996).

Young, et al.. Program and Abstracts. IP International Congress of Endocrinology Jun. 12-15, 1996. San Francisco, p. 419 (P2-58).

Notice of Opposition to EP 1 066 314 filed Sep. 2008 (13 pages).

Notice of Opposition to EP 1 032 587 filed Oct. 2008 (18 pages).

Alcantara et al, Archives of Biochemistry and Biophysics, 341(1):1-7 (1997)).

Ashkenazi et al, PNAS USA, 87:7150-7154 (1990).

Copley et al, Current Drug Metabolism, 7:1-8 (2006).

Cunningham, Science, 244:1081-1085 (1989).

Gibbs et al., The Journal of Biological Chemistry, 266 (14):8923-8931 (1991).

Nauck et al., J. Clin. Invest. 91:310-307 (1993).

Weir, J. Clin. Invest., 95:1 (1995).

* cited by examiner

EXENDIN-3

His Ser Asp Gly Thr Phe Thr Ser Asp Leu Ser Lys Gln Met Glu Glu
1              5                  10                 15
Glu Ala Val Arg Leu Phe Ile Glu Trp Leu Lys Asn Gly Gly Pro Ser
            20                  25                  30
Ser Gly Ala Pro Pro Pro Ser-NH₂
            35

*Fig. 1*

EXENDIN-4

His Gly Glu Gly Thr Phe Thr Ser Asp Leu Ser Lys Gln Met Glu Glu
                5                   10                  15
Glu Ala Val Arg Leu Phe Ile Glu Trp Leu Lys Asn Gly Gly Pro Ser
            20                  25                  30
Ser Gly Ala Pro Pro Pro Ser-NH₂
            35

*Fig. 2*

GLP-1 (GLP-1[7-36]NH₂)

His Ala Glu Gly Thr Phe Thr Ser Asp Val Ser Ser Tyr Leu Glu Gly
                5                   10                  15
Gln Ala Ala Lys Glu Phe Ile Ala Trp Leu Val Lys Gly Arg-NH₂
            20                  25                  30

*Fig. 3*

| Amino Acid Position | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 |
|---|---|---|---|---|---|---|---|---|---|---|---|---|---|---|---|---|---|---|---|---|---|---|---|---|---|---|---|---|---|---|---|---|---|---|---|---|---|---|
| Compound 1 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | Gly | Gly | NH2 | | | | | | | |
| Compound 2 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | NH2 | | | | | | | | | |
| Compound 3 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Phe | Leu | Lys | Asn | NH2 | | | | | | | | | |
| Compound 4 | His | Ala | Glu | Gly | Thr | Phe | Thr | Ser | Asp | Leu | Ser | Lys | Gln | Met | Glu | Glu | Glu | Ala | Val | Arg | Leu | Phe | Ile | Glu | Phe | Leu | Lys | Asn | NH2 | | | | | | | | | |
| Compound 5 | His | Gly | Glu | Gly | Thr | Ala | Thr | Ser | Asp | Leu | Ser | Lys | Gln | Met | Glu | Glu | Glu | Ala | Val | Arg | Leu | Phe | Ile | Glu | Phe | Leu | Lys | Asn | NH2 | | | | | | | | | |
| Compound 6 | His | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Phe | Leu | Lys | Asn | NH2 | | | | | | | | | |
| Compound 7 | His | Gly | Glu | Gly | Thr | Ala | Thr | Ala | Asp | Leu | Ser | Lys | Gln | Leu | Glu | Glu | Glu | Ala | Val | Arg | Leu | Phe | Ile | Glu | Phe | Leu | Lys | Asn | NH2 | | | | | | | | | |
| Compound 8 | His | Gly | Glu | Gly | Thr | Phe | Thr | Ser | Ala | Leu | Ser | Lys | Gln | Leu | Glu | Glu | Glu | Ala | Val | Arg | Leu | Phe | Ile | Glu | Phe | Leu | Lys | Asn | NH2 | | | | | | | | | |
| Compound 9 | His | Gly | Glu | Gly | Thr | Phe | Thr | Ser | Asp | Ala | Ser | Lys | Gln | Leu | Glu | Glu | Glu | Ala | Val | Arg | Leu | Phe | Ile | Glu | Phe | Leu | Lys | Asn | NH2 | | | | | | | | | |
| Compound 10 | His | Gly | Glu | Gly | Thr | Phe | Thr | Ser | Asp | Leu | Ala | Lys | Gln | Leu | Glu | Glu | Glu | Ala | Val | Arg | Leu | Phe | Ile | Glu | Phe | Leu | Lys | Asn | NH2 | | | | | | | | | |
| Compound 11 | His | Gly | Glu | Gly | Thr | Phe | Thr | Ser | Asp | Leu | Ser | Ala | Gln | Leu | Glu | Glu | Glu | Ala | Val | Arg | Leu | Phe | Ile | Glu | Phe | Leu | Lys | Asn | NH2 | | | | | | | | | |
| Compound 12 | His | Gly | Glu | Gly | Thr | Phe | Thr | Ser | Asp | Leu | Ser | Lys | Ala | Leu | Glu | Glu | Glu | Ala | Val | Arg | Leu | Phe | Ile | Glu | Phe | Leu | Lys | Asn | NH2 | | | | | | | | | |
| Compound 13 | His | Gly | Glu | Gly | Thr | Phe | Thr | Ser | Asp | Leu | Ser | Lys | Gln | Ala | Glu | Glu | Glu | Ala | Val | Arg | Leu | Phe | Ile | Glu | Phe | Leu | Lys | Asn | NH2 | | | | | | | | | |
| Compound 14 | His | Gly | Glu | Gly | Thr | Phe | Thr | Ser | Asp | Leu | Ser | Lys | Gln | Leu | Ala | Glu | Glu | Ala | Val | Arg | Leu | Phe | Ile | Glu | Phe | Leu | Lys | Asn | NH2 | | | | | | | | | |
| Compound 15 | His | Gly | Glu | Gly | Thr | Phe | Thr | Ser | Asp | Leu | Ser | Lys | Gln | Leu | Glu | Ala | Glu | Ala | Val | Arg | Leu | Phe | Ile | Glu | Phe | Leu | Lys | Asn | NH2 | | | | | | | | | |
| Compound 16 | His | Gly | Glu | Gly | Thr | Phe | Thr | Ser | Asp | Leu | Ser | Lys | Gln | Leu | Glu | Glu | Ala | Ala | Val | Arg | Leu | Phe | Ile | Glu | Phe | Leu | Lys | Asn | NH2 | | | | | | | | | |
| Compound 17 | His | Gly | Glu | Gly | Thr | Phe | Thr | Ser | Asp | Leu | Ser | Lys | Gln | Leu | Glu | Glu | Glu | Ala | Ala | Arg | Leu | Phe | Ile | Glu | Phe | Leu | Lys | Asn | NH2 | | | | | | | | | |
| Compound 18 | His | Gly | Glu | Gly | Thr | Phe | Thr | Ser | Asp | Leu | Ser | Lys | Gln | Leu | Glu | Glu | Glu | Ala | Val | Ala | Leu | Phe | Ile | Glu | Phe | Leu | Lys | Asn | NH2 | | | | | | | | | |
| Compound 19 | His | Gly | Glu | Gly | Thr | Phe | Thr | Ser | Asp | Leu | Ser | Lys | Gln | Leu | Glu | Glu | Glu | Ala | Val | Arg | Ala | Phe | Ile | Glu | Phe | Leu | Lys | Asn | NH2 | | | | | | | | | |
| Compound 20 | His | Gly | Glu | Gly | Thr | Phe | Thr | Ser | Asp | Leu | Ser | Lys | Gln | Leu | Glu | Glu | Glu | Ala | Val | Arg | Leu | Ala | Ile | Glu | Phe | Leu | Lys | Asn | NH2 | | | | | | | | | |
| Compound 21 | His | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Ala | Leu | Lys | Asn | NH2 | | | | | | | | | |
| Compound 22 | His | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Phe | Ala | Lys | Asn | NH2 | | | | | | | | | |
| Compound 23 | His | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Phe | Leu | Ala | Asn | NH2 | | | | | | | | | |
| Compound 24 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | Gly | Gly | Pro | Ser | Ser | Gly | Ala | Pro | Pro | |
| Compound 25 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Phe | Leu | Lys | Asn | Gly | Gly | Pro | Ser | Ser | Gly | Ala | Pro | Pro | |
| Compound 26 | His | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Trp | Leu | Lys | Asn | Gly | Gly | Pro | Ser | Ser | Gly | Ala | Pro | Pro | |
| Compound 27 | His | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Phe | Leu | Lys | Ala | Gly | Gly | Pro | Ser | Ser | Gly | Ala | Pro | Pro | NH2 |
| Compound 28 | His | Gly | Glu | Gly | Thr | Phe | Thr | Ser | Asp | Leu | Ser | Lys | Gln | Met | Glu | Glu | Ala | Ala | Val | Arg | Leu | Phe | Ile | Glu | Trp | Leu | Lys | Asn | Gly | Gly | Pro | Ser | Ser | Gly | Ala | Pro | Pro | NH2 |
| Compound 29 | His | Gly | Glu | Gly | Thr | Phe | Thr | Ser | Asp | Leu | Ser | Lys | Gln | Leu | Glu | Glu | Ala | Ala | Val | Arg | Leu | Phe | Ile | Glu | Trp | Leu | Lys | Asn | Gly | Gly | Pro | Ser | Ser | Gly | Ala | Pro | Pro | NH2 |
| Compound 30 | His | Gly | Glu | Gly | Thr | Phe | Thr | Ser | Asp | Leu | Ser | Lys | Gln | Met | Glu | Glu | Ala | Ala | Val | Arg | Leu | Phe | Ile | Glu | Trp | Leu | Lys | Asn | Gly | Gly | Pro | Ser | Ser | Gly | Ala | Pro | Pro | NH2 |
| Compound 31 | His | Gly | Glu | Gly | Thr | Phe | Thr | Ser | Asp | Leu | Ser | Lys | Gln | Met | Glu | Glu | Ala | Ala | Val | Arg | Leu | Phe | Ile | Glu | Trp | Leu | Ala | Asn | Gly | Gly | Pro | Ser | Ser | Gly | Ala | Pro | Pro | NH2 |
| Compound 32 | His | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Trp | Leu | Lys | Asn | Gly | Gly | Pro | Ser | Ser | Gly | NH2 | | | |
| Compound 33 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | Gly | Gly | Pro | Ser | Ser | Gly | NH2 | | | |
| Compound 34 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Ala | Gly | Gly | Pro | Ser | Ser | Gly | NH2 | | | |
| Compound 35 | His | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Phe | Leu | Lys | Ala | Gly | Gly | Pro | Ser | Ser | Gly | NH2 | | | |

Fig. 4A

| Amino Acid Position | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 |
|---|---|---|---|---|---|---|---|---|---|---|---|---|---|---|---|---|---|---|---|---|---|---|---|---|---|---|---|---|---|---|---|---|---|---|---|---|---|---|
| Compound 36 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | Gly | Gly | Pro | Ser | NH2 | | | | | |
| Compound 37 | His | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Phe | Leu | Lys | Asn | Gly | Gly | Pro | Ser | NH2 | | | | | |
| Compound 38 | His | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Phe | Leu | Lys | Asn | Gly | Gly | Pro | NH2 | | | | | | |
| Compound 39 | His | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Phe | Leu | Lys | Asn | Gly | Gly | Pro | NH2 | | | | | | |
| Compound 40 | His | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Trp | Leu | Lys | Asn | Gly | NH2 | | | | | | | | |
| Compound 41 | His | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Phe | Leu | Lys | Asn | Gly | NH2 | | | | | | | | |
| Compound 42 | His | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Phe | Leu | Lys | Asn | Gly | Gly | iPro | Ser | Ser | Gly | Ala | iPro | iPro | NH2 |
| Compound 43 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | Gly | Gly | Pro | Ser | Ser | Gly | Ala | iPro | iPro | NH2 |
| Compound 44 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | Gly | Gly | Nme | Ser | Ser | Gly | Ala | Pro | Pro | NH2 |
| Compound 45 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | Gly | Gly | Nme | Ser | Ser | Gly | Ala | Nme | Nme | NH2 |
| Compound 46 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | Gly | Gly | hPro | Ser | Ser | Gly | Ala | hPro | hPro | NH2 |
| Compound 47 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | Gly | Gly | hPro | Ser | Ser | Gly | Ala | hPro | NH2 | |
| Compound 48 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | Gly | Gly | Pro | Ser | Ser | Gly | Ala | NH2 | | |
| Compound 49 | Arg | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | Gly | NH2 | | | | | | | | |
| Compound 50 | His | Gly | Asp | Gly | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | NH2 | | | | | | | | | |
| Compound 51 | His | Gly | Glu | Gly | Thr | Phe | Ser | Ser | Asp | Leu | Ser | Lys | Gln | Met | Glu | Glu | Glu | Ala | Val | Arg | Leu | Phe | Ile | Glu | Trp | Leu | Lys | Asn | NH2 | | | | | | | | | |
| Compound 52 | His | Gly | Glu | Gly | Thr | Phe | Ser | Thr | Asp | Leu | Ser | Lys | Gln | Met | Glu | Glu | Glu | Ala | Val | Arg | Leu | Phe | Ile | Glu | Trp | Leu | Lys | Asn | NH2 | | | | | | | | | |
| Compound 53 | His | Gly | Glu | Gly | Thr | Phe | Thr | Ser | Asp | Leu | Ser | Lys | Gln | Met | Glu | Glu | Ala | Ala | Val | Arg | Leu | Phe | Ile | Glu | Trp | Leu | Lys | Asn | NH2 | | | | | | | | | |
| Compound 54 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | NH2 | | | | | | | | | |
| Compound 55 | His | Gly | Glu | Gly | Thr | Phe | Thr | Ser | Asp | pGly | Ser | Lys | Gln | Met | Glu | Glu | Glu | Ala | Val | Arg | Leu | Phe | Ile | Glu | Trp | Leu | Lys | Asn | NH2 | | | | | | | | | |
| Compound 56 | His | Gly | Glu | Gly | Thr | Phe | Thr | Ser | Asp | Leu | Ser | Lys | Gln | Ala | Glu | Glu | Glu | Ala | Val | Arg | Leu | Phe | Ile | Glu | Trp | Leu | Lys | Asn | NH2 | | | | | | | | | |
| Compound 57 | His | Gly | Glu | Gly | Thr | Phe | Thr | Ser | Asp | Leu | Ser | Lys | Gln | Met | Glu | Glu | Glu | Ala | Val | Arg | Leu | naph | Ile | Glu | Phe | Leu | Lys | Asn | NH2 | | | | | | | | | |
| Compound 58 | His | Gly | Glu | Gly | Thr | Phe | Thr | Ser | Asp | Leu | Ser | Lys | Gln | Leu | Glu | Glu | Glu | Ala | Val | Arg | Leu | Phe | tBug | Glu | Phe | Leu | Lys | Asn | NH2 | | | | | | | | | |
| Compound 59 | His | Gly | Glu | Gly | Thr | Phe | Thr | Ser | Asp | Ala | Ser | Lys | Gln | Leu | Glu | Glu | Glu | Ala | Val | Arg | Leu | Phe | Ile | As | Phe | Leu | Lys | Asn | Gly | Gly | Pro | Ser | Ser | NH2 | | | | |
| Compound 60 | His | Gly | Glu | Gly | Thr | Phe | Thr | Ser | Asp | Ala | Ser | Lys | Gln | Leu | Glu | Glu | Glu | Ala | Val | Arg | Leu | Phe | Ile | Glu | Phe | Leu | Lys | Asn | Gly | NH2 | | | | | | | | |
| Compound 61 | His | Gly | Glu | Gly | Thr | Phe | Thr | Ser | Asp | Ala | Ser | Lys | Gln | Met | Glu | Glu | Glu | Ala | Val | Arg | Leu | Phe | Ile | Glu | Trp | Leu | Lys | Asn | Gly | Gly | hPro | Ser | Ser | Gly | Ala | hPro | hPro | NH2 |

*Fig. 4B*

| Compound No. | |
|---|---|
| 62 | 4-Imidazolylpropionyl-Gly Glu Gly Thr Phe Thr Ser Asp Leu Ser Lys Gln Met Glu Glu Ala Val Arg Leu Phe Ile Glu Trp Leu Lys Lys-NH$^\varepsilon$octanoyl Asn-NH$_2$ [SEQ. ID NO. 67] |
| 63 | 4-Imidazolylpropionyl-Gly Glu Gly Thr Phe Thr Ser Asp Leu Ser Lys Gln Leu Glu Glu Ala Val Arg Leu Phe Ile Glu Phe Leu Lys-NH$^\varepsilon$octanoyl Asn-NH$_2$ [SEQ. ID NO. 68] |
| 64 | 4-Imidazolylpropionyl-Gly Glu Gly Thr Phe Thr Ser Asp Leu Ser Lys Gln Met Glu Glu Ala Val Arg Leu Phe Ile Glu Trp Leu Lys-NH$^\varepsilon$octanoyl Asn Gly Gly-NH$_2$ [SEQ. ID NO. 69] |
| 65 | 4-Imidazolylpropionyl-Gly Glu Gly Thr Phe Thr Ser Asp Leu Ser Lys Gln Leu Glu Glu Ala Val Arg Leu Phe Ile Glu Phe Leu Lys-NH$^\varepsilon$octanoyl Asn Gly Gly-NH$_2$ [SEQ. ID NO. 70] |
| 66 | 4-Imidazolylpropionyl-Gly Glu Gly Thr Phe Thr Ser Asp Leu Ser Lys Gln Met Glu Glu Ala Val Arg Leu Phe Ile Glu Trp Leu Lys-NH$^\varepsilon$octanoyl-NH$_2$ [SEQ. ID NO. 71] |
| 67 | 4-Imidazolylpropionyl-Gly Glu Gly Thr Phe Thr Ser Asp Leu Ser Lys Gln Leu Glu Glu Ala Val Arg Leu Phe Ile Glu Phe Leu Lys-NH$^\varepsilon$octanoyl-NH$_2$ [SEQ. ID NO. 72] |
| 68 | 4-Imidazolylpropionyl-Gly Glu Gly Thr Phe Thr Ser Asp Leu Ser Lys Gln Met Glu Glu Ala Val Arg Leu Phe Ile Glu Trp Leu Asn Lys-NH$^\varepsilon$octanoyl Gly Gly-NH$_2$ [SEQ. ID NO. 73] |
| 69 | 4-Imidazolylpropionyl-Gly Glu Gly Thr Phe Thr Ser Asp Leu Ser Lys Gln Leu Glu Glu Ala Val Arg Leu Phe Ile Glu Phe Leu Asn Lys-NH$^\varepsilon$octanoyl Gly Gly-NH$_2$ [SEQ. ID NO. 74] |

Fig. 10

EXENDIN AGONIST COMPOUNDS

RELATED APPLICATIONS

This application is a continuation of U.S. application Ser. No. 09/554,533 filed Jul. 11, 2002, issued as U.S. Pat. No. 7,223,725, which is a §371 of PCT/US98/24210 filed Nov. 13, 1998, which claims priority to U.S. Provisional Application No. 60/065,442, filed Nov. 14, 1997, the contents of which are hereby incorporated by reference in their entirety.

FIELD OF THE INVENTION

The present invention relates to novel compounds which have activity as exendin agonists. These compounds are useful in treatment of Type I and II diabetes, in treatment of disorders which would be benefited by agents which lower plasma glucose levels and in treatment of disorders which would be benefited with agents useful in delaying and/or slowing gastric emptying.

BACKGROUND

The following description includes information that may be useful in understanding the present invention. It is not an admission that any of the information provided herein is prior art to the presently claimed invention, nor that any of the publications specifically or implicitly referenced are prior art to that invention.

Exendin

The exendins are peptides that are found in venom of the Gila-monster, a lizard endogenous to Arizona and Northern Mexico. Exendin-3 (SEQ ID NO:1) is present in the venom of *Heloderma horridum*, and exendin-4 (SEQ ID NO:2) is present in the venom of *Heloderma suspectum* (Eng, J., et al., J. Biol. Chem., 265:20259-62, 1990; Eng., J., et al., J. Biol. Chem., 267:7402-05, 1992). The amino acid sequence of exendin-3 is shown in FIG. 1. The amino acid sequence of exendin-4 is shown in FIG. 2. The exendins have some sequence similarity to several members of the glucagon-like peptide family, with the highest homology, 53%, being to GLP-1[7-36]NH$_2$ (SEQ ID NO:3) (Goke, et al., J. Biol. Chem., 268:19650-55, 1993). GLP-1[7-36]NH$_2$, also known as proglucagon[78-107] or simply "GLP-1" as used most often herein, has an insulinotropic effect, stimulating insulin secretion from pancreatic β-cells. GLP-1 also inhibits glucagon secretion from pancreatic α-cells (Ørsov, et al., *Diabetes*, 42:658-61, 1993; D'Alessio, et al., *J. Clin. Invest.*, 97:133-38, 1996). The amino acid sequence of GLP-1 is shown in FIG. 3. GLP-1 is reported to inhibit gastric emptying (Willms B, et al., *J Clin Endocrinol Metab* 81 (1): 327-32, 1996; Wettergren A, et al., *Dig Dis Sci* 38 (4): 665-73, 1993), and gastric acid secretion. Schjoldager B T, et al., *Dig Dis Sci* 34 (5): 703-8, 1989; O'Halloran D J, et al., *J Endocrinol* 126 (1): 169-73, 1990; Wettergren A, et al., *Dig Dis Sci* 38 (4): 665-73, 1993). GLP-1[7-37], which has an additional glycine residue at its carboxy terminus, also stimulates insulin secretion in humans (Ørsov, et al., *Diabetes*, 42:658-61, 1993).

A transmembrane G-protein adenylate-cyclase-coupled receptor believed to be responsible for the insulinotropic effect of GLP-1 has been cloned from a β-cell line (Thorens, *Proc. Natl. Acad. Sci. USA* 89:8641-45, 1992), herein after referred to as the "cloned GLP-1 receptor." Exendin-4 is reportedly acts at GLP-1 receptors on insulin-secreting βTC1 cells, at dispersed acinar cells from guinea pig pancreas, and at parietal cells from stomach; the peptide is also reported to stimulate somatostatin release and inhibit gastrin release in isolated stomachs (Goke, et al., *J. Biol. Chem.* 268:19650-55, 1993; Schepp, et al., *Eur. J. Pharmacol.*, 69:183-91, 1994; Eissele, et al., *Life Sci.*, 55:629-34, 1994). Exendin-3 and exendin-4 were reportedly found to stimulate cAMP production in, and amylase release from, pancreatic acinar cells (Malhotra, R., et al., *Regulatory Peptides*, 41:149-56, 1992; Raufman, et al., *J. Biol. Chem.* 267:21432-37, 1992; Singh, et al., *Regul. Pept.* 53:47-59, 1994). Based on their insulinotropic activities, the use of exendin-3 and exendin-4 for the treatment of diabetes mellitus and the prevention of hyperglycemia has been proposed (Eng, U.S. Pat. No. 5,424,286).

Agents which serve to delay gastric emptying have found a place in medicine as diagnostic aids in gastro-intestinal radiologic examinations. For example, glucagon is a polypeptide hormone which is produced by the α cells of the pancreatic islets of Langerhans. It is a hyperglycemic agent which mobilizes glucose by activating hepatic glycogenolysis. It can to a lesser extent stimulate the secretion of pancreatic insulin. Glucagon is used in the treatment of insulin-induced hypoglycemia, for example, when administration of glucose intravenously is not possible. However, as glucagon reduces the motility of the gastro-intestinal tract it is also used as a diagnostic aid in gastro-intestinal radiological examinations. Glucagon has also been used in several studies to treat various painful gastro-intestinal disorders associated with spasm. Daniel, et al. (Br. Med. J., 3:720, 1974) reported quicker symptomatic relief of acute diverticulitis in patients treated with glucagon compared with those who had been treated with analgesics or antispasmodics. A review by Glauser, et al. (*J. Am. Coll. Emergency Physns*, 8:228, 1979) described relief of acute esophageal food obstruction following glucagon therapy. In another study glucagon significantly relieved pain and tenderness in 21 patients with biliary tract disease compared with 22 patients treated with placebo (M. J. Stower, et al., *Br. J. Surg.*, 69:591-2, 1982).

Methods for regulating gastrointestinal motility using amylin agonists are described in International Application No. PCT/US94/10225, published Mar. 16, 1995.

Methods for regulating gastrointestinal motility using exendin agonists are described in U.S. patent application Ser. No. 08/908,867, filed Aug. 8, 1997 entitled "Methods for Regulating Gastrointestinal Motility," which application is a continuation-in-part of U.S. patent application Ser. No. 08/694,954 filed Aug. 8, 1996.

Methods for reducing food intake using exendin agonists are described in U.S. patent application Ser. No. 09/003,869, filed Jan. 7, 1998, entitled "Use of Exendin and Agonists Thereof for the Reduction of Food Intake," which claims the benefit of U.S. Provisional Application Nos. 60/034,905, filed Jan. 7, 1997, 60/055,404, filed Aug. 7, 1997, 60/065,442, filed Nov. 14, 1997 and 60/066,029, filed Nov. 14, 1997.

Novel exendin agonist compounds are described in PCT Application Serial No. PCT/US98/16387 filed Aug. 6, 1998, entitled "Novel Exendin Agonist Compounds," claiming the benefit of U.S. Provisional Application Ser. No. 60/055,404, filed Aug. 8, 1997. Other novel exendin agonist compounds are described in PCT Application Serial No. PCT/US98/24210 filed Nov. 13, 1998, entitled "Novel Exendin Agonist Compounds," which claims the benefit of U.S. Provisional Application No. 60/066,029 filed Nov. 14, 1997.

SUMMARY OF THE INVENTION

According to one aspect, the present invention provides novel exendin agonist compounds which exhibit advantageous properties which include effects in slowing gastric emptying and lowering plasma glucose levels.

According to the present invention, provided are compounds of the formula (I) (SEQ ID NO:4):

$Xaa_1$ $Xaa_2$ $Xaa_3$ Gly $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ Ala $Xaa_{19}$ $Xaa_{20}$ $Xaa_{21}$ $Xaa_{22}$ $Xaa_{23}$ $Xaa_{24}$ $Xaa_{25}$ $Xaa_{26}$ $Xaa_{27}$ $Xaa_{28}$-$Z_1$; wherein $Xaa_1$ is His, Arg or Tyr;

$Xaa_2$ is Ser, Gly, Ala or Thr;

$Xaa_3$ is Asp or Glu;

$Xaa_5$ is Ala or Thr;

$Xaa_6$ is Ala, Phe, Tyr or naphthylalanine;

$Xaa_7$ is Thr or Ser;

$Xaa_8$ is Ala, Ser or Thr;

$Xaa_9$ is Asp or Glu;

$Xaa_{10}$ is Ala, Leu, Ile, Val, pentylglycine or Met;

$Xaa_{11}$ is Ala or Ser;

$Xaa_{12}$ is Ala or Lys;

$Xaa_{13}$ is Ala or Gln;

$Xaa_{14}$ is Ala, Leu, Ile, pentylglycine, Val or Met;

$Xaa_{15}$ is Ala or Glu;

$Xaa_{16}$ is Ala or Glu;

$Xaa_{17}$ is Ala or Glu;

$Xaa_{19}$ is Ala or Val;

$Xaa_{20}$ is Ala or Arg;

$Xaa_{21}$ is Ala or Leu;

$Xaa_{22}$ is Phe, Tyr or naphthylalanine;

$Xaa_{23}$ is Ile, Val, Leu, pentylglycine, tert-butylglycine or Met;

$Xaa_{24}$ is Ala, Glu or Asp;

$Xaa_{25}$ is Ala, Trp, Phe, Tyr or naphthylalanine;

$Xaa_{26}$ is Ala or Leu;

$Xaa_{27}$ is Ala or Lys;

$Xaa_{28}$ is Ala or Asn;

$Z_1$ is —OH,

—$NH_2$

Gly-$Z_2$,

Gly Gly-$Z_2$,

Gly Gly $Xaa_{31}$-$Z_2$,

Gly Gly $Xaa_{31}$ Ser-$Z_2$,

Gly Gly $Xaa_{31}$ Ser Ser-$Z_2$,

Gly Gly $Xaa_{31}$ Ser Ser Gly-$Z_2$,

Gly Gly $Xaa_{31}$ Ser Ser Gly Ala-$Z_2$,

Gly Gly $Xaa_{31}$ Ser Ser Gly Ala $Xaa_{36}$-$Z_2$,

Gly Gly $Xaa_{31}$ Ser Ser Gly Ala $Xaa_{36}$ $Xaa_{37}$-$Z_2$ or

Gly Gly $Xaa_{31}$ Ser Ser Gly Ala $Xaa_{36}$ $Xaa_{37}$ $Xaa_{38}$-$Z_2$;

$Xaa_{31}$, $Xaa_{36}$, $Xaa_{37}$ and $Xaa_{38}$ are independently Pro, homoproline, 3Hyp, 4Hyp, thioproline, N-alkylglycine, N-alkylpentylglycine or N-alkylalanine; and $Z_2$ is —OH or —$NH_2$;

provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala. Also included within the scope of the present invention are pharmaceutically acceptable salts of the compounds of formula (I) and pharmaceutical compositions including said compounds and salts thereof.

Also within the scope of the present invention are narrower genera of compounds having peptides of various lengths, for example genera of compounds which do not include peptides having a length of 28, 29 or 30 amino acid residues, respectively. Additionally, the present invention includes narrower genera of compounds having particular amino acid sequences, for example, compounds of the formula (I) (SEQ ID NO:4):

$Xaa_1$ $Xaa_2$ $Xaa_3$ Gly $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ Ala $Xaa_{18}$ $Xaa_{19}$ $Xaa_{20}$ $Xaa_{21}$ $Xaa_{22}$ $Xaa_{23}$ $Xaa_{24}$ $Xaa_{25}$ $Xaa_{26}$ $Xaa_{27}$ $Xaa_{28}$-$Z_1$;

wherein $Xaa_1$ is His or Arg;

$Xaa_2$ is Gly or Ala;

$Xaa_3$ is Asp or Glu;

$Xaa_5$ is Ala or Thr;

$Xaa_6$ is Ala, Phe or naphthylalanine;

$Xaa_7$ is Thr or Ser;

$Xaa_8$ is Ala, Ser or Thr;

$Xaa_9$ is Asp or Glu;

$Xaa_{10}$ is Ala, Leu or pentylglycine;

$Xaa_{11}$ is Ala or Ser;

$Xaa_{12}$ is Ala or Lys;

$Xaa_{13}$ is Ala or Gln;

$Xaa_{14}$ is Ala, Leu or pentylglycine;

Xaa₁₅ is Ala or Glu;

Xaa₁₆ is Ala or Glu;

Xaa₁₇ is Ala or Glu;

Xaa₁₉ is Ala or Val;

Xaa₂₀ is Ala or Arg;

Xaa₂₁ is Ala or Leu;

Xaa₂₂ is Phe or naphthylalanine;

Xaa₂₃ is Ile, Val or tert-butylglycine;

Xaa₂₄ is Ala, Glu or Asp;

Xaa₂₅ is Ala, Trp, or Phe;

Xaa₂₆ is Ala or Leu;

Xaa₂₇ is Ala or Lys;

Xaa₂₈ is Ala or Asn;

$Z_1$ is —OH,

—NH₂,

Gly-$Z_2$,

Gly Gly -$Z_2$,

Gly Gly Xaa₃₁-$Z_2$,

Gly Gly Xaa₃₁ Ser-$Z_2$,

Gly Gly Xaa₃₁ Ser Ser-$Z_2$,

Gly Gly Xaa₃₁ Ser Ser Gly-$Z_2$,

Gly Gly Xaa₃₁ Ser Ser Gly Ala-$Z_2$,

Gly Gly Xaa₃₁ Ser Ser Gly Ala Xaa₃₆-$Z_2$,

Gly Gly Xaa₃₁ Ser Ser Gly Ala Xaa₃₆ Xaa₃₇-$Z_2$ or

Gly Gly Xaa₃₁ Ser Ser Gly Ala Xaa₃₆ Xaa₃₇ Xaa₃₈-$Z_2$;

Xaa₃₁, Xaa₃₆, Xaa₃₇ and Xaa₃₈ are independently selected from the group consisting of Pro, homoproline, thioproline and N-methylylalanine; and $Z_2$ is —OH or —NH₂;

provided that no more than three of Xaa₃, Xaa₅, Xaa₆, Xaa₈, Xaa₁₀, Xaa₁₁, Xaa₁₂, Xaa₁₃, Xaa₁₄, Xaa₁₅, Xaa₁₆, Xaa₁₇, Xaa₁₉, Xaa₂₀, Xaa₂₁, Xaa₂₄, Xaa₂₅, Xaa₂₆, Xaa₂₇ and Xaa₂₈ are Ala; and pharmaceutically acceptable salts thereof.

Also provided are compounds of the formula (II) (SEQ ID NO:66):

```
                    5                      10
Xaa₁ Xaa₂ Xaa₃ Gly Xaa₅ Xaa₆ Xaa₇ Xaa₈ Xaa₉ Xaa₁₀

Xaa₁₁ Xaa₁₂ Xaa₁₃ Xaa₁₄ Xaa₁₅ Xaa₁₆ Xaa₁₇ Ala

Xaa₁₉ Xaa₂₀ Xaa₂₁ Xaa₂₂ Xaa₂₃ Xaa₂₄ Xaa₂₅ Xaa₂₆ X₁

-Z₁; wherein
```

Xaa₁ is His, Arg, Tyr or 4-imidazopropionyl;

Xaa₂ is Ser, Gly, Ala or Thr;

Xaa₃ is Asp or Glu;

Xaa₅ is Ala or Thr;

Xaa₆ is Ala, Phe, Tyr or naphthylalanine;

Xaa₇ is Thr or Ser;

Xaa₈ is Ala, Ser or Thr;

Xaa₉ is Asp or Glu;

Xaa₁₀ is Ala, Leu, Ile, Val, pentylglycine or Met;

Xaa₁₁ is Ala or Ser;

Xaa₁₂ is Ala or Lys;

Xaa₁₃ is Ala or Gln;

Xaa₁₄ is Ala, Leu, Ile, pentylglycine, Val or Met;

Xaa₁₅ is Ala or Glu;

Xaa₁₆ is Ala or Glu;

Xaa₁₇ is Ala or Glu;

Xaa₁₉ is Ala or Val;

Xaa₂₀ is Ala or Arg;

Xaa₂₁ is Ala, Leu or Lys-NH$^\epsilon$-R where R is Lys, Arg, $C_1$-$C_{10}$ straight chain or branched alkanoyl or cycloalkylalkanoyl;

Xaa₂₂ is Phe, Tyr or naphthylalanine;

Xaa₂₃ is Ile, Val, Leu, pentylglycine, tert-butylglycine or Met;

Xaa₂₄ is Ala, Glu or Asp;

Xaa₂₅ is Ala, Trp, Phe, Tyr or naphthylalanine;

Xaa₂₆ is Ala or Leu;

$X_1$ is Lys Asn, Asn Lys, Lys-NH$^\epsilon$-R Asn, Asn Lys-NH$^\epsilon$-R, Lys-NH$^\epsilon$-R Ala, Ala Lys-NH$^\epsilon$-R where R is Lys, Arg, $C_1$-$C_{10}$ straight chain or branched alkanoyl or cycloalkylalkanoyl $Z_1$ is —OH,

—NH₂,

Gly-$Z_2$,

Gly Gly-$Z_2$,

Gly Gly Xaa₃₁-$Z_2$,

Gly Gly Xaa₃₁ Ser-$Z_2$,

Gly Gly Xaa₃₁ Ser Ser-$Z_2$,

Gly Gly Xaa₃₁ Ser Ser Gly-$Z_2$,

Gly Gly Xaa₃₁ Ser Ser Gly Ala-$Z_2$,

Gly Gly Xaa₃₁ Ser Ser Gly Ala Xaa₃₆-$Z_2$,

-continued

```
Gly Gly Xaa31 Ser Ser Gly Ala Xaa36 Xaa37-Z2 or

Gly Gly Xaa31 Ser Ser Gly Ala Xaa36 Xaa37 Xaa38-
Z2;

wherein

Xaa31, Xaa36, Xaa37 and Xaa38 are independently
selected from the group consisting of Pro,
homoproline, 3Hyp, 4Hyp, thioproline,
N-alkylglycine, N-alkylpentylglycine and
N-alkylalanine; and Z2 is —OH or —NH2;
``` provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, and $Xaa_{26}$ are Ala. Also within the scope of the present invention are pharmaceutically acceptable salts of the compounds of formula (II) and pharmaceutical compositions including said compounds and salts thereof.

Preferred exendin agonist compounds of formula (II) include those wherein $Xaa_1$ is H is, Tyr or 4-imidazopropionyl. More preferably $Xaa_1$ is His. Also, preferred are those compounds of formula (II) wherein $Xaa_1$ is 4-imidazopropionyl.

Preferred are those compounds of formula (II) wherein $Xaa_2$ is Gly.

Preferred compounds of formula (II) are those wherein $Xaa_{14}$ is Leu, pentylglycine or Met.

Preferred compounds of formula (II) are those wherein $Xaa_{25}$ is Trp or Phe.

According to one aspect, preferred are compounds of formula (II) wherein $Xaa_6$ is Phe or naphthylalanine; $Xaa_{22}$ is Phe or naphthylalanine; and $Xaa_{23}$ is Ile or Val. More preferably, $Z_1$ is —NH$_2$. According to one aspect, especially preferred are such compounds of formula (II) wherein $Xaa_{31}$, $Xaa_{36}$, $Xaa_{37}$ and $Xaa_{38}$ are independently selected from the group consisting of Pro, homoproline, thioproline and N-alkylalanine. More preferably, $Z_2$ is —NH$_2$.

Preferred compounds of formula (II) include those wherein $X_1$ is Lys Asn, Lys-NH$^\epsilon$—R Asn, or Lys-NH$^\epsilon$—R Ala where R is Lys, Arg, $C_1$-$C_{10}$ straight chain or branched alkanoyl. Especially preferred compounds of formula (II) include Compound Nos. 62-69 (SEQ ID NOs:67-74).

DEFINITIONS

In accordance with the present invention and as used herein, the following terms are defined to have the following meanings, unless explicitly stated otherwise.

The term "amino acid" refers to natural amino acids, unnatural amino acids, and amino acid analogs, all in their D and L stereoisomers if their structure allow such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), typtophan (Trp), tyrosine (Tyr) and valine (Val). Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid and thioproline. Amino acid analogs include the natural and unnatural amino acids which are chemically blocked, reversibly or irreversibly, or modified on their N-terminal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone.

The term "amino acid analog" refers to an amino acid wherein either the C-terminal carboxy group, the N-terminal amino group or side-chain functional group has been chemically codified to another functional group. For example, aspartic acid-(beta-methyl ester) is an amino acid analog of aspartic acid; N-ethylglycine is an amino acid analog of glycine; or alanine carboxamide is an amino acid analog of alanine.

The term "amino acid residue" refers to radicals having the structure: (1) —C(O)—R—NH—, wherein R typically is —CH(R')—, wherein R' is an amino acid side chain, typically H or a carbon containing substitutent; or (2)

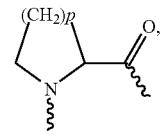

wherein p is 1, 2 or 3 representing the azetidinecarboxylic acid, proline or pipecolic acid residues, respectively.

The term "lower" referred to herein in connection with organic radicals such as alkyl groups defines such groups with up to and including about 6, preferably up to and including 4 and advantageously one or two carbon atoms. Such groups may be straight chain or branched chain.

"Pharmaceutically acceptable salt" includes salts of the compounds of the present invention derived from the combination of such compounds and an organic or inorganic acid. In practice the use of the salt form amounts to use of the base form. The compounds of the present invention are useful in both free base and salt form, with both forms being considered as being within the scope of the present invention.

In addition, the following abbreviations stand for the following:
"ACN" or "CH$_3$CN" refers to acetonitrile.
"Boc", "tBoc" or "Tboc" refers to t-butoxy carbonyl.
"DCC" refers to N,N'-dicyclohexylcarbodiimide.
"Fmoc" refers to fluorenylmethoxycarbonyl.
"HBTU" refers to 2-(1H-benzotriazol-1-yl)-1,1,3,3,-tetramethyluronium hexafluorophosphate.
"HOBt" refers to 1-hydroxybenzotriazole monohydrate.
"homoP" or hPro" refers to homoproline.
"MeAla" or "Nme" refers to N-methylalanine.
"naph" refers to naphthylalanine.
"pG" or "pGly" refers to pentylglycine.
"tBuG" refers to tertiary-butylglycine.
"ThioP" or "tPro" refers to thioproline.
"3Hyp" refers to 3-hydroxyproline
"4Hyp" refers to 4-hydroxyproline
"NAG" refers to N-alkylglycine
"NAPG" refers to N-alkylpentylglycine

BRIEF DESCRIPTION OF THE DRAWINGS

FIG. 1 depicts the amino acid sequence for exendin-3 (SEQ ID NO:1).

FIG. 2 depicts the amino acid sequence for exendin-4 (SEQ ID NO:2).

FIG. 3 depicts the amino acid sequence for GLP-1[7-36] $NH_2$ (GLP-1) (SEQ ID NO:3).

FIGS. 4A-B depict the amino acid sequences for certain compounds of the present invention, Compounds 1-61 (SEQ ID NOs:5-65).

FIG. 10 depicts the amino acid sequences for certain compounds of the present invention, Compound Nos. 62-69 (SEQ ID NOs:67-74).

DETAILED DESCRIPTION OF THE INVENTION

Figure 5:
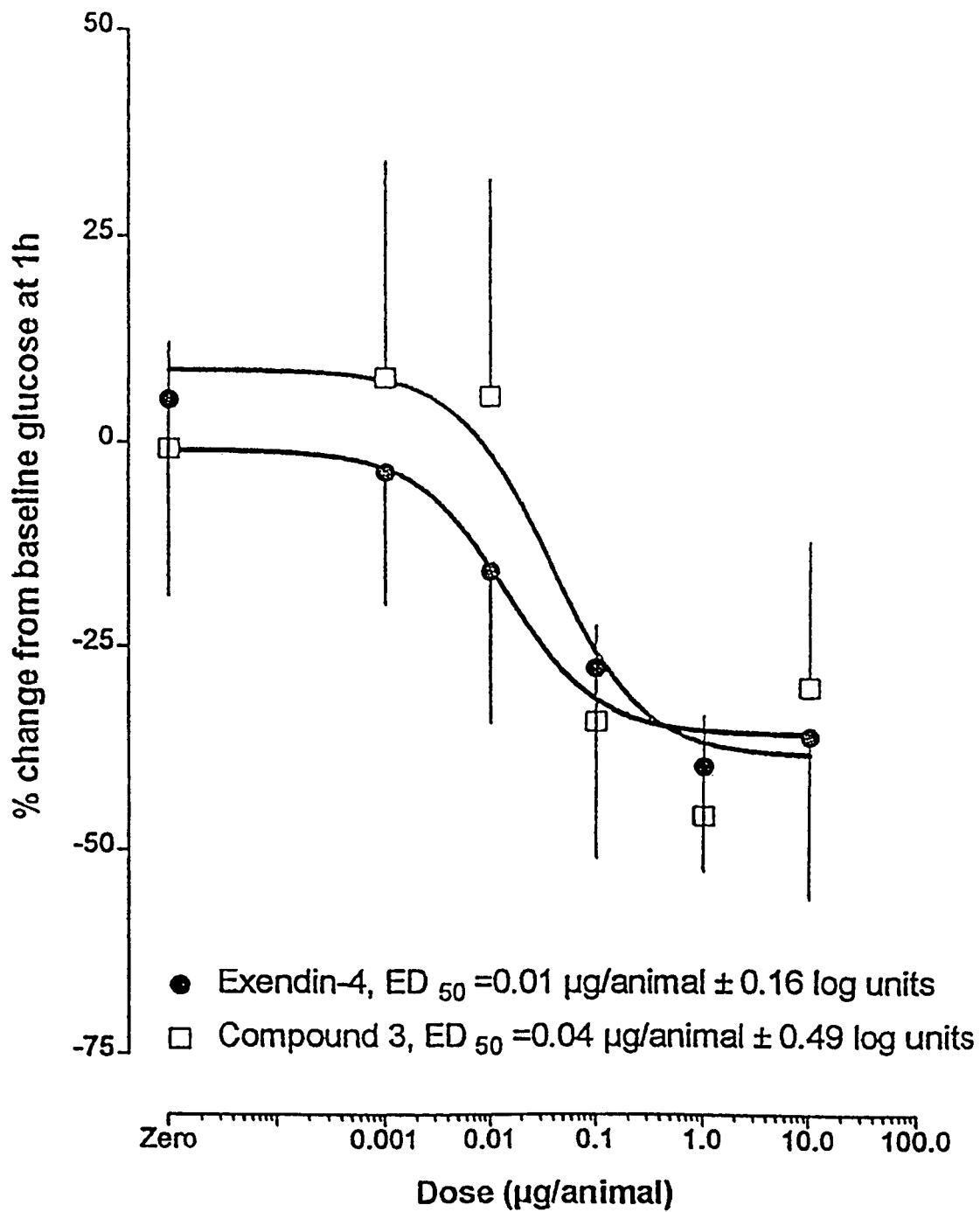
FIG. 5 depicts the effect on lowering blood glucose of various concentrations of Compound 3 (SEQ ID NO:7).
Figure 6:
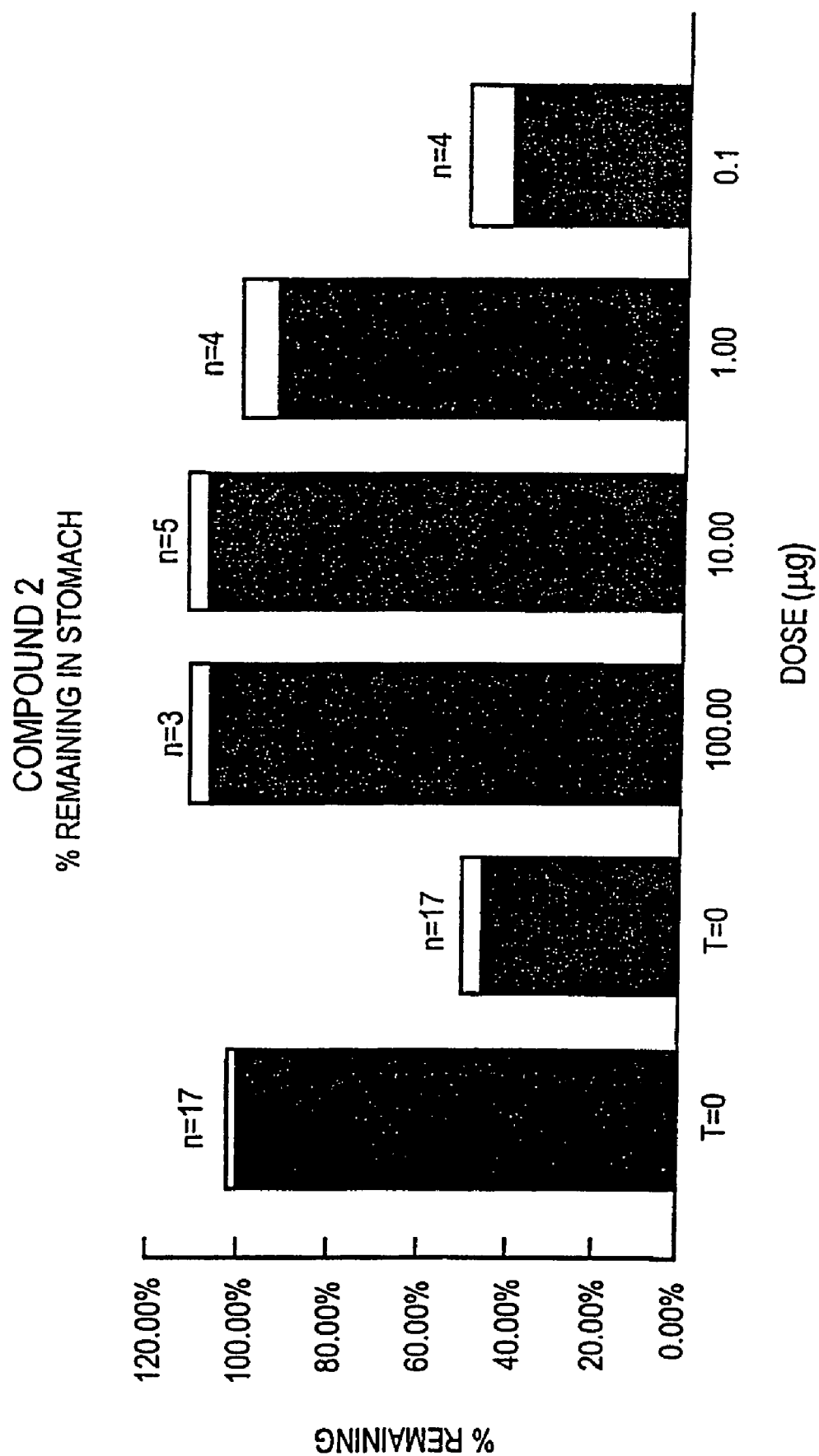
FIG. 6 depicts the effect on gastric emptying of various concentrations of Compound 2 (SEQ ID NO:6).
Figure 7:
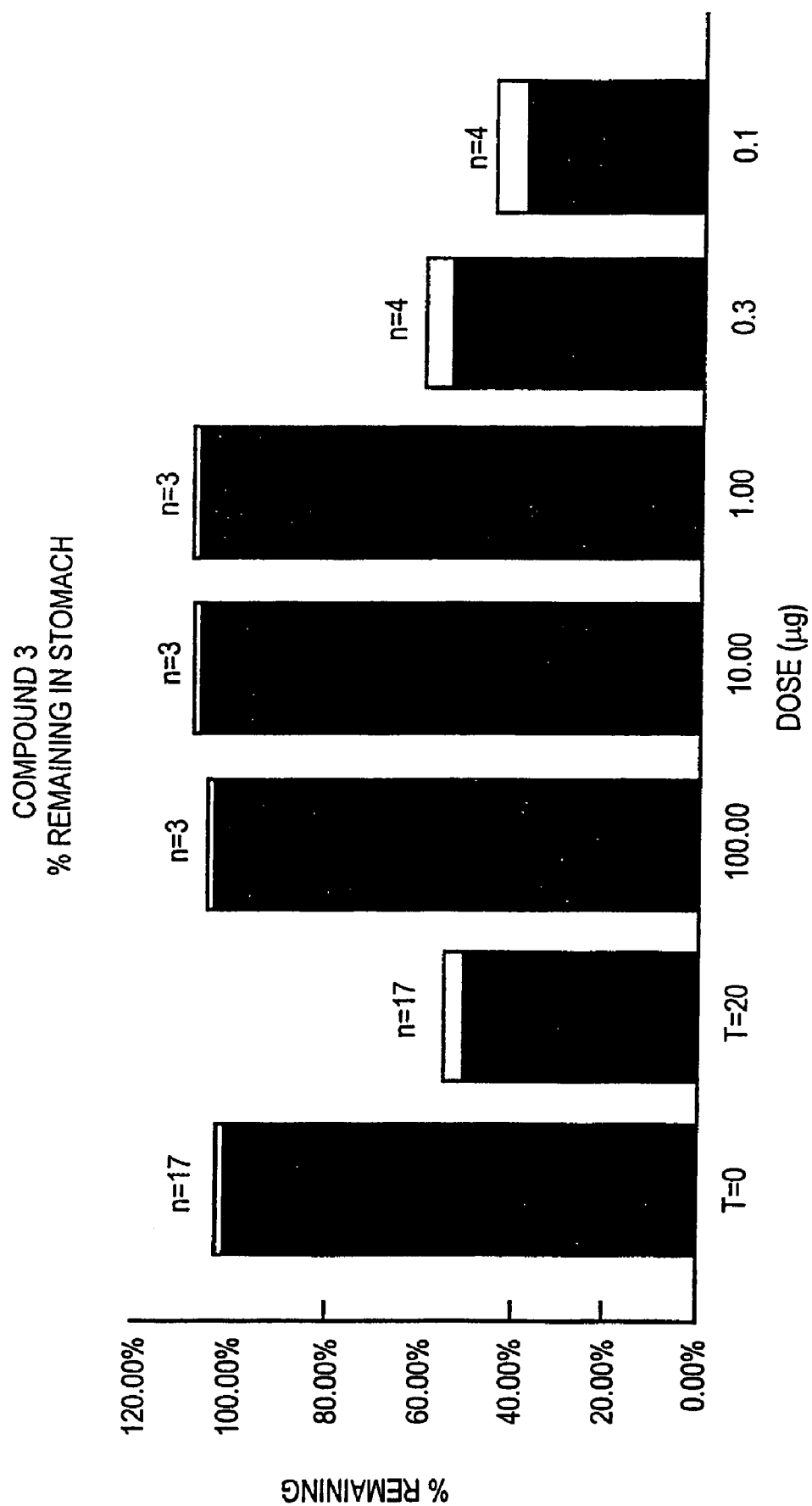
FIG. 7 depicts a comparison of effects on gastric emptying of various concentrations of Compound 3 (SEQ ID NO:7).
Figure 8:
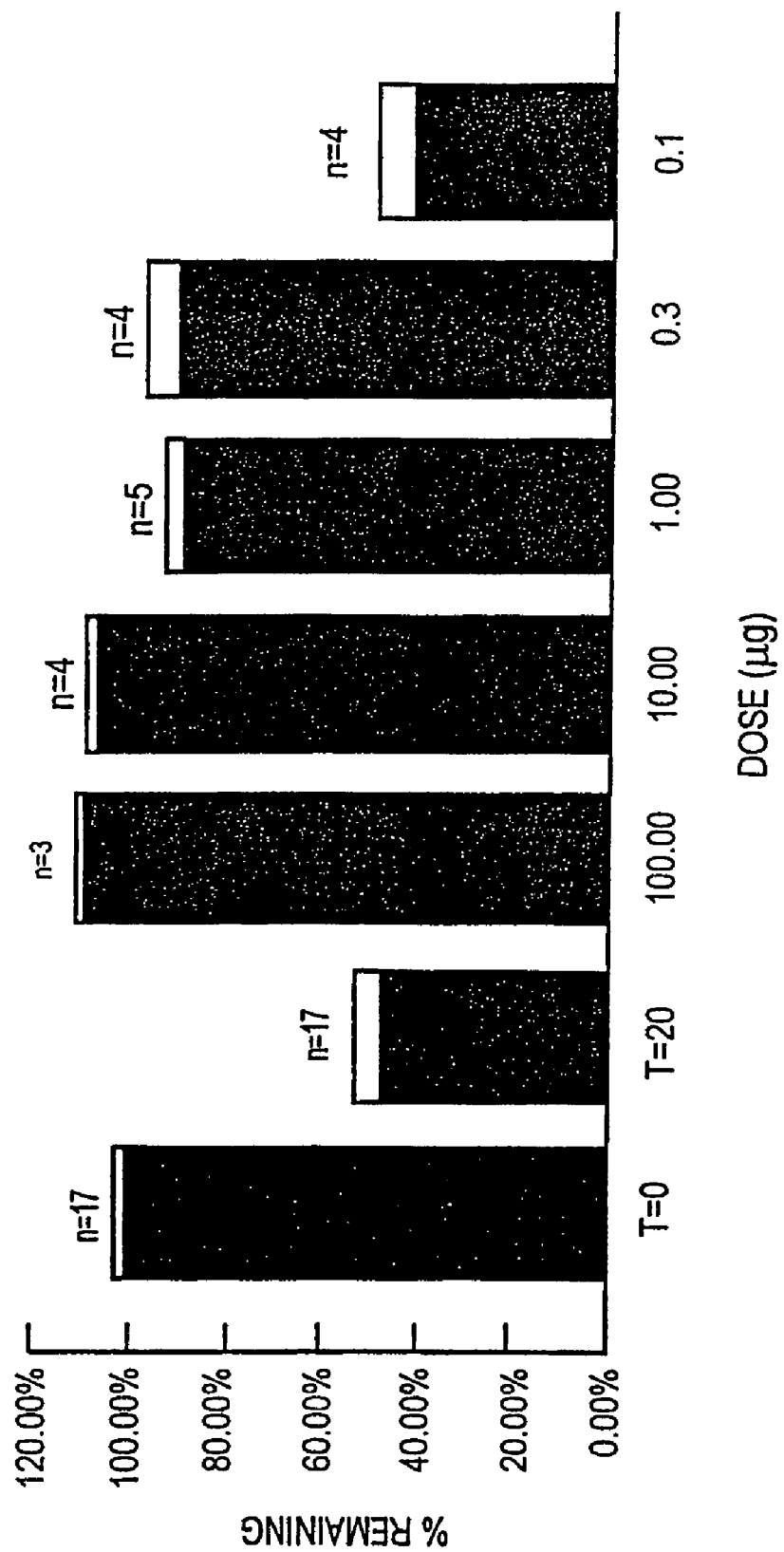
FIG. 8 depicts a comparison of effects on gastric emptying of various concentrations of Compound 10 (SEQ ID NO:14).
Figure 9:
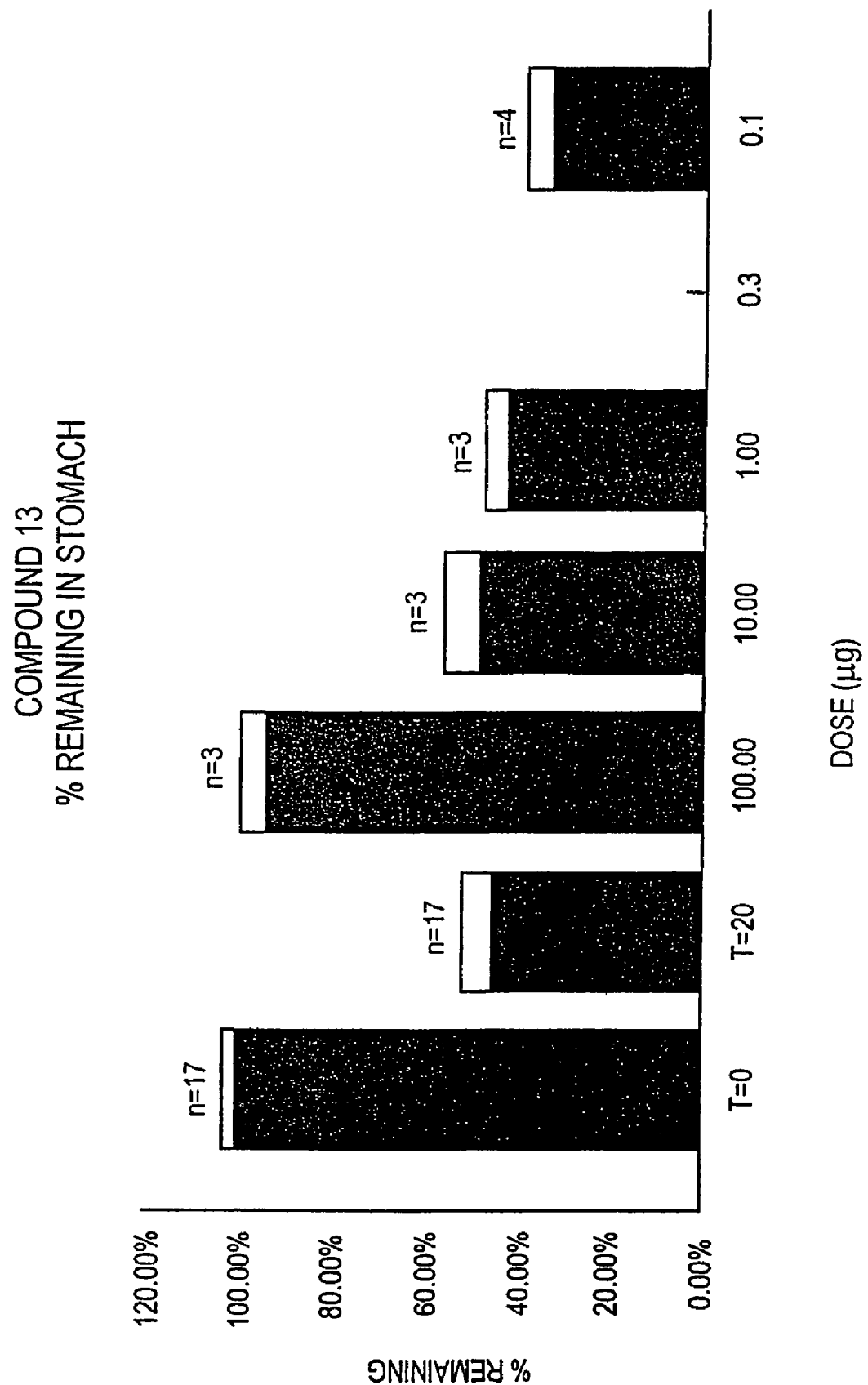
FIG. 9 depicts a comparison of effects on gastric emptying of various concentrations of Compound 13 (SEQ ID NO:17).

According to the present invention, provided are compounds of the formula (I) (SEQ ID NO:4):

$Xaa_1$ $Xaa_2$ $Xaa_3$ Gly $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ Ala $Xaa_{19}$ $Xaa_{20}$ $Xaa_{21}$ $Xaa_{22}$ $Xaa_{23}$ $Xaa_{24}$ $Xaa_{25}$ $Xaa_{26}$ $Xaa_{27}$ $Xaa_{28}$-$Z_1$; wherein $Xaa_1$ is His, Arg or Tyr;

$Xaa_2$ is Ser, Gly, Ala or Thr;

$Xaa_3$ is Asp or Glu;

$Xaa_5$ is Ala or Thr;

$Xaa_6$ is Ala, Phe, Tyr or naphthylalanine;

$Xaa_7$ is Thr or Ser;

$Xaa_8$ is Ala, Ser or Thr;

$Xaa_9$ is Asp or Glu;

$Xaa_{10}$ is Ala, Leu, Ile, Val, pentylglycine or Met;

$Xaa_{11}$ is Ala or Ser;

$Xaa_{12}$ is Ala or Lys;

$Xaa_{13}$ is Ala or Gln;

$Xaa_{14}$ is Ala, Leu, Ile, pentylglycine, Val or Met;

$Xaa_{15}$ is Ala or Glu;

$Xaa_{16}$ is Ala or Glu;

$Xaa_{17}$ is Ala or Glu;

$Xaa_{19}$ is Ala or Val;

$Xaa_{20}$ is Ala or Arg;

$Xaa_{21}$ is Ala or Leu;

$Xaa_{22}$ is Phe, Tyr or naphthylalanine;

$Xaa_{23}$ is Ile, Val, Leu, pentylglycine, tert-butylglycine or Met;

$Xaa_{24}$ is Ala, Glu or Asp;

$Xaa_{25}$ is Ala, Trp, Phe, Tyr or naphthylalanine;

$Xaa_{26}$ is Ala or Leu;

$Xaa_{27}$ is Ala or Lys;

$Xaa_{28}$ is Ala or Asn;

$Z_1$ is —OH,

—$NH_2$

Gly-$Z_2$,

Gly Gly-$Z_2$,

Gly Gly $Xaa_{31}$-$Z_2$,

Gly Gly $Xaa_{31}$ Ser-$Z_2$,

Gly Gly $Xaa_{31}$ Ser Ser-$Z_2$,

Gly Gly $Xaa_{31}$ Ser Ser Gly-$Z_2$,

Gly Gly $Xaa_{31}$ Ser Ser Gly Ala-$Z_2$,

Gly Gly $Xaa_{31}$ Ser Ser Gly Ala $Xaa_{36}$-$Z_2$,

Gly Gly $Xaa_{31}$ Ser Ser Gly Ala $Xaa_{36}$ $Xaa_{37}$-$Z_2$ or

Gly Gly $Xaa_{31}$ Ser Ser Gly Ala $Xaa_{36}$ $Xaa_{37}$ $Xaa_{38}$-$Z_2$;

$Xaa_{31}$, $Xaa_{36}$, $Xaa_{37}$ and $Xaa_{38}$ are independently Pro, homoproline, 3Hyp, 4Hyp, thioproline, N-alkylglycine, N-alkylpentylglycine or N-alkylalanine; and $Z_2$ is —OH or —$NH_2$;

provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala. Also within the scope of the present invention are pharmaceutically acceptable salts of the compounds for formula (I) and pharmaceutical compositions including said compounds and salts thereof.

Preferred N-alkyl groups for N-alkylglycine, N-alkylpentylglycine and N-alkylalanine include lower alkyl groups preferably of 1 to about 6 carbon atoms, more preferably of 1 to 4 carbon atoms. Suitable compounds of formula (I) include those identified in Examples 1-61 ("Compounds 1-61," respectively) (SEQ ID NOs:5-65), as well as those corresponding compounds identified in Examples 70 and 71.

Preferred such exendin agonist compounds include those wherein $Xaa_1$ is His or Tyr. More preferably $Xaa_1$ is His.

Preferred are those such compounds wherein $Xaa_2$ is Gly.

Preferred are those such compounds wherein $Xaa_{14}$ is Leu, pentylglycine or Met.

Preferred such compounds are those wherein Xaa$_{25}$ is Trp or Phe.

Preferred compounds of formula (I) are those where Xaa$_6$ is Phe or naphthylalanine; Xaa$_{22}$ is Phe of naphthylalanine and Xaa$_{23}$ is Ile or Val.

Preferred are compounds of formula (I) wherein Xaa$_{31}$, Xaa$_{36}$, Xaa$_{37}$ and Xaa$_{38}$ are independently selected from Pro, homoproline, thioproline and N-alkylalanine.

Preferably Z$_1$ is —NH$_2$.

Preferable Z$_2$ is —NH$_2$.

According to one aspect, preferred are compounds of formula (I) wherein Xaa$_1$ is His or Tyr, more preferably His; Xaa$_2$ is Gly; Xaa$_6$ is Phe or naphthylalanine; Xaa$_{14}$ is Leu, pentylglycine or Met; Xaa$_{22}$ is Phe or naphthylalanine; Xaa$_{23}$ is Ile or Val; Xaa$_{31}$, Xaa$_{36}$, Xaa$_{37}$ and Xaa$_{38}$ are independently selected from Pro, homoproline, thioproline or N-alkylalanine. More preferably Z$_1$ is —NH$_2$.

According to an especially preferred aspect, especially preferred compounds include those of formula (I) wherein: Xaa$_1$ is His or Arg; Xaa$_2$ is Gly or Ala; Xaa$_3$ is Asp or Glu; Xaa$_5$ is Ala or Thr; Xaa$_6$ is Ala, Phe or nephthylalaine; Xaa$_7$ is Thr or Ser; Xaa$_8$ is Ala, Ser or Thr; Xaa$_9$ is Asp or Glu; Xaa$_{10}$ is Ala, Leu or pentylglycine; Xaa$_{11}$ is Ala or Ser; Xaa$_{12}$ is Ala or Lys; Xaa$_{13}$ is Ala or Gln; Xaa$_{14}$ is Ala, Leu or pentylglycine; Xaa$_{15}$ is Ala or Glu; Xaa$_{16}$ is Ala or Glu; Xaa$_{17}$ is Ala or Glu; Xaa$_{19}$ is Ala or Val; Xaa$_{20}$ is Ala or Arg; Xaa$_{21}$ is Ala or Leu; Xaa$_{22}$ is Phe or naphthylalanine; Xaa$_{23}$ is Ile, Val or tert-butylglycine; Xaa$_{24}$ is Ala, Glu or Asp; Xaa$_{25}$ is Ala, Trp or Phe; Xaa$_{26}$ is Ala or Leu; Xaa$_{27}$ is Ala or Lys; Xaa$_{28}$ is Ala or Asn; Z$_1$ is —OH, —NH$_2$, Gly-Z$_2$, Gly Gly-Z$_2$, Gly Gly Xaa$_{31}$-Z$_2$, Gly Gly Xaa$_3$, Ser-Z$_2$, Gly Gly Xaa$_{31}$ Ser Ser-Z$_2$, Gly Gly Xaa$_{31}$ Ser Ser Gly-Z$_2$, Gly Gly Xaa$_{31}$ Ser Ser Gly Ala-Z$_2$, Gly Gly Xaa$_{31}$ Ser Ser Gly Ala Xaa$_{36}$-Z$_2$, Gly Gly Xaa$_{31}$ Ser Ser Gly Ala Xaa$_{36}$ Xaa$_{37}$-Z$_2$, Gly Gly Xaa$_{31}$ Ser Ser Gly Ala Xaa$_{36}$ Xaa$_{37}$ Xaa$_{38}$-Z$_2$; Xaa$_{31}$, Xaa$_{36}$, Xaa$_{37}$ and Xaa$_{38}$ being independently Pro homoproline, thioproline or N-methylalanine; and Z$_2$ being —OH or —NH$_2$; provided that no more than three of Xaa$_3$, Xaa$_5$, Xaa$_6$, Xaa$_8$, Xaa$_{10}$, Xaa$_{11}$, Xaa$_{12}$, Xaa$_{13}$, Xaa$_{14}$, Xaa$_{15}$, Xaa$_{16}$, Xaa$_{17}$, Xaa$_{19}$, Xaa$_{20}$, Xaa$_{21}$, Xaa$_{24}$, Xaa$_{25}$, Xaa$_{26}$, Xaa$_{27}$ and Xaa$_{28}$ are Ala. Especially preferred compounds of formula (I) include those having the amino acid sequence of SEQ ID NOs:6-27 (Compounds 2-23).

According to an especially preferred aspect, provided are compounds of compound (I) where Xaa$_{14}$ is Leu, Ile, Val or pentylglycine, more preferably Leu or pentylglycine, and Xaa$_{25}$ is Phe, Tyr or naphthylalanine, more preferably Phe or naphthylalanine. These compounds will be less susceptive to oxidative degration, both in vitro and in vivo, as well as during synthesis of the compound.

Also within the scope of the present invention are narrower genera of compounds having peptides of various lengths, for example genera of compounds which do not include peptides having a length of 28, 29, or 30 amino acid residues, respectively. Additionally, the present invention includes narrower genera of compounds having particular amino acid sequences, for example, compounds of the formula (I) (SEQ ID NO:4):

Xaa$_1$ Xaa$_2$ Xaa$_3$ Gly Xaa$_5$ Xaa$_6$ Xaa$_7$ Xaa$_8$ Xaa$_9$ Xaa$_{10}$

Xaa$_{11}$ Xaa$_{12}$ Xaa$_{13}$ Xaa$_{14}$ Xaa$_{15}$ Xaa$_{16}$ Xaa$_{17}$ Ala

Xaa$_{18}$ Xaa$_{19}$ Xaa$_{20}$ Xaa$_{21}$ Xaa$_{22}$ Xaa$_{23}$ Xaa$_{24}$ Xaa$_{25}$

Xaa$_{26}$ Xaa$_{27}$ Xaa$_{28}$-Z$_1$;

wherein

Xaa$_1$ is His or Arg;

Xaa$_2$ is Gly or Ala;

Xaa$_3$ is Asp or Glu;

Xaa$_5$ is Ala or Thr;

Xaa$_6$ is Ala, Phe or naphthylalanine;

Xaa$_7$ is Thr or Ser;

Xaa$_8$ is Ala, Ser or Thr;

Xaa$_9$ is Asp or Glu;

Xaa$_{10}$ is Ala, Leu or pentylglycine;

Xaa$_{11}$ is Ala or Ser;

Xaa$_{12}$ is Ala or Lys;

Xaa$_{13}$ is Ala or Gln;

Xaa$_{14}$ is Ala, Leu or pentylglycine;

Xaa$_{15}$ is Ala or Glu;

Xaa$_{16}$ is Ala or Glu;

Xaa$_{17}$ is Ala or Glu;

Xaa$_{19}$ is Ala or Val;

Xaa$_{20}$ is Ala or Arg;

Xaa$_{21}$ is Ala or Leu;

Xaa$_{22}$ is Phe or naphthylalanine;

Xaa$_{23}$ is Ile, Val or tert-butylglycine;

Xaa$_{24}$ is Ala, Glu or Asp;

Xaa$_{25}$ is Ala, Trp, or Phe;

Xaa$_{26}$ is Ala or Leu;

Xaa$_{27}$ is Ala or Lys;

Xaa$_{28}$ is Ala or Asn;

Z$_1$ is —OH,

—NH$_2$,

Gly-Z$_2$,

Gly Gly -Z$_2$,

Gly Gly Xaa$_{31}$-Z$_2$,

Gly Gly Xaa$_{31}$ Ser-Z$_2$,

Gly Gly Xaa$_{31}$ Ser Ser-Z$_2$,

Gly Gly Xaa$_{31}$ Ser Ser Gly-Z$_2$,

Gly Gly Xaa$_{31}$ Ser Ser Gly Ala-Z$_2$,

Gly Gly Xaa$_{31}$ Ser Ser Gly Ala Xaa$_{36}$-Z$_2$,

Gly Gly Xaa$_{31}$ Ser Ser Gly Ala Xaa$_{36}$ Xaa$_{37}$-Z$_2$ or

-continued

Gly Gly Xaa₃₁ Ser Ser Gly Ala Xaa₃₆ Xaa₃₇ Xaa₃₈-Z₂;

Xaa₃₁, Xaa₃₆, Xaa₃₇ and Xaa₃₈ are independently selected from the group consisting of Pro, homoproline, thioproline and N-methylylalanine; and Z₂ is —OH or —NH₂;

provided that no more than three of Xaa₃, Xaa₅, Xaa₆, Xaa₈, Xaa₁₀, Xaa₁₁, Xaa₁₂, Xaa₁₃, Xaa₁₄, Xaa₁₅, Xaa₁₆, Xaa₁₇, Xaa₁₉, Xaa₂₀, Xaa₂₁, Xaa₂₄, Xaa₂₅, Xaa₂₆, Xaa₂₇ and Xaa₂₈ are Ala; and pharmaceutically acceptable salts thereof.

Also provided are compounds of the formula (II) (SEQ ID NO:66):

$$Xaa_1\ Xaa_2\ Xaa_3\ Gly\ Xaa_5\ Xaa_6\ Xaa_7\ Xaa_8\ Xaa_9\ Xaa_{10}$$

$$Xaa_{11}\ Xaa_{12}\ Xaa_{13}\ Xaa_{14}\ Xaa_{15}\ Xaa_{16}\ Xaa_{17}\ Ala$$

$$Xaa_{19}\ Xaa_{20}\ Xaa_{21}\ Xaa_{22}\ Xaa_{23}\ Xaa_{24}\ Xaa_{25}\ Xaa_{26}$$

$X_1 - Z_1$; wherein

Xaa₁ is His, Arg or Tyr or 4-imidazopropionyl;

Xaa₂ is Ser, Gly, Ala or Thr;

Xaa₃ is Asp or Glu;

Xaa₅ is Ala or Thr;

Xaa₆ is Ala, Phe, Tyr or naphthylalanine;

Xaa₇ is Thr or Ser;

Xaa₈ is Ala, Ser or Thr;

Xaa₉ is Asp or Glu;

Xaa₁₀ is Ala, Leu, Ile, Val, pentylglycine or Met;

Xaa₁₁ is Ala or Ser;

Xaa₁₂ is Ala or Lys;

Xaa₁₃ is Ala or Gln;

Xaa₁₄ is Ala, Leu, Ile, pentylglycine, Val or Met;

Xaa₁₅ is Ala or Glu;

Xaa₁₆ is Ala or Glu;

Xaa₁₇ is Ala or Glu;

Xaa₁₉ is Ala or Val;

Xaa₂₀ is Ala or Arg;

Xaa₂₁ is Ala, Leu or Lys-NH$^\epsilon$-R where R is Lys, Arg, C₁-C₁₀ straight chain or branched alkanoyl or cycloalkylalkanoyl;

Xaa₂₂ is Phe, Tyr or naphthylalanine;

Xaa₂₃ is Ile, Val, Leu, pentylglycine, tert-butylglycine or Met;

Xaa₂₄ is Ala, Glu or Asp;

Xaa₂₅ is Ala, Trp, Phe, Tyr or naphthylalanine;

Xaa₂₆ is Ala or Leu;

-continued

X₁ is Lys Asn, Asn Lys, Lys-NH$^\epsilon$-R Asn, Asn Lys-NH$^\epsilon$-R, Lys-NH$^\epsilon$-R Ala, Ala Lys-NH$^\epsilon$-R where R is Lys, Arg, C₁-C₁₀ straight chain or branched alkanoyl or cyclo-alkylalkanoyl Z₁ is —OH,

—NH₂,

Gly-Z₂,

Gly Gly-Z₂,

Gly Gly Xaa₃₁-Z₂,

Gly Gly Xaa₃₁ Ser-Z₂,

Gly Gly Xaa₃₁ Ser Ser-Z₂,

Gly Gly Xaa₃₁ Ser Ser Gly-Z₂,

Gly Gly Xaa₃₁ Ser Ser Gly Ala-Z₂,

Gly Gly Xaa₃₁ Ser Ser Gly Ala Xaa₃₆-Z₂,

Gly Gly Xaa₃₁ Ser Ser Gly Ala Xaa₃₆ Xaa₃₇-Z₂ or

Gly Gly Xaa₃₁ Ser Ser Gly Ala Xaa₃₆ Xaa₃₇ Xaa₃₈-Z₂;

wherein

Xaa₃₁, Xaa₃₆, Xaa₃₇ and Xaa₃₈ are independently selected from the group consisting of Pro, homoproline, 3Hyp, 4Hyp, thioproline, N-alkylglycine, N-alkylpentylglycine and N-alkylalanine; and Z₂ is —OH or —NH₂;

provided that no more than three of Xaa₃, Xaa₅, Xaa₆, Xaa₈, Xaa₁₀, Xaa₁₁, Xaa₁₂, Xaa₁₃, Xaa₁₄, Xaa₁₅, Xaa₁₆, Xaa₁₇, Xaa₁₉, Xaa₂₀, Xaa₂₁, Xaa₂₄, Xaa₂₅, and Xaa₂₆ are Ala. Also within the scope of the present invention are pharmaceutically acceptable salts of the compound of formula (II) and pharmaceutical compositions including said compounds and salts thereof.

Preferred exendin agonist compounds of formula (II) include those wherein Xaa₁ is His, Tyr or 4-imidazopropionyl. More preferably Xaa₁ is His.

Preferred are those compounds of formula (II) wherein Xaa₁ is 4-imidazopropionyl.

Preferred are those compounds of formula (II) wherein Xaa₂ is Gly.

Preferred compounds of formula (II) are those wherein Xaa₁₄ is Leu, pentylglycine or Met.

Preferred compounds of formula (II) are those wherein Xaa₂₅ is Trp or Phe.

According to one aspect, preferred are compounds of formula (II) wherein Xaa₆ is Phe or naphthylalanine; and Xaa₂₂ is Phe or naphthylalanine; and Xaa₂₃ is Ile or Val. More preferably, Z₁ is —NH₂. According to one aspect, especially preferred are such compounds of formula (II) wherein Xaa₃₁, Xaa₃₆, Xaa₃₇ and Xaa₃₈ are independently selected from the group consisting of Pro, homoproline, thioproline and N-alkylalanine. More preferds, Z₂ is —NH₂.

Preferred compounds of formula (II) include those wherein X₁ is Lys Asn, Lys-NH$^\epsilon$—R Asn, or Lys-NH$^\epsilon$—R Ala where R is Lys, Arg, $C_1$-$C_{10}$ straight chain or branched alkanoyl. Preferred compounds of formula (II) include Compound Nos. 62-69 (SEQ ID NOs:67-74).

The compounds referenced above form salts with various inorganic and organic acids and bases. Such salts include salts prepared with organic and inorganic acids, for example, HCl, HBr, $H_2SO_4$, $H_3PO_4$, trifluoroacetic acid, acetic acid, formic acid, methanesulfonic acid, toluenesulfonic acid, maleic acid, fumaric acid and camphorsulfonic acid. Salts prepared with bases include ammonium salts, alkali metal salts, e.g. sodium and potassium salts, and alkali earth salts, e.g. calcium and magnesium salts. Acetate, hydrochloride, and trifluoroacetate salts are preferred. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Utility

The compounds described above are useful in view of their pharmacological properties. In particular, the compounds of the invention are exendin agonists, and possess activity as agents to regulate gastric motility and to slow gastric emptying, as evidenced by the ability to reduce post-prandial glucose levels in mammals.

The compounds of the present invention are useful in in vitro and in vivo scientific methods for investigation of exendins and exendin agonists for example in methods such as those described in Examples A-E below.

Preparation of Compounds

The compounds of the present invention may be prepared using standard solid-phase peptide synthesis techniques and preferably an automated or semiautomated peptide synthesizer. Typically, using such techniques, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) being preferred herein.

The solvents, amino acid derivatives and 4-methylbenzhydryl-amine resin used in the peptide synthesizer may be purchased from Applied Biosystems Inc. (Foster City, Calif.). The following side-chain protected amino acids may be purchased from Applied Biosystems, Inc.: Boc-Arg(Mts), Fmoc-Arg(Pmc), Boc-Thr(Bzl), Fmoc-Thr(t-Bu), Boc-Ser(Bzl), Fmoc-Ser(t-Bu), Boc-Tyr(BrZ), Fmoc-Tyr(t-Bu), Boc-Lys (Cl-Z), Fmoc-Lys(Boc), Boc-Glu(Bzl), Fmoc-Glu(t-Bu), Fmoc-His(Trt), Fmoc-Asn(Trt), and Fmoc-Gln(Trt). Boc-His(BOM) may be purchased from Applied Biosystems, Inc. or Bachem Inc. (Torrance, Calif.). Anisole, dimethylsulfide, phenol, ethanedithiol, and thioanisole may be obtained from Aldrich Chemical Company (Milwaukee, Wis.). Air Products and Chemicals (Allentown, Pa.) supplies HF. Ethyl ether, acetic acid and methanol may be purchased from Fisher Scientific (Pittsburgh, Pa.).

Solid phase peptide synthesis may be carried out with an automatic peptide synthesizer (Model 430A, Applied Biosystems Inc., Foster City, Calif.) using the NMP/HOBt (Option 1) system and tBoc or Fmoc chemistry (see, Applied Biosystems User's Manual for the ABI 430A Peptide Synthesizer, Version 1.3B Jul. 1, 1988, section 6, pp. 49-70, Applied Biosystems, Inc., Foster City, Calif.) with capping. Boc-peptide-resins may be cleaved with HF (−5° C. to 0° C., 1 hour). The peptide may be extracted from the resin with alternating water and acetic acid, and the filtrates lyophilized. The Fmoc-peptide resins may be cleaved according to standard methods (*Introduction to Cleavage Techniques*, Applied Biosystems, Inc., 1990, pp. 6-12). Peptides may be also be assembled using an Advanced Chem Tech Synthesizer (Model MPS 350, Louisville, Ky.).

Peptides may be purified by RP-HPLC (preparative and analytical) using a Waters Delta Prep 3000 system. A C4, C8 or C18 preparative column (10µ, 2.2×25 cm; Vydac, Hesperia, Calif.) may be used to isolate peptides, and purity may be determined using a C4, C8 or C18 analytical column (5 u, 0.46×25 cm; Vydac). Solvents (A=0.1% TFA/water and B=0.1% TFA/$CH_3CN$) may be delivered to the analytical column at a flowrate of 1.0 ml/min and to the preparative column at 15 ml/min. Amino acid analyses may be performed on the Waters Pico Tag system and processed using the Maxima program. Peptides may be hydrolyzed by vapor-phase acid hydrolysis (115° C., 20-24 h). Hydrolysates may be derivatized and analyzed by standard methods (Cohen, et al., *The Pico Tag Method: A Manual of Advanced Techniques for Amino Acid Analysis*, pp. 11-52, Millipore Corporation, Milford, Mass. (1989)). Fast atom bombardment analysis may be carried out by M-Scan, Incorporated (West Chester, Pa.). Mass calibration may be performed using cesium iodide or cesium iodide/glycerol. Plasma desorption ionization analysis using time of flight detection may be carried out on an Applied Biosystems Bio-Ion 20 mass spectrometer. Electrospray mass spectroscopy may be carried and on a VG-Trio machine.

Peptide compounds useful in the invention may also be prepared using recombinant DNA techniques, using methods now known in the art. See, e.g., Sambrook et al., *Molecular Cloning: A Laboratory Manual*, 2d Ed., Cold Spring Harbor (1989). Non-peptide compounds useful in the present invention may be prepared by art-known methods.

Formulation and Administration

Compounds of the invention are useful in view of their exendin-like effects, and may conveniently be provided in the form of formulations suitable for parenteral (including intravenous, intramuscular and subcutaneous) or nasal, sublingual, buccal or oral administration. In some cases, it will be convenient to provide an exendin agonist and another anti-gastric-emptying agent, such as glucagon, an amylin, or an amylin agonist, in a single composition or solution for administration together. In other cases, it may be more advantageous to administer another anti-emptying agent separately from said exendin agonist. In yet other cases, it may be beneficial to provide an exendin agonist either co-formulated or separately with other glucose lowering agents such as insulin. A suitable administration format may best be determined by a medical practitioner for each patient individually. Suitable pharmaceutically acceptable carriers and their formulation are described in standard formulation treatises, e.g., *Remington's Pharmaceutical Sciences* by E. W. Martin. See also Wang, Y. J. and Hanson, M. A. "Parenteral Formulations of Proteins and Peptides: Stability and Stabilizers," *Journal of Parenteral Science and Technology*, Technical Report No. 10, Supp. 42:2 S (1988).

Compounds useful in the invention can be provided as parenteral compositions for injection or infusion. They can, for example, be suspended in an inert oil, suitably a vegetable oil such as sesame, peanut, olive oil, or other acceptable carrier. Preferably, they are suspended in an aqueous carrier, for example, in an isotonic buffer solution at a pH of about 5.6 to 7.4. These compositions may be sterilized by conventional sterilization techniques, or may be sterile filtered. The compositions may contain pharmaceutically acceptable auxiliary substances as required to approximate physiological conditions, such as pH buffering agents. Useful buffers include for example, sodium acetate/acetic acid buffers. A form of repository or "depot" slow release preparation may be used so that therapeutically effective amounts of the preparation are delivered into the bloodstream over many hours or days following transdermal injection or other form of delivery.

The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions.

The claimed compounds can also be formulated as pharmaceutically acceptable salts (e.g., acid addition salts) and/or complexes thereof. Pharmaceutically acceptable salts are non-toxic salts at the concentration at which they are administered. The preparation of such salts can facilitate the pharmacological use by altering the physical-chemical characteristics of the composition without preventing the composition from exerting its physiological effect. Examples of useful alterations in physical properties include lowering the melting point to facilitate transmucosal administration and increasing the solubility to facilitate the administration of higher concentrations of the drug.

Pharmaceutically acceptable salts include acid addition salts such as those containing sulfate, hydrochloride, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents. The compositions or pharmaceutical composition can be administered by different routes including intravenously, intraperitoneal, subcutaneous, and intramuscular, orally, topically, transdermally, buccally or transmucosally.

If desired, solutions of the above compositions may be thickened with a thickening agent such as methyl cellulose. They may be prepared in emulsified form, either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, e.g., a Triton).

Compositions useful in the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compounds will be provided in dosage unit form containing an amount of an exendin agonist, with or without another anti-emptying agent. Therapeutically effective amounts of an exendin agonist for use in the control of gastric emptying and in conditions in which gastric emptying is beneficially slowed or regulated are those that decrease post-prandial blood glucose levels, preferably to no more than about 8 or 9 mM or such that blood glucose levels are reduced as desired. In diabetic or glucose intolerant individuals, plasma glucose levels are higher than in normal individuals. In such individuals, beneficial reduction or "smoothing" of post-prandial blood glucose levels, may be obtained. As will be recognized by those in the field, an effective amount of therapeutic agent will vary with many factors including the patient's physical condition, the blood sugar level or level of inhibition of gastric emptying to be obtained, and other factors.

Such pharmaceutical compositions are useful in causing gastric hypomotility in a subject and may be used as well in other disorders where gastric motility is beneficially reduced.

The effective daily anti-emptying dose of the compounds will typically be in the range of 0.001 or 0.005 to about 5 mg/day, preferably about 0.01 or 0.05 to 2 mg/day and more preferably about 0.05 or 0.1 to 1 mg/day, for a 70 kg patient. The exact dose to be administered is determined by the attending clinician and is dependent upon where the particular compound lies within the above quoted range, as well as upon the age, weight and condition of the individual. Administration should begin at the first sign of symptoms or shortly after diagnosis of diabetes mellitus. Administration may be by injection, preferably subcutaneous or intramuscular, or by other routes for example, by oral, nasal, sublingual or buccal administration. For oral, nasal or buccal dosages should be increased to about 5-10 fold over injection dosages.

Generally, in treating or preventing elevated, inappropriate, or undesired post-prandial blood glucose levels, the compounds of this invention may be administered to patients in need of such treatment in a dosage ranges similar to those given above, however, the compounds are administered more frequently, for example, one, two, or three times a day.

The optimal formulation and mode of administration of compounds of the present application to a patient depend on factors known in the art such as the particular disease or disorder, the desired effect, and the type of patient. While the compounds will typically be used to treat human patients, they may also be used to treat similar or identical diseases in other vertebrates such as other primates, farm animals such as swine, cattle and poultry, and sports animals and pets such as horses, dogs and cats.

To assist in understanding the present invention the following Examples are included which describe the results of a series of experiments. The experiments relating to this invention should not, of course, be construed as specifically limiting the invention and such variations of the invention, now known or later developed, which would be within the purview

Example 1

Preparation of Compound 1

[SEQ. ID. NO. 5]
His Gly Glu Gly Thr Phe Thr Ser Asp Leu Ser Lys

Gln Met Glu Glu Glu Ala Val Arg Leu Phe Ile Glu

Trp Leu Lys Asn Gly Gly-NH$_2$

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.). In general, single-coupling cycles were used throughout the synthesis and Fast Moc (HBTU activation) chemistry was employed. Deprotection (Fmoc group removal) of the growing peptide chain was achieved using piperidine. Final deprotection of the completed peptide resin was achieved using a mixture of triethylsilane (0.2 mL), ethanedithiol (0.2 mL), anisole (0.2 mL), water (0.2 mL) and trifluoroacetic acid (15 mL) according to standard methods (Introduction to Cleavage Techniques, Applied Biosystems, Inc.) The peptide was precipitated in ether/water (50 mL) and centrifuged. The precipitate was reconstituted in glacial acetic acid and lyophilized. The lyophilized peptide was dissolved in water). Crude purity was about 75%.

Used in purification steps and analysis were Solvent A (0.1% TFA in water) and Solvent B (0.1% TFA in ACN).

The solution containing peptide was applied to a preparative C-18 column and purified (10% to 40% Solvent B in Solvent A over 40 minutes). Purity of fractions was determined isocratically using a C-18 analytical column. Pure fractions were pooled furnishing the above-identified peptide. Analytical RP-HPLC (gradient 30% to 50% Solvent B in Solvent A over 30 minutes) of the lyophilized peptide gave product peptide having an observed retention time of 18.9 minutes. Electrospray Mass Spectrometry (M): calculated 3408.0; found 3408.9.

Example 2

Preparation of Compound 2

[SEQ. ID. NO. 6]
His Gly Glu Gly Thr Phe Thr Ser Asp Leu Ser Lys

Gln Met Glu Glu Glu Ala Val Arg Leu Phe Ile Glu

Trp Leu Lys Asn-NH$_2$

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis were Solvent A (0.1% TFA in water) and Solvent B (0.1% TFA in ACN). Analytical RP-HPLC (gradient 30% to 40% Solvent B in Solvent A over 30 minutes) of the lyophilized peptide gave product peptide having an observed retention time of 17.9 minutes. Electrospray Mass Spectrometry (M): calculated 3294.7; found 3294.8.

Example 3

Preparation of Compound 3

[SEQ. ID. NO. 7]
His Gly Glu Gly Thr Phe Thr Ser Asp Leu Ser Lys

Gln Leu Glu Glu Glu Ala Val Arg Leu Phe Ile Glu

Phe Leu Lys Asn-NH$_2$

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis were Solvent A (0.1% TFA in water) and Solvent B (0.1% TFA in ACN). Analytical RP-HPLC (gradient 29% to 36% Solvent B in Solvent A over 30 minutes) of the lyophilized peptide gave product peptide having an observed retention time of 20.7 minutes. Electrospray Mass Spectrometry (M): calculated 3237.6; found 3240.

Example 4

Preparation of Compound 4

[SEQ. ID. NO. 8]
His Ala Glu Gly Thr Phe Thr Ser Asp Leu Ser Lys

Gln Leu Glu Glu Glu Ala Val Arg Leu Phe Ile Glu

Phe Leu Lys Asn-NH$_2$

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis were Solvent A (0.1% TFA in water) and Solvent B (0.1% TFA in ACN). Analytical RP-HPLC (gradient 36% to 46% Solvent B in Solvent A over 30 minutes) of the lyophilized peptide gave product peptide having an observed retention time of 15.2 minutes. Electrospray Mass Spectrometry (M): calculated 3251.6; found 3251.5.

Example 5

Preparation of Compound 5

[SEQ. ID. NO. 9]
His Gly Glu Gly Ala Phe Thr Ser Asp Leu Ser Lys

Gln Leu Glu Glu Glu Ala Val Arg Leu Phe Ile Glu

Phe Leu Lys Asn-NH$_2$

The above amidated peptide was assembled on 4-(2'-4'-dimethoxyphenyl)-Fmoc aminomethyl phenoxy acetamide norleucine MBHA resin (Novabiochem, 0.55 mmole/g)

using Fmoc-protected amino acids (Applied Biosystems, Inc.), cleaved from the resin, deprotected and purified in a similar way to Compound 1. Used in analysis were Solvent A (0.1% TFA in water) and Solvent B (0.1% TFA in ACN). Analytical RP-HPLC (gradient 36% to 46% Solvent B in Solvent A over 30 minutes) of the lyophilized peptide gave product peptide having an observed retention time of 13.1 minutes. Electrospray Mass Spectrometry (M): calculated 3207.6; found 3208.3.

Example 6

Preparation of Compound 6

[SEQ. ID. NO. 10]
His Gly Glu Gly Thr Ala Thr Ser Asp Leu Ser Lys

Gln Leu Glu Glu Glu Ala Val Arg Leu Phe Ile Glu

Phe Leu Lys Asn-NH$_2$

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis were Solvent A (0.1% TFA in water) and Solvent B (0.1% TFA in ACN). Analytical RP-HPLC (gradient 35% to 45% Solvent B in Solvent A over 30 minutes) of the lyophilized peptide gave product peptide having an observed retention time of 12.8 minutes. Electrospray Mass Spectrometry (M): calculated 3161.5; found 3163.

Example 7

Preparation of Compound 7

[SEQ. ID. NO. 11]
His Gly Glu Gly Thr Phe Thr Ala Asp Leu Ser Lys

Gln Leu Glu Glu Glu Ala Val Arg Leu Phe Ile Glu

Phe Leu Lys Asn-NH$_2$

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis were Solvent A (0.1% TFA in water) and Solvent B (0.1% TFA in ACN). Analytical RP-HPLC (gradient 36% to 46% Solvent B in Solvent A over 30 minutes) of the lyophilized peptide gave product peptide having an observed retention time of 15.2 minutes. Electrospray Mass Spectrometry (M): calculated 3221.6; found 3222.7.

Example 8

Preparation of Compound 8

[SEQ. ID. NO. 12]
His Gly Glu Gly Thr Phe Thr Ser Asp Ala Ser Lys

Gln Leu Glu Glu Glu Ala Val Arg Leu Phe Ile Glu

Phe Leu Lys Asn-NH$_2$

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis were Solvent A (0.1% TFA in water) and Solvent B (0.1% TFA in ACN). Analytical RP-HPLC (gradient 34% to 44% Solvent B in Solvent A over 30 minutes) of the lyophilized peptide gave product peptide having an observed retention time of 14.3 minutes. Electrospray Mass Spectrometry (M): calculated 3195.5; found 3199.4.

Example 9

Preparation of Compound 9

[SEQ. ID. NO. 13]
His Gly Glu Gly Thr Phe Thr Ser Asp Leu Ala Lys

Gln Leu Glu Glu Glu Ala Val Arg Leu Phe Ile Glu

Phe Leu Lys Asn-NH$_2$

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis were Solvent A (0.1% TFA in water) and Solvent B (0.1% TFA in ACN). Analytical RP-HPLC (gradient 38% to 48% Solvent B in Solvent A over 30 minutes) of the lyophilized peptide gave product peptide having an observed retention time of 15.7 minutes. Electrospray Mass Spectrometry (M): calculated 3221.6; found 3221.6.

Example 10

Preparation of Compound 10

[SEQ. ID. NO. 14]
His Gly Glu Gly Thr Phe Thr Ser Asp Leu Ser Ala

Gln Leu Glu Glu Glu Ala Val Arg Leu Phe Ile Glu

Phe Leu Lys Asn-NH$_2$

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis were Solvent A (0.1% TFA in water) and Solvent B (0.1% TFA in ACN). Analytical RP-HPLC (gradient 38% to 48% Solvent B in Solvent A over 30 minutes) of the lyophilized peptide gave product peptide having an observed retention time of 18.1 minutes. Electrospray Mass Spectrometry (M): calculated 3180.5; found 3180.9.

Example 11

Preparation of Compound 11

[SEQ. ID. NO. 15]
His Gly Glu Gly Thr Phe Thr Ser Asp Leu Ser Lys

Ala Leu Glu Glu Glu Ala Val Arg Leu Phe Ile Glu

Phe Leu Lys Asn-NH$_2$

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis were Solvent A (0.1% TFA in water) and Solvent B (0.1% TFA in ACN). Analytical RP-HPLC (gradient 36% to 46% Solvent B in Solvent A over 30 minutes) of the lyophilized peptide gave product peptide having an observed retention time of 17.0 minutes. Electrospray Mass Spectrometry (M): calculated 3180.6; found 3182.8.

Example 12

Preparation of Compound 12

[SEQ. ID. NO. 16]
His Gly Glu Gly Thr Phe Thr Ser Asp Leu Ser Lys

Gln Ala Glu Glu Glu Ala Val Arg Leu Phe Ile Glu

Phe Leu Lys Asn-NH$_2$

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis were Solvent A (0.1% TFA in water) and Solvent B (0.1% TFA in ACN). Analytical RP-HPLC (gradient 32% to 42% Solvent B in Solvent A over 30 minutes) of the lyophilized peptide gave product peptide having an observed retention time of 14.9 minutes. Electrospray Mass Spectrometry (M): calculated 3195.5; found 3195.9.

Example 13

Preparation of Compound 13

[SEQ. ID. NO. 17]
His Gly Glu Gly Thr Phe Thr Ser Asp Leu Ser Lys

Gln Leu Ala Glu Glu Ala Val Arg Leu Phe Ile Glu

Phe Leu Lys Asn-NH$_2$

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis were Solvent A (0.1% TFA in water) and Solvent B (0.1% TFA in ACN). Analytical RP-HPLC (gradient 37% to 47% Solvent B in Solvent A over 30 minutes) of the lyophilized peptide gave product peptide having an observed retention time of 17.9 minutes. Electrospray Mass Spectrometry (M): calculated 3179.6; found 3179.0.

Example 14

Preparation of Compound 14

[SEQ. ID. NO. 18]
His Gly Glu Gly Thr Phe Thr Ser Asp Leu Ser Lys

Gln Leu Glu Ala Glu Ala Val Arg Leu Phe Ile Glu

Phe Leu Lys Asn-NH$_2$

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis were Solvent A (0.1% TFA in water) and Solvent B (0.1% TFA in ACN). Analytical RP-HPLC (gradient 37% to 47% Solvent B in Solvent A over 30 minutes) of the lyophilized peptide gave product peptide having an observed retention time of 14.3 minutes. Electrospray Mass Spectrometry (M): calculated 3179.6; found 3180.0.

Example 15

Preparation of Compound 15

[SEQ. ID. NO. 19]
His Gly Glu Gly Thr Phe Thr Ser Asp Leu Ser Lys

Gln Leu Glu Glu Ala Ala Val Arg Leu Phe Ile Glu

Phe Leu Lys Asn-NH$_2$

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis were Solvent A (0.1% TFA in water) and Solvent B (0.1% TFA in ACN). Analytical RP-HPLC (gradient 37% to 47% Solvent B in Solvent A over 30 minutes) of the lyophilized peptide gave product peptide having an observed retention time of 13.7 minutes. Electrospray Mass Spectrometry (M): calculated 3179.6; found 3179.0.

Example 16

Preparation of Compound 16

[SEQ. ID. NO. 20]
His Gly Glu Gly Thr Phe Thr Ser Asp Leu Ser Lys

Gln Leu Glu Glu Glu Ala Ala Arg Leu Phe Ile Glu

Phe Leu Lys Asn-NH$_2$

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis were Solvent A (0.1% TFA in water) and Solvent B (0.1% TFA in ACN). Analytical RP-HPLC (gradient 35% to 45% Solvent B in Solvent A over 30 minutes) of the lyophilized peptide gave product peptide having an observed retention time of 14.0 minutes. Electrospray Mass Spectrometry (M): calculated 3209.6; found 3212.8.

Example 17

Preparation of Compound 17

[SEQ. ID. NO. 21]
His Gly Glu Gly Thr Phe Thr Ser Asp Leu Ser Lys

Gln Leu Glu Glu Glu Ala Val Ala Leu Phe Ile Glu

Phe Leu Lys Asn-NH$_2$

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis were Solvent A (0.1% TFA in water) and Solvent B (0.1% TFA in ACN). Analytical RP-HPLC (gradient 38% to 48% Solvent B in Solvent A over 30 minutes) of the lyophilized peptide gave product peptide having an observed retention time of 14.3 minutes. Electrospray Mass Spectrometry (M): calculated 3152.5; found 3153.5.

Example 18

Preparation of Compound 18

[SEQ. ID. NO. 22]
His Gly Glu Gly Thr Phe Thr Ser Asp Leu Ser Lys

Gln Leu Glu Glu Glu Ala Val Arg Ala Phe Ile Glu

Phe Leu Lys Asn-NH$_2$

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis were Solvent A (0.1% TFA in water) and Solvent B (0.1% TFA in ACN). Analytical RP-HPLC (gradient 35% to 45% Solvent B in Solvent A over 30 minutes) of the lyophilized peptide gave product peptide having an observed retention time of 12.1 minutes. Electrospray Mass Spectrometry (M): calculated 3195.5; found 3197.7.

Example 19

Preparation of Compound 19

[SEQ. ID. NO. 23]
His Gly Glu Gly Thr Phe Thr Ser Asp Leu Ser Lys

Gln Leu Glu Glu Glu Ala Val Arg Leu Phe Ile Ala

Phe Leu Lys Asn-NH$_2$

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis were Solvent A (0.1% TFA in water) and Solvent B (0.1% TFA in ACN). Analytical RP-HPLC (gradient 38% to 48% Solvent B in Solvent A over 30 minutes) of the lyophilized peptide gave product peptide having an observed retention time of 10.9 minutes. Electrospray Mass Spectrometry (M): calculated 3179.6; found 3180.5.

Example 20

Preparation of Compound 20

[SEQ. ID. NO. 24]
His Gly Glu Gly Thr Phe Thr Ser Asp Leu Ser Lys

Gln Leu Glu Glu Glu Ala Val Arg Leu Phe Ile Glu

Ala Leu Lys Asn-NH$_2$

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis were Solvent A (0.1% TFA in water) and Solvent B (0.1% TFA in ACN). Analytical RP-HPLC (gradient 32% to 42% Solvent B in Solvent A over 30 minutes) of the lyophilized peptide gave product peptide having an observed retention time of 17.5 minutes. Electrospray Mass Spectrometry (M): calculated 3161.5; found 3163.0.

Example 21

Preparation of Compound 21

[SEQ. ID. NO. 25]
His Gly Glu Gly Thr Phe Thr Ser Asp Leu Ser Lys

Gln Leu Glu Glu Glu Ala Val Arg Leu Phe Ile Glu

Phe Ala Lys Asn-NH$_2$

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis were Solvent A (0.1% TFA in water) and Solvent B (0.1% TFA in ACN). Analytical RP-HPLC (gradient 32% to 42% Solvent B in Solvent A over 30 minutes) of the lyophilized peptide gave product peptide having an observed retention time of 19.5 minutes. Electrospray Mass Spectrometry (M): calculated 3195.5; found 3199.

Example 22

Preparation of Compound 22

[SEQ. ID. NO. 26]
His Gly Glu Gly Thr Phe Thr Ser Asp Leu Ser Lys

Gln Leu Glu Glu Glu Ala Val Arg Leu Phe Ile Glu

Phe Leu Ala Asn-NH$_2$

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis were Solvent A (0.1% TFA in water) and Solvent B (0.1% TFA in ACN). Analytical RP-HPLC (gradient 38% to 48% Solvent B in Solvent A over 30 minutes) of the lyophilized peptide gave product peptide having an observed retention time of 14.5 minutes. Electrospray Mass Spectrometry (M): calculated 3180.5; found 3183.7.

Example 23

Preparation of Compound 23

[SEQ. ID. NO. 27]
His Gly Glu Gly Thr Phe Thr Ser Asp Leu Ser Lys

Gln Leu Glu Glu Glu Ala Val Arg Leu Phe Ile Glu

Phe Leu Lys Ala-NH$_2$

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis were Solvent A (0.1% TFA in water) and Solvent B (0.1% TFA in ACN). Analytical RP-HPLC (gradient 34% to 44% Solvent B in Solvent A over 30 minutes) of the lyophilized peptide gave product peptide having an observed retention time of 22.8 minutes. Electrospray Mass Spectrometry (M): calculated 3194.6; found 3197.6.

Example 24

Preparation of Compound 24

[SEQ. ID. NO. 28]
His Gly Glu Gly Thr Phe Thr Ser Asp Leu Ser Lys

Gln Met Glu Glu Glu Ala Val Arg Leu Phe Ile Glu

Trp Leu Lys Asn Gly Gly Pro Ser Ser Gly Ala Pro

Pro Pro-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4099.6.

Example 25

Preparation of Compound 25

[SEQ. ID. NO. 29]
His Gly Glu Gly Thr Phe Thr Ser Asp Leu Ser Lys

Gln Leu Glu Glu Glu Ala Val Arg Leu Phe Ile Glu

Phe Leu Lys Asn Gly Gly Pro Ser Ser Gly Ala Pro

Pro Pro-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4042.5.

Example 26

Preparation of Compound 26

[SEQ. ID. NO. 30]

His Gly Glu Gly Thr Phe Thr Ser Asp Leu Ser Lys

Gln Met Glu Glu Glu Ala Val Arg Leu Phe Ile Glu

Trp Leu Lys Asn Gly Gly Pro Ser Ser Gly Ala Pro

Pro-NH$_2$

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4002.4

Example 27

Preparation of Compound 27

[SEQ. ID. NO. 31]

His Gly Glu Gly Thr Phe Thr Ser Asp Leu Ser Lys

Gln Leu Glu Glu Glu Ala Val Arg Leu Phe Ile Glu

Phe Leu Lys Asn Gly Gly Pro Ser Ser Gly Ala Pro

Pro-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3945.4.

Example 28

Preparation of Compound 28

[SEQ. ID. NO. 32]

His Gly Glu Gly Thr Phe Thr Ser Asp Leu Ser Lys

Gln Met Glu Glu Glu Ala Val Arg Leu Phe Ile Glu

Trp Leu Lys Asn Gly Gly Pro Ser Ser Gly Ala Pro-

NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3905.3.

Example 29

Preparation of Compound 29

[SEQ. ID. NO. 33]

His Gly Glu Gly Thr Phe Thr Ser Asp Leu Ser Lys

Gln Leu Glu Glu Glu Ala Val Arg Leu Phe Ile Glu

Phe Leu Lys Asn Gly Gly Pro Ser Ser Gly Ala Pro-

NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3848.2.

Example 30

Preparation of Compound 30

[SEQ. ID. NO. 34]

His Gly Glu Gly Thr Phe Thr Ser Asp Leu Ser Lys

Gln Met Glu Glu Glu Ala Val Arg Leu Phe Ile Glu

Trp Leu Lys Asn Gly Gly Pro Ser Ser Gly Ala-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is

Example 31

Preparation of Compound 31

[SEQ. ID. NO. 35]
His Gly Glu Gly Thr Phe Thr Ser Asp Leu Ser Lys

Gln Leu Glu Glu Glu Ala Val Arg Leu Phe Ile Glu

Phe Leu Lys Asn Gly Gly Pro Ser Ser Gly Ala-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3751.1.

Example 32

Preparation of Compound 32

[SEQ. ID. NO. 36]
His Gly Glu Gly Thr Phe Thr Ser Asp Leu Ser Lys

Gln Met Glu Glu Glu Ala Val Arg Leu Phe Ile Glu

Trp Leu Lys Asn Gly Gly Pro Ser Ser Gly-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3737.1.

Example 33

Preparation of Compound 33

[SEQ. ID. NO. 37]
His Gly Glu Gly Thr Phe Thr Ser Asp Leu Ser Lys

Gln Leu Glu Glu Glu Ala Val Arg Leu Phe Ile Glu

Phe Leu Lys Asn Gly Gly Pro Ser Ser Gly-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3680.1.

Example 34

Preparation of Compound 34

[SEQ. ID. NO. 38]
His Gly Glu Gly Thr Phe Thr Ser Asp Leu Ser Lys

Gln Met Glu Glu Glu Ala Val Arg Leu Phe Ile Glu

Trp Leu Lys Asn Gly Gly Pro Ser Ser-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3680.1

Example 35

Preparation of Compound 35

[SEQ. ID. NO. 39]
His Gly Glu Gly Thr Phe Thr Ser Asp Leu Ser Lys

Gln Leu Glu Glu Glu Ala Val Arg Leu Phe Ile Glu

Phe Leu Lys Asn Gly Gly Pro Ser Ser-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3623.0.

Example 36

Preparation of Compound 36

[SEQ. ID. NO. 40]
His Gly Glu Gly Thr Phe Thr Ser Asp Leu Ser Lys

Gln Met Glu Glu Glu Ala Val Arg Leu Phe Ile Glu

Trp Leu Lys Asn Gly Gly Pro Ser-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3593.0

Example 37

Preparation of Compound 37

[SEQ. ID. NO. 41]
His Gly Glu Gly Thr Phe Thr Ser Asp Leu Ser Lys

Gln Leu Glu Glu Glu Ala Val Arg Leu Phe Ile Glu

Phe Leu Lys Asn Gly Gly Pro Ser-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3535.9

Example 38

Preparation of Compound 38

[SEQ. ID. NO. 42]
His Gly Glu Gly Thr Phe Thr Ser Asp Leu Ser Lys

Gln Met Glu Glu Glu Ala Val Arg Leu Phe Ile Glu

Trp Leu Lys Asn Gly Gly Pro-NH$_2$

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3505.9.

Example 39

Preparation of Compound 39

[SEQ. ID. NO. 43]
His Gly Glu Gly Thr Phe Thr Ser Asp Leu Ser Lys

Gln Leu Glu Glu Glu Ala Val Arg Leu Phe Ile Glu

Phe Leu Lys Asn Gly Gly Pro-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3448.8.

Example 40

Preparation of Compound 40

[SEQ. ID. NO. 44]
His Gly Glu Gly Thr Phe Thr Ser Asp Leu Ser Lys

Gln Leu Glu Glu Glu Ala Val Arg Leu Phe Ile Glu

Phe Leu Lys Asn Gly Gly-NH$_2$

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3351.7.

Example 41

Preparation of Compound 41

[SEQ. ID. NO. 45]
His Gly Glu Gly Thr Phe Thr Ser Asp Leu Ser Lys

Gln Met Glu Glu Glu Ala Val Arg Leu Phe Ile Glu

Trp Leu Lys Asn Gly-NH$_2$

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3351.8.

Example 42

Preparation of Compound 42

[SEQ. ID. NO. 46]
His Gly Glu Gly Thr Phe Thr Ser Asp Leu Ser Lys

Gln Leu Glu Glu Glu Ala Val Arg Leu Phe Ile Glu

Phe Leu Lys Asn Gly-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3294.7.

Example 43

Preparation of Compound 43

[SEQ. ID. NO. 47]
His Gly Glu Gly Thr Phe Thr Ser Asp Leu Ser Lys

Gln Met Glu Glu Glu Ala Val Arg Leu Phe Ile Glu

Trp Leu Lys Asn Gly Gly tPro Ser Ser Gly Ala tPro tPro tPro-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Double couplings are required at residues 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4197.1.

Example 44

Preparation of Compound 44

[SEQ. ID. NO. 48]
His Gly Glu Gly Thr Phe Thr Ser Asp Leu Ser Lys

Gln Met Glu Glu Glu Ala Val Arg Leu Phe Ile Glu

Trp Leu Lys Asn Gly Gly Pro Ser Ser Gly Ala tPro tPro tPro-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Double couplings are required at residues 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4179.1.

Example 45

Preparation of Compound 45

[SEQ. ID. NO. 49]
His Gly Glu Gly Thr Phe Thr Ser Asp Leu Ser Lys

Gln Met Glu Glu Glu Ala Val Arg Leu Phe Ile Glu

Trp Leu Lys Asn Gly Gly NMeala Ser Ser Gly Ala Pro

Pro-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Double couplings are required at residues 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3948.3.

Example 46

Preparation of Compound 46

[SEQ. ID. NO. 50]
His Gly Glu Gly Thr Phe Thr Ser Asp Leu Ser Lys

Gln Met Glu Glu Glu Ala Val Arg Leu Phe Ile Glu

Trp Leu Lys Asn Gly Gly NMeala Ser Ser Gly Ala

NMeala Nmeala-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Double couplings are required at residues 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3840.1.

Example 47

Preparation of Compound 47

[SEQ. ID. NO. 51]
His Gly Glu Gly Thr Phe Thr Ser Asp Leu Ser Lys

Gln Met Glu Glu Glu Ala Val Arg Leu Phe Ile Glu

Trp Leu Lys Asn Gly Gly hPro Ser Ser Gly Ala hPro hPro-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Double couplings are required at residues 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4050.1.

Example 48

Preparation of Compound 48

[SEQ. ID. NO. 52]
His Gly Glu Gly Thr Phe Thr Ser Asp Leu Ser Lys

Gln Met Glu Glu Glu Ala Val Arg Leu Phe Ile Glu

Trp Leu Lys Asn Gly Gly hPro Ser Ser Gly Ala hPro-

NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. A double coupling is required at residue 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3937.1

Example 49

Preparation of Compound 49

[SEQ. ID. NO. 53]
Arg Gly Glu Gly Thr Phe Thr Ser Asp Leu Ser Lys

Gln Met Glu Glu Glu Ala Val Arg Leu Phe Ile Glu

Trp Leu Lys Asn Gly Gly Pro Ser Ser Gly Ala-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3827.2.

Example 50

Preparation of Compound 50

[SEQ. ID. NO. 54]
His Gly Asp Gly Thr Phe Thr Ser Asp Leu Ser Lys

Gln Met Glu Glu Glu Ala Val Arg Leu Phe Ile Glu

Trp Leu Lys Asn Gly Gly-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3394.8.

Example 51

Preparation of Compound 51

[SEQ. ID. NO. 55]
His Gly Glu Gly Thr Naphthylala Thr Ser Asp Leu

Ser Lys Gln Leu Glu Glu Glu Ala Val Arg Leu Phe

Ile Glu Phe Leu Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3289.5.

Example 52

Preparation of Compound 52

[SEQ. ID. NO. 56]
His Gly Glu Gly Thr Phe Ser Ser Asp Leu Ser Lys

Gln Met Glu Glu Glu Ala Val Arg Leu Phe Ile Glu

Trp Leu Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3280.7.

Example 53

Preparation of Compound 53

[SEQ. ID. NO. 57]
His Gly Glu Gly Thr Phe Ser Thr Asp Leu Ser Lys

Gln Met Glu Glu Glu Ala Val Arg Leu Phe Ile Glu

Trp Leu Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3294.7.

Example 54

Preparation of Compound 54

[SEQ. ID. NO. 58]
His Gly Glu Gly Thr Phe Thr Ser Glu Leu Ser Lys

Gln Met Ala Glu Glu Ala Val Arg Leu Phe Ile Glu

Trp Leu Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3250.7.

Example 55

Preparation of Compound 55

[SEQ. ID. NO. 59]
His Gly Glu Gly Thr Phe Thr Ser Asp pentylgly Ser

Lys Gln Leu Glu Glu Glu Ala Val Arg Leu Phe Ile

Glu Phe Leu Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3253.5.

Example 56

Preparation of Compound 56

[SEQ. ID. NO. 60]
His Gly Glu Gly Thr Phe Thr Ser Asp Leu Ser Lys

Gln Leu Glu Glu Glu Ala Val Arg Leu Naphthylala

Ile Glu Phe Leu Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3289.5.

Example 57

Preparation of Compound 57

[SEQ. ID. NO. 61]
His Gly Glu Gly Thr Phe Thr Ser Asp Leu Ser Lys

Gln Met Glu Glu Glu Ala Val Arg Leu Phe tButylgly

Glu Trp Leu Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3183.4.

Example 58

Preparation of Compound 58

[SEQ. ID. NO. 62]
His Gly Glu Gly Thr Phe Thr Ser Asp Leu Ser Lys

Gln Leu Glu Glu Glu Ala Val Arg Leu Phe Ile Asp

Phe Leu Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3237.6.

Example 59

Preparation of Compound 59

[SEQ. ID. NO. 63]
His Gly Glu Gly Thr Phe Thr Ser Asp Ala Ser Lys

Gln Leu Glu Glu Glu Ala Val Arg Leu Phe Ile Glu

Phe Leu Lys Asn Gly Gly Pro Ser Ser-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3637.9.

Example 60

Preparation of Compound 60

[SEQ. ID. NO. 64]
His Gly Glu Gly Thr Phe Thr Ser Asp Ala Ser Lys

Gln Met Glu Glu Glu Ala Val Arg Leu Phe Ile Glu

Trp Leu Lys Asn Gly-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3309.7.

Example 61

Preparation of Compound 61

[SEQ. ID. NO. 65]
His Gly Glu Gly Thr Phe Thr Ser Asp Ala Ser Lys

Gln Met Glu Glu Glu Ala Val Arg Leu Phe Ile Glu

Trp Leu Lys Asn Gly Gly hPro Ser Ser Gly Ala hPro hPro-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Double couplings are required at residues 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3711.1.

Example 62

Preparation of Peptide Having SEQ. ID. NO. 67

Compound 62, 4-imidazolylpropionyl-Gly Glu Gly Thr Phe Thr Ser Asp Leu Ser Lys Gln Met Glu Glu Glu Ala Val Arg Leu Phe Ile Glu Trp Leu Lys-NH$^\epsilon$octanoyl Asn-NH$_2$ [SEQ. ID. NO. 67], is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Fmoc-Lys-NH$^\epsilon$octanoyl acid is used for coupling at position 27. Instead of using a protected amino acid for the final coupling at position 1,4-imidazolylpropionic acid is coupled directly to the N-terminus of residues 2-28 on the resin. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3405.0

Example 63

Preparation of Peptide Having SEQ. ID. NO. 68

Compound 63, 4-imidazolylpropionyl-Gly Glu Gly Thr Phe Thr Ser Asp Leu Ser Lys Gln Leu Glu Glu Glu Ala Val Arg Leu Phe Ile Glu Phe Leu Lys-NH$^\epsilon$octanoyl Asn-NH$_2$ [SEQ. ID. NO. 68], is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Fmoc-Lys-NH$^\epsilon$octanoyl acid is used for coupling at position 27. Instead of using a protected amino acid for the final coupling at position 1, 4-imidazolylpropionic acid is coupled directly to the N-terminus of residues 2-28 on the resin. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3347.9

Example 64

Preparation of Peptide Having SEQ. ID. NO. 69

Compound 64, 4-imidazolylpropionyl-Gly Glu Gly Thr Phe Thr Ser Asp Leu Ser Lys Gln Met Glu Glu Glu Ala Val Arg Leu Phe Ile Glu Trp Leu Lys-NH$^\epsilon$octanoyl Asn Gly Gly-NH$_2$ [SEQ. ID. NO. 69], is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Fmoc-Lys-NH$^\epsilon$octanoyl acid is used for coupling at position 27. Instead of using a protected amino acid for the final coupling at position 1, 4-imidazolylpropionic acid is coupled directly to the N-terminus of residues 2-30 on the resin. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3519.0

Example 65

Preparation of Peptide Having SEQ. ID. NO. 70

Compound 65, 4-imidazolylpropionyl-Gly Glu Gly Thr Phe Thr Ser Asp Leu Ser Lys Gln Leu Glu Glu Glu Ala Val Arg Leu Phe Ile Glu Phe Leu Lys-NH$^\epsilon$octanoyl Asn Gly Gly-NH$_2$ [SEQ. ID. NO. 70], is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Fmoc-Lys-NH$^\epsilon$octanoyl acid is used for coupling at position 27. Instead of using a protected amino acid for the final coupling at position 1, 4-imidazolylpropionic acid is coupled directly to the N-terminus of residues 2-30 on the resin. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3451.9

Example 66

Preparation of Peptide Having SEQ. ID. NO. 71

Compound 66, 4-imidazolylpropionyl-Gly Glu Gly Thr Phe Thr Ser Asp Leu Ser Lys Gln Met Glu Glu Glu Ala Val Arg Leu Phe Ile Glu Trp Leu Asn Lys-NH$^\epsilon$octanoyl-NH$_2$ [SEQ. ID. NO. 71], is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Fmoc-Lys-NH$^\epsilon$octanoyl acid is used for the initial coupling onto the resin at position 28. Instead of using a protected amino acid for the final coupling at position 1, 4-imidazolylpropionic acid is coupled directly to the N-terminus of protected residues 2-28 on the resin. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3405.0

Example 67

Preparation of Peptide Having SEQ. ID. NO. 72

Compound 67, 4-imidazolylpropionyl-Gly Glu Gly Thr Phe Thr Ser Asp Leu Ser Lys Gln Leu Glu Glu Glu Ala Val Arg Leu Phe Ile Glu Phe Leu Asn Lys-NH$^\epsilon$octanoyl-NH$_2$ [SEQ. ID. NO. 72], is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Fmoc-Lys-NH$^\epsilon$octanoyl acid is used for the initial coupling onto the resin at position 28. Instead of using a protected amino acid for the final coupling at position 1, 4-imidazolylpropionic acid is coupled directly to the N-terminus of residues 2-28 on the resin. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3347.9

Example 68

Preparation of Peptide Having SEQ. ID. NO. 73

Compound 68, 4-imidazolylpropionyl-Gly Glu Gly Thr Phe Thr Ser Asp Leu Ser Lys Gln Met Glu Glu Glu Ala Val Arg Leu Phe Ile Glu Trp Leu Asn Lys-NH$^\epsilon$octanoyl Gly Gly-NH$_2$ [SEQ. ID. NO. 73], is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Fmoc-Lys-NH$^\epsilon$octanoyl acid is used for coupling at position 28. Instead of using a protected amino acid for the final coupling at position 1, 4-imidazolylpropionic acid is coupled directly to the N-terminus of protected residues 2-30 on the resin. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3519.0

Example 69

Preparation of Peptide Having SEQ. ID. NO. 74

Compound 69, 4-imidazolylpropionyl-Gly Glu Gly Thr Phe Thr Ser Asp Leu Ser Lys Gln Leu Glu Glu Glu Ala Val Arg Leu Phe Ile Glu Phe Leu Asn Lys-NH$^\epsilon$octanoyl Gly Gly-NH$_2$ [SEQ. ID. NO. 74], is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Fmoc-Lys-NH$^\epsilon$octanoyl acid is used for coupling at position 28. Instead of using a protected amino acid for the final coupling at position 1, 4-imidazolylpropionic acid is coupled directly to the N-terminus of residues 2-30 on the resin. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3451.9

Example 70

Preparation of C-Terminal Carboxylic Acid Peptides Corresponding to the Above C-Terminal Amide Sequences for Compounds 1-3, 30-37, 40-42, 49-58 and 62-69

Compounds 1-23, 30-37, 40-42, 49-58 and 62-69 [SEQ. ID. NOS. 5-27, 34-41, 44-46, 53-62 and 67-74] are assembled on the so called Wang resin (p-alkoxybenzylalcohol resin (Bachem, 0.54 mmole/g)) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry provides an experimentally determined (M).

Example 71

Preparation of C-Terminal Carboxylic Acid Peptides Corresponding to the Above C-Terminal Amide Sequences for Compounds 24-29, 38, 39 and 43-48

Compounds 24-29, 38, 39, and 43-48 [SEQ. ID. NOS. 28-33, 42, 43 and 47-52] are assembled on the 2-chlorotritylchloride resin (200-400 mesh), 2% DVB (Novabiochem, 0.4-1.0 mmole/g)) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry provides an experimentally determined (M).

Examples A to E

Reagents Used

GLP-1(7-36) [NH$_2$] was purchased from Bachem (Torrance, Calif.). All other peptides were prepared using synthesis methods such as those described therein. All chemicals were of the highest commercial grade. The cAMP SPA immunoassay was purchased from Amersham. The radioligands were purchased from New England Nuclear (Boston, Mass.). RINm5f cells (American Type Tissue Collection, Rockville, Md.) were grown in DME/F12 medium containing 10% fetal bovine serum and 2 mM L-glutamine. Cells were grown at 37° C. and 5% CO$_2$/95% humidified air and medium was replaced every 2 to 3 days. Cells were grown to confluence then harvested and homogenized using on a Polytron homogenizer. Cell homogenates were stored frozen at −70° C. until used.

Example A

GLP-1 Receptor Binding Studies

Receptor binding was assessed by measuring displacement of [$^{125}$I]GLP-1 or [$^{125}$I]exendin(9-39) from RINm5f membranes. Assay buffer contained 5 μg/ml bestatin, 1 μg/ml phosphoramidon, 1 mg/ml bovine serum albumin (fraction V), 1 mg/ml bacitracin, and 1 mM $MgCl_2$ in 20 mM HEPES, pH 7.4. To measure binding, 30 μg membrane protein (Bradford protein assay) was resuspended in 200 μl assay buffer and incubated with 60 pM [$^{125}$I]GLP-1 or [$^{125}$I]exendin(9-39) and unlabeled peptides for 120 minutes at 23° C. in 96 well plates (Nagle Nunc, Rochester, N.Y.). Incubations were terminated by rapid filtration with cold phosphatebuffered saline, pH 7.4, through polyethyleneimine-treated GF/B glass fiber filters (Wallac Inc., Gaithersburg, Md.) using a Tomtec Mach II plate harvester (Wallac Inc., Gaithersburg, Md.). Filters were dried, combined with scintillant, and radioactivity determined in a Betaplate liquid scintillant counter (Wallac Inc.).

Peptide samples were run in the assay as duplicate points at 6 dilutions over a concentration range of $10^{-6}$M to $10^{-12}$M to generate response curves. The biological activity of a sample is expressed as an $IC_{50}$ value, calculated from the raw data using an iterative curve-fitting program using a 4-parameter logistic equation (PRIZM®, GraphPAD Software, La Jolla, Calif.). The results are shown in Table I.

TABLE I

| Compound | $IC_{50}$ (nM) |
| --- | --- |
| Exendin-4 [SEQ. ID. NO. 2] | 0.70 |
| Compound 1 [SEQ. ID. NO. 5] | 0.67 |
| Compound 2 [SEQ. ID. NO. 6] | 1.21 |
| Compound 3 [SEQ. ID. NO. 7] | 0.67 |
| Compound 4 [SEQ. ID. NO. 8] | 0.42 |
| Compound 5 [SEQ. ID. NO. 9] | 1.91 |
| Compound 6 [SEQ. ID. NO. 10] | 59.05 |
| Compound 7 [SEQ. ID. NO. 11] | 5.44 |
| Compound 8 [SEQ. ID. NO. 12] | 1.75 |
| Compound 9 [SEQ. ID. NO. 13] | 0.88 |
| Compound 10 [SEQ. ID. NO. 14] | 1.96 |
| Compound 11 [SEQ. ID. NO. 15] | 0.69 |
| Compound 12 [SEQ. ID. NO. 16] | 2.94 |
| Compound 13 [SEQ. ID. NO. 17] | 7.82 |
| Compound 14 [SEQ. ID. NO. 18] | 0.04 |
| Compound 15 [SEQ. ID. NO. 19] | 0.48 |
| Compound 16 [SEQ. ID. NO. 20] | 1.10 |
| Compound 17 [SEQ. ID. NO. 21] | 21.6 |
| Compound 18 [SEQ. ID. NO. 22] | 0.63 |
| Compound 19 [SEQ. ID. NO. 23] | 0.63 |
| Compound 20 [SEQ. ID. NO. 24] | 0.94 |
| Compound 21 [SEQ. ID. NO. 25] | 9.91 |
| Compound 22 [SEQ. ID. NO. 26] | 8.24 |
| Compound 23 [SEQ. ID. NO. 27] | 0.82 |

Example B

Cyclase Activation Study

Assay buffer contained 10 μM GTP, 0.75 mM ATP, 2.5 mM $MgCl_2$, 0.5 mM phosphocreatine, 12.5 U/ml creatine kinase, 0.4 mg/ml aprotinin, 1 μM IBMX in 50 mM HEPES, pH 7.4. Membranes and peptides were combined in 100 ml of assay buffer in 96 well filter-bottom plates (Millipore Corp., Bedford, Mass.). After 20 minutes incubation at 37° C., the assay was terminated by transfer of supernatant by filtration into a fresh 96 well plate using a Millipore vacuum manifold. Supernatant cAMP contents were quantitated by SPA immunoassay.

Peptide samples were run in the assay as triplicate points at 7 dilutions over a concentration range of $10^{-6}$M to $10^{-12}$M to generate response curves. The biological activity of a particular sample was expressed as an $EC_{50}$ value, calculated as described above. Results are tabulated in Table II.

TABLE II

| Compound | $EC_{50}$ (nM) |
| --- | --- |
| Exendin-4 [SEQ. ID. NO. 2] | 0.23 |
| Compound 1 [SEQ. ID. NO. 5] | 0.3 |
| Compound 2 [SEQ. ID. NO. 6] | 0.79 |
| Compound 3 [SEQ. ID. NO. 7] | 2.35 |
| Compound 4 [SEQ. ID. NO. 8] | 0.22 |
| Compound 5 [SEQ. ID. NO. 9] | 9.85 |
| Compound 6 [SEQ. ID. NO. 10] | 79.4 |
| Compound 7 [SEQ. ID. NO. 11] | 63.6 |
| Compound 8 [SEQ. ID. NO. 12] | 6.8 |
| Compound 9 [SEQ. ID. NO. 13] | 1.68 |
| Compound 10 [SEQ. ID. NO. 14] | 5.37 |
| Compound 11 [SEQ. ID. NO. 15] | 0.48 |
| Compound 12 [SEQ. ID. NO. 16] | 15.55 |
| Compound 13 [SEQ. ID. NO. 17] | 79.6 |
| Compound 14 [SEQ. ID. NO. 18] | 1.11 |
| Compound 15 [SEQ. ID. NO. 19] | 1.05 |
| Compound 16 [SEQ. ID. NO. 20] | 5.12 |
| Compound 17 [SEQ. ID. NO. 21] | 43.6 |
| Compound 18 [SEQ. ID. NO. 22] | 0.76 |
| Compound 19 [SEQ. ID. NO. 23] | 3.68 |
| Compound 20 [SEQ. ID. NO. 24] | 5.25 |
| Compound 21 [SEQ. ID. NO. 25] | 45.1 |
| Compound 22 [SEQ. ID. NO. 26] | 20.43 |
| Compound 23 [SEQ. ID. NO. 27] | 3.05 |

Example C

Determination of Blood Glucose Levels in db/db Mice

C57BLKS/J-m-db mice at least 3 months of age were utilized for the study. The mice were obtained from The Jackson Laboratory and allowed to acclimate for at least one week before use. Mice were housed in groups of ten at 22°±1° C. with a 12:12 light:dark cycle, with lights on at 6 a.m.

All animals were deprived of food for 2 hours before taking baseline blood samples. Approximately 70 μl of blood was drawn from each mouse via eye puncture, after a light anesthesia with metophane. After collecting baseline blood samples, to measure plasma glucose concentrations, all animals receive subcutaneous injections of either vehicle (10.9% NaCl), exendin-4 or test compound (1 μg) vehicle. Blood samples were drawn again, using the same procedure, after exactly one hour from the injections, and plasma glucose concentrations were measured.

For each animal, the % change in plasma value, from baseline value, was calculated. The percent decrease in plasma glucose after one hour is shown in Table III.

TABLE III

| Test Compound | % drop in glucose | |
| --- | --- | --- |
| Exendin-4 [SEQ. ID. NO. 2] | 39% | (n = 78) |
| Compound 2 [SEQ. ID. NO. 6] | 38% | (n = 4) |
| Compound 3 [SEQ. ID. NO. 7] | 49% | (n = 4) |
| Compound 4 [SEQ. ID. NO. 8] | 27% | (n = 4) |
| Compound 5 [SEQ. ID. NO. 9] | 47% | (n = 4) |
| Compound 6 [SEQ. ID. NO. 10] | 40% | (n = 5) |
| Compound 7 [SEQ. ID. NO. 11] | 31% | (n = 4) |
| Compound 8 [SEQ. ID. NO. 12] | 44% | (n = 4) |
| Compound 9 [SEQ. ID. NO. 13] | 41% | (n = 4) |
| Compound 10 [SEQ. ID. NO. 14] | 46% | (n = 4) |
| Compound 11 [SEQ. ID. NO. 15] | 40% | (n = 4) |
| Compound 12 [SEQ. ID. NO. 16] | 53% | (n = 4) |
| Compound 13 [SEQ. ID. NO. 17] | 45% | (n = 4) |
| Compound 14 [SEQ. ID. NO. 18] | 54% | (n = 4) |
| Compound 15 [SEQ. ID. NO. 19] | 45% | (n = 4) |

TABLE III-continued

| Test Compound | % drop in glucose | |
|---|---|---|
| Compound 16 [SEQ. ID. NO. 20] | 54% | (n = 4) |
| Compound 17 [SEQ. ID. NO. 21] | 45% | (n = 4) |
| Compound 18 [SEQ. ID. NO. 22] | 50% | (n = 4) |
| Compound 19 [SEQ. ID. NO. 23] | 48% | (n = 4) |
| Compound 20 [SEQ. ID. NO. 24] | 37% | (n = 4) |
| Compound 21 [SEQ. ID. NO. 25] | 30% | (n = 4) |
| Compound 22 [SEQ. ID. NO. 26] | 46% | (n = 4) |
| Compound 23 [SEQ. ID. NO. 27] | 42% | (n = 4) |

Example D

Dose Response Determination of Blood Glucose Levels in db/db Mice

C57BLKS/J-m-db/db mice, at least 3 months of age were utilized for the study. The mice were obtained from The Jackson Laboratory and allowed to acclimate for at least one week before use. Mice were housed in groups of ten at 22° C. 1° C. with a 12:12 light:dark cycle, with lights on at 6 a.m.

All animals were deprived of food for 2 hours before taking baseline blood samples. Approximately 70 µl of blood was drawn from each mouse via eye puncture, after a light anesthesia with metophane. After collecting baseline blood samples, to measure plasma glucose concentrations, all animals receive subcutaneous injections of either vehicle, exendin-4 or test compound in concentrations indicated. Blood samples were drawn again, using the same procedure, after exactly one hour from the injections, and plasma glucose concentrations were measured.

For each animal, the % change in plasma value, from baseline value, was calculated and a dose dependent relationship was evaluated using Graphpad Prizm™ software.

FIG. 5 depicts the effects of varying doses of exendin-4 [SEQ. ID. NO. 2] and Compound 3 [SEQ. ID. NO. 7] on plasma glucose levels. Exendin-4 had an $ED_{50}$ of 0.01 µg per mouse and Compound 3 had an $ED_{50}$ of 0.04 µg per mouse.

Example E

Gastric Emptying

The following study was carried out to examine the effects of exendin-4 and exendin agonist compounds of the present invention on gastric emptying in rats. This experiment followed a modification of the method of Scarpignato, et al., Arch. Int. Pharmacodyn. Ther. 246:286-94, 1980.

Male Harlan Sprague Dawley (HSD) rats were used. All animals were housed at 22.7±0.8 C in a 12:12 hour light:dark cycle (experiments being performed during the light cycle) and were fed and watered ad libitum (Diet LM-485, Teklad, Madison, Wis.). Exendin-4 was synthesized according to standard peptide synthesis methods. The preparation of Compounds 2, 3, 10 and 13 [SEQ. ID. NOS. 6, 7, 14 and 17] is described in Examples 2, 3, 10 and 13, respectively.

The determination of gastric emptying by the method described below was performed after a fast of ~20 hours to ensure that the stomach contained no chyme that would interfere with spectrophotometric absorbance measurements.

Conscious rats received by gavage, 1.5 ml of an acaloric gel containing 1.5% methyl cellulose (M-0262, Sigma Chemical Co, St Louis, Mo.) and 0.05% phenol red indicator. Twenty minutes after gavage, rats were anesthetized using 5% halothane, the stomach exposed and clamped at the pyloric and lower esophageal sphincters using artery forceps, removed and opened into an alkaline solution which was made up to a fixed volume. Stomach content was derived from the intensity of the phenol red in the alkaline solution, measured by absorbance at a wavelength of 560 nm. In separate experiments on 7 rats, the stomach and small intestine were both excised and opened into an alkaline solution. The quantity of phenol red that could be recovered from the upper gastrointestinal tract within 20 minutes of gavage was 89±4%; dye which appeared to bind irrecoverably to the gut luminal surface may have accounted for the balance. To account for a maximal dye recovery of less than 100%, percent of stomach contents remaining after 20 min were expressed as a fraction of the gastric contents recovered from control rats sacrificed immediately after gavage in the same experiment. Percent gastric contents remaining=(absorbance at 20 min)/(absorbance at 0 mm)×100.

In baseline studies, with no drug treatment, gastric emptying over 20 min was determined. In dose-response studies, rats were treated with 0.01, 0.1, 0.3, 1, 10 and 100 µg of exendin-4, and 0.1, 0.3, 1, 10 and 100 µg of Compounds 2, 3, 10 and 13 [SEQ. ID. NOS. 6, 7, 14 and 17].

The results, shown in FIGS. 6-9, show that the exendin agonists, Compounds 2, 3, 10 and 13, are potent inhibitors of gastric emptying. The $EC_{50}$ for exendin-4 was 0.27 µg. The $EC_{50}$ for Compound 2 was 0.79 µg, for Compound 3 was 0.34 µg, for Compound 10 was 0.27 µg, and for Compound 13 was 60 µg.

We claim:

1. A compound consists of $Xaa_1$ $Xaa_2$ $Xaa_3$ Gly $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ Ala $Xaa_{19}$ $Xaa_{20}$ $Xaa_{21}$ $Xaa_{22}$ $Xaa_{23}$ $Xaa_{24}$ $Xaa_{25}$ $Xaa_{26}$ $Xaa_{27}$ $Xaa_{28}$-$Z_1$; wherein $Xaa_1$ is His, Arg or Tyr;

$Xaa_2$ is Ser, Gly, Ala or Thr;

$Xaa_3$ is Asp or Glu;

$Xaa_5$ is Ala or Thr;

$Xaa_6$ is Ala, Phe, Tyr or naphthylalanine;

$Xaa_7$ is Thr or Ser;

$Xaa_8$ is Ala, Ser or Thr;

$Xaa_9$ is Asp or Glu;

$Xaa_{10}$ is Ala, Leu, Ile, Val, pentylglycine or Met;

$Xaa_{11}$ is Ala or Ser;

$Xaa_{12}$ is Ala or Lys;

$Xaa_{13}$ is Ala or Gln;

$Xaa_{14}$ is Ala, Leu, Ile, pentylglycine, Val or Met;

$Xaa_{15}$ is Ala or Glu;

$Xaa_{16}$ is Ala or Glu;

$Xaa_{17}$ is Ala or Glu;

$Xaa_{19}$ is Ala or Val;

$Xaa_{20}$ is Ala or Arg;

$Xaa_{21}$ is Ala or Leu;

$Xaa_{22}$ is Phe, Tyr or naphthylalanine;

$Xaa_{23}$ is Ile, Val, Leu, pentylglycine, tert-butylglycine or Met;

$Xaa_{24}$ is Ala, Glu or Asp;

$Xaa_{25}$ is Ala, Trp, Phe, Tyr or naphthylalanine;

$Xaa_{26}$ is Ala or Leu;

$Xaa_{27}$ is Ala or Lys;

$Xaa_{28}$ is Ala or Asn;

$Z_1$ is —OH,

—$NH_2$,

Gly -$Z_2$,

Gly Gly -$Z_2$

Gly Gly $Xaa_{31}$-$Z_2$,

Gly Gly $Xaa_{31}$ Ser-$Z_2$,

Gly Gly $Xaa_{31}$ Ser Ser-$Z_2$,

Gly Gly $Xaa_{31}$ Ser Ser Gly-$Z_2$,

Gly Gly $Xaa_{31}$ Ser Ser Gly Ala-$Z_2$,

Gly Gly $Xaa_{31}$ Ser Ser Gly Ala $Xaa_{36}$-$Z_2$,

Gly Gly $Xaa_{31}$ Ser Ser Gly Ala $Xaa_{36}$ $Xaa_{37}$-$Z_2$ or

Gly Gly $Xaa_{31}$ Ser Ser Gly Ala $Xaa_{36}$ $Xaa_{37}$ $Xaa_{38}$-$Z_2$;

wherein $Xaa_{31}$, $Xaa_{36}$, $Xaa_{37}$ and $Xaa_{38}$ are independently selected from the group consisting of Pro, homoproline, 3Hyp, 4Hyp, thioproline, N-alkylglycine, N-alkylpentylglycine and N-alkylalanine; and $Z_2$ is —OH or —$NH_2$;

provided that no more than three of $X_{aa3}$, $X_{aa5}$, $X_{aa6}$, $X_{aa8}$, $X_{aa10}$, $X_{aa11}$, $X_{aa12}$, $X_{aa13}$, $X_{aa14}$, $X_{aa15}$, $X_{aa16}$, $X_{aa17}$, $X_{aa19}$, $X_{aa20}$, $X_{aa21}$, $X_{aa24}$, $X_{aa25}$, $X_{aa26}$, $X_{aa27}$, and $X_{aa28}$ are Ala; and a pharmaceutically acceptable salt thereof.

2. The compound according to claim 1 wherein $X_{aa1}$ is His or Tyr.

3. The compound according to claim 2 wherein $X_{aa1}$ is His.

4. The compound according to claim 2 wherein $X_{aa2}$ is Gly.

5. The compound according to claim 4 wherein $X_{aa14}$ is Leu, pentylglycine or Met.

6. The compound according to claim 5 wherein $X_{aa25}$ is Trp or Phe.

7. The compound according to claim 6 wherein $X_{aa6}$ is Phe or naphthylalanine; and $X_{aa22}$ is Phe or naphthylalanine; $X_{aa23}$ is Ile or Val.

8. The compound according to claim 7 wherein $Z_1$ is —NH$_2$.

9. The compound according to claim 7 wherein $X_{aa31}$, $X_{aa36}$, $X_{aa37}$ and $X_{aa38}$ are independently selected from the group consisting of Pro, homoproline, thioproline and N-alkylalanine.

10. The compound according to claim 9 wherein $Z_2$ is —NH$_2$.

11. The compound according to claim 1 wherein $X_{aa2}$ is Gly.

12. The compound according to claim 1 wherein $X_{aa14}$ is Leu, pentylglycine or Met.

13. The compound according to claim 1 wherein $X_{aa25}$ is Trp or Phe.

14. The compound according to claim 1 wherein $X_{aa6}$ is Phe or naphthylalanine; $X_{aa22}$ is Phe or naphthylalanine; Xaa23 is Ile or Val.

15. The compound according to claim 1 wherein $Z_1$ is —NH$_2$.

16. The compound according to claim 1 wherein $X_{aa31}$, $X_{aa36}$, $X_{aa37}$ and $X_{aa38}$ are independently selected from the group consisting of Pro, homoproline, thioproline and N-alkylalanine.

17. The compound according to claim 1 wherein $Z_2$ is —NH$_2$.

18. The compound according to claim 1 which has an amino acid sequence selected from SEQ ID NOs: 5 to 65.

19. A method for the treatment of diabetes mellitus comprising the administration of a therapeutically effective amount of a compound according to claim 18.

20. The method of claim 19 further comprising the administration of a therapeutically effective amount of an insulin.

21. The method for the treatment of a hyperglycemic condition in a mammal comprising the step of administering a therapeutically effective amount of a compound according to claim 18.

22. A composition comprising the compound of claim 1 and a pharmaceutically acceptable carrier.

23. A method for the treatment of diabetes mellitus comprising the administration of a therapeutically effective amount of a compound according to claim 1.

24. The method of claim 23 further comprising the administration of a therapeutically effective amount of an insulin.

25. The method for the treatment of a hyperglycemic condition in a mammal comprising the step of administering a therapeutically effective amount of a compound according to claim 1.

26. A compound consists of

Xaa$_1$ Xaa$_2$ Xaa$_3$ Gly Xaa$_5$ Xaa$_6$ Xaa$_7$ Xaa$_8$ Xaa$_9$ Xaa$_{10}$

Xaa$_{11}$ Xaa$_{12}$ Xaa$_{13}$ Xaa$_{14}$ Xaa$_{15}$ Xaa$_{16}$ Xaa$_{17}$ Ala

Xaa$_{19}$ Xaa$_{20}$ Xaa$_{21}$ Xaa$_{22}$ Xaa$_{23}$ Xaa$_{24}$ Xaa$_{25}$ Xaa$_{26}$

Xaa$_{27}$ Xaa$_{28}$-Z$_1$;

Wherein

Xaa$_1$ is His or Arg;

Xaa$_2$ is Gly or Ala;

Xaa$_3$ is Asp or Glu;

Xaa$_5$ is Ala or Thr;

Xaa$_6$ is Ala, Phe, Tyr or naphthylalanine;

-continued

Xaa$_7$ is Thr or Ser;

Xaa$_8$ is Ala, Ser or Thr;

Xaa$_9$ is Asp or Glu;

Xaa$_{10}$ is Ala, Leu or pentylglycine;

Xaa$_{11}$ is Ala or Ser;

Xaa$_{12}$ is Ala or Lys;

Xaa$_{13}$ is Ala or Gln;

Xaa$_{14}$ is Ala, Leu, or pentylglycine;

Xaa$_{15}$ is Ala or Glu;

Xaa$_{16}$ is Ala or Glu;

Xaa$_{17}$ is Ala or Glu;

Xaa$_{19}$ is Ala or Val;

Xaa$_{20}$ is Ala or Arg;

Xaa$_{21}$ is Ala or Leu;

Xaa$_{22}$ is Phe or naphthylalanine;

Xaa$_{23}$ is Ile, Val or tert-butyl glycine;

Xaa$_{24}$ is Ala, Glu or Asp;

Xaa$_{25}$ is Ala, Trp or Phe;

Xaa$_{26}$ is Ala or Leu;

Xaa$_{27}$ is Ala or Lys;

Xaa$_{28}$ is Ala or Asn;

Z$_1$ is —OH,

—NH$_2$,

Gly-Z$_2$,

Gly Gly -Z$_2$,

Gly Gly Xaa$_{31}$-Z$_2$,

Gly Gly Xaa$_{31}$ Ser-Z$_2$,

Gly Gly Xaa$_{31}$ Ser Ser-Z$_2$,

Gly Gly Xaa$_{31}$ Ser Ser Gly-Z$_2$,

Gly Gly Xaa$_{31}$ Ser Ser Gly Ala-Z$_2$,

Gly Gly Xaa$_{31}$ Ser Ser Gly Ala Xaa$_{36}$-Z$_2$,

Gly Gly Xaa$_{31}$ Ser Ser Gly Ala Xaa$_{36}$ Xaa$_{37}$-Z$_2$ or

Gly Gly Xaa$_{31}$ Ser Ser Gly Ala Xaa$_{36}$ Xaa$_{37}$ Xaa$_{38}$-Z$_2$;

wherein

Xaa$_{31}$, Xaa$_{36}$, Xaa$_{37}$ and Xaa$_{38}$ are independently selected from the group consisting of Pro, homoproline, thioproline and N-alkylglycine; and Z$_2$ is —OH or —NH$_2$;

provided that no more than three of $X_{aa3}$, $X_{aa5}$, $X_{aa6}$, $X_{aa8}$, $X_{aa10}$, $X_{aa11}$, $X_{aa12}$, $X_{aa13}$, $X_{aa14}$, $X_{aa15}$, $X_{aa16}$, $X_{aa17}$, $X_{aa19}$, $X_{aa20}$, $X_{aa21}$, $X_{aa24}$, $X_{aa25}$, $X_{aa26}$, $X_{aa27}$, and $X_{aa28}$ are Ala; and a pharmaceutically acceptable salt thereof.

27. The compound according to claim 26 which has an amino acid sequences selected from SEQ ID NOs:7-19.

28. A method for the treatment of diabetes mellitus comprising the administration of a therapeutically effective amount of a compound according to claim 27.

29. The method of claim 28 further comprising the administration of a therapeutically effective amount of an insulin.

30. A composition comprising the compound of claim 26 and a pharmaceutically acceptable carrier.

31. A method for the treatment of diabetes mellitus comprising the administration of a therapeutically effective amount of a compound according to claim 26.

32. The method of claim 31 further comprising the administration of a therapeutically effective amount of an insulin.

33. A compound consists of

Xaa₁ Xaa₂ Xaa₃ Gly Xaa₅ Xaa₆ Xaa₇ Xaa₈ Xaa₉ Xaa₁₀

Xaa₁₁ Xaa₁₂ Xaa₁₃ Xaa₁₄ Xaa₁₅ Xaa₁₆ Xaa₁₇ Ala

Xaa₁₉ Xaa₂₀ Xaa₂₁ Xaa₂₂ Xaa₂₃ Xaa₂₄ Xaa₂₅ Xaa₂₆

$X_1$-$Z_1$; Wherein

Xaa₁ is His, Arg, Tyr or 4-imidazopropionyl;

Xaa₂ is Ser, Gly, Ala or Thr;

Xaa₃ is Asp or Glu;

Xaa₅ is Ala or Thr;

Xaa₆ is Ala, Phe, Tyr or naphthylalanine;

Xaa₇ is Thr or Ser;

Xaa₈ is Ala, Ser or Thr;

Xaa₉ is Asp or Glu;

Xaa₁₀ is Ala, Leu, Ile, Val, pentylglycine or Met;

Xaa₁₁ is Ala or Ser;

Xaa₁₂ is Ala or Lys;

Xaa₁₃ is Ala or Gln;

Xaa₁₄ is Ala, Leu, Ile, pentylglycine, Val or Met;

Xaa₁₅ is Ala or Glu;

Xaa₁₆ is Ala or Glu;

Xaa₁₇ is Ala or Glu;

Xaa₁₉ is Ala or Val;

Xaa₂₀ is Ala or Arg;

Xaa₂₁ is Ala, Leu or Lys-NHᵉ-R Asn, Asn Lys-NHᵉ-R; Lys-NHᵉ-R Ala; Ala Lys-NHᵉ-R wherein R is Lys, Arg, C₁-C₁₀ straight chain or branched alkanoyl or cycloalkylalkanoyl;

Xaa₂₂ is Phe, Tyr or naphthylalanine;

Xaa₂₃ is Ile, Val, Leu, pentylglycine or tert-butyl glycine;

Xaa₂₄ is Ala, Glu or Asp;

Xaa₂₅ is Ala, Trp, Phe, Tyr or naphthylalanine;

Xaa₂₆ is Ala or Leu;

-continued

X₁ is Lys Asn, Asn Lys, Lys-NHᵉ-R Asn, Asn Lys-NHᵉ-R, Lys-NHᵉ-R Ala, Ala Lys-NHᵉ-R wherein R is Lys, Arg, C₁-C₁₀ straight chain or branched alkanoyl or cycloalkylalkanoyl; and Z₁ is —OH,

—NH₂,

Gly-Z₂,

Gly Gly-Z₂

Gly Gly Xaa₃₁-Z₂,

Gly Gly Xaa₃₁ Ser-Z₂,

Gly Gly Xaa₃₁ Ser Ser-Z₂,

Gly Gly Xaa₃₁ Ser Ser Gly-Z₂,

Gly Gly Xaa₃₁ Ser Ser Gly Ala-Z₂,

Gly Gly Xaa₃₁ Ser Ser Gly Ala Xaa₃₆-Z₂,

Gly Gly Xaa₃₁ Ser Ser Gly Ala Xaa₃₆ Xaa₃₇-Z₂ or

Gly Gly Xaa₃₁ Ser Ser Gly Ala Xaa₃₆ Xaa₃₇ Xaa₃₈-Z₂;

wherein

Xaa₃₁, Xaa₃₆, Xaa₃₇ and Xaa₃₈ are independently selected from the group consisting of Pro, homoproline, 3Hyp, 4Hyp, thioproline, N-alkylglycine, N-alkylpentylglycine and N-alkylalanine; and Z₂ is —OH or —NH₂;

provided that no more than three of $X_{aa3}$, $X_{aa5}$, $X_{aa6}$, $X_{aa8}$, $X_{aa10}$, $X_{aa11}$, $X_{aa12}$, $X_{aa13}$, $X_{aa14}$, $X_{aa15}$, $X_{aa16}$, $X_{aa17}$, $X_{aa19}$, $X_{aa20}$, $X_{aa21}$, $X_{aa24}$, $X_{aa25}$, $X_{aa26}$, $X_{aa27}$, and $X_{aa28}$ are Ala; and a pharmaceutically acceptable salt thereof.

34. The compound according to claim 33 wherein $X_{aa1}$ is His, Tyr, or 4-imidazopropionyl.

35. The compound according to claim 34 wherein $X_{aa1}$ is His.

36. The compound according to claim 34 wherein $X_{aa1}$ is 4-imidazopropionyl.

37. The compound according to claim 33 wherein $X_{aa2}$ is Gly.

38. The compound according to claim 33 wherein $X_{aa14}$ is Leu, pentylglycine, or Met.

39. The compound according to claim 33 wherein $X_{aa25}$ is Trp or Phe.

40. The compound according to claim 33 wherein $X_{aa6}$ is Phe or naphthylalanine; $X_{aa22}$ is Phe or naphthylalanine; and $X_{aa23}$ is Ile or Val.

41. The compound according to claim 33 wherein $Z_1$ is —NH₂.

42. The compound according to claim 33 wherein $X_{aa31}$, $X_{aa36}$, $X_{aa37}$ and $X_{aa38}$ are independently selected from the group consisting of Pro, homoproline, thioproline, and N-alkylalanine.

43. The compound according to claim 33 wherein $Z_2$—NH₂.

44. The A compound according to claim 33 wherein $X_1$ is Lys Asn, Lys-NH$^\epsilon$—R Asn, or Lys-NH$^\epsilon$—R Ala wherein R is Lys, Arg, $C_1$-$C_{10}$ straight chain or branched alkanoyl.

45. The compound according to claim 33 wherein $X_{aa21}$ is Lys-NH$^\epsilon$—R where R is Lys, Arg, $C_1$-$C_{10}$ straight chain or branched alkanoyl or cycloalkylkanoyl.

46. A composition comprising the compound of claim 33 and a pharmaceutically acceptable carrier.

47. A compound comprising the acid sequence of SEQ ID NO:6, 67, 68, 69, 70, 71, 72, 73, or 74.

48. A composition comprising the compound of claim 47 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,696,161 B2 | Page 1 of 1 |
| APPLICATION NO. | : 11/807031 | |
| DATED | : April 13, 2010 | |
| INVENTOR(S) | : Nigel R. A. Beeley et al. | |

It is certified that error appears in the above-identified patent and that said Letters Patent is hereby corrected as shown below:

In Column 111, Claim 1, at line 17, replace "A compound consists of" with --A compound consisting of--.

In Column 113, Claim 26, at line 48, replace "A compound consists of" with --A compound consisting of--.

In Column 115, Claim 33, at line 17, replace "A compound consists of" with --A compound consisting of--.

In Column 116, Claim 43, at line 67, replace "Z2—NH2." with --Z2 is -NH2.--.

Signed and Sealed this

Eleventh Day of May, 2010

David J. Kappos
*Director of the United States Patent and Trademark Office*

SEQUENCE LISTING

<160> NUMBER OF SEQ ID NOS: 87

<210> SEQ ID NO 1
<211> LENGTH: 39
<212> TYPE: PRT
<213> ORGANISM: Heloderma horridum
<220> FEATURE:
<223> OTHER INFORMATION: C-term amidated

<400> SEQUENCE: 1

His Ser Asp Gly Thr Phe Thr Ser Asp Leu Ser Lys Gln Met Glu Glu
 1               5                   10                  15

Glu Ala Val Arg Leu Phe Ile Glu Trp Leu Lys Asn Gly Gly Pro Ser

```
                    20                  25                  30

Ser Gly Ala Pro Pro Ser
        35

<210> SEQ ID NO 2
<211> LENGTH: 39
<212> TYPE: PRT
<213> ORGANISM: Helodermasuspectum
<220> FEATURE:
<223> OTHER INFORMATION: C-term amidated

<400> SEQUENCE: 2

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
                20                  25                  30

Ser Gly Ala Pro Pro Ser
        35

<210> SEQ ID NO 3
<211> LENGTH: 30
<212> TYPE: PRT
<213> ORGANISM: Homo sapien
<220> FEATURE:
<223> OTHER INFORMATION: C-term amidated

<400> SEQUENCE: 3

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
                20                  25                  30

<210> SEQ ID NO 4
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: His, Arg or Tyr
<220> FEATURE:
<221> NAME/KEY: MOD_RES
<222> LOCATION: (2)
<223> OTHER INFORMATION: Ser, Gly, Ala or Thr
<220> FEATURE:
<221> NAME/KEY: MOD_RES
<222> LOCATION: (3)
<223> OTHER INFORMATION: Ala, Asp, or Glu
<220> FEATURE:
<221> NAME/KEY: MOD_RES
<222> LOCATION: (5)
<223> OTHER INFORMATION: Ala or Thr
<220> FEATURE:
<221> NAME/KEY: MOD_RES
<222> LOCATION: (6)
<223> OTHER INFORMATION: Ala, Phe, Tyr or naphthylalanine
<220> FEATURE:
<221> NAME/KEY: MOD_RES
<222> LOCATION: (7)
<223> OTHER INFORMATION: Thr or Ser
<220> FEATURE:
<221> NAME/KEY: MOD_RES
<222> LOCATION: (8)
<223> OTHER INFORMATION: Ala, Ser or Thr
<220> FEATURE:
<221> NAME/KEY: MOD_RES
<222> LOCATION: (9)
```

```
<223> OTHER INFORMATION: Asp or Glu
<220> FEATURE:
<221> NAME/KEY: MOD_RES
<222> LOCATION: (10)
<223> OTHER INFORMATION: Ala, Leu, Ile, Val, pentylglycine, or Met
<220> FEATURE:
<221> NAME/KEY: MOD_RES
<222> LOCATION: (11)
<223> OTHER INFORMATION: Ala or Ser
<220> FEATURE:
<221> NAME/KEY: MOD_RES
<222> LOCATION: (12)
<223> OTHER INFORMATION: Ala or Lys
<220> FEATURE:
<221> NAME/KEY: MOD_RES
<222> LOCATION: (13)
<223> OTHER INFORMATION: Ala or Gln
<220> FEATURE:
<221> NAME/KEY: MOD_RES
<222> LOCATION: (14)
<223> OTHER INFORMATION: Ala, Leu, Ile pentylglycine, Val, or Met
<220> FEATURE:
<221> NAME/KEY: MOD_RES
<222> LOCATION: (15)
<223> OTHER INFORMATION: Ala or Glu
<220> FEATURE:
<221> NAME/KEY: MOD_RES
<222> LOCATION: (16)
<223> OTHER INFORMATION: Ala or Glu
<220> FEATURE:
<221> NAME/KEY: MOD_RES
<222> LOCATION: (17)
<223> OTHER INFORMATION: Ala or Glu
<220> FEATURE:
<221> NAME/KEY: MOD_RES
<222> LOCATION: (19)
<223> OTHER INFORMATION: Ala or Val
<220> FEATURE:
<221> NAME/KEY: MOD_RES
<222> LOCATION: (20)
<223> OTHER INFORMATION: Ala or Arg
<220> FEATURE:
<221> NAME/KEY: MOD_RES
<222> LOCATION: (21)
<223> OTHER INFORMATION: Ala or Leu
<220> FEATURE:
<221> NAME/KEY: MOD_RES
<222> LOCATION: (22)
<223> OTHER INFORMATION: Phe, Tyr, or naphthylalanine
<220> FEATURE:
<221> NAME/KEY: MOD_RES
<222> LOCATION: (23)
<223> OTHER INFORMATION: Ile, Val, Leu, pentylglycine,
       tert-butylglycine, or Met
<220> FEATURE:
<221> NAME/KEY: MOD_RES
<222> LOCATION: (24)
<223> OTHER INFORMATION: Ala, Glu, or Asp
<220> FEATURE:
<221> NAME/KEY: MOD_RES
<222> LOCATION: (25)
<223> OTHER INFORMATION: Ala, Trp, Phe, Tyr, or naphthylalanine
<220> FEATURE:
<221> NAME/KEY: MOD_RES
<222> LOCATION: (26)
<223> OTHER INFORMATION: Ala or Leu
<220> FEATURE:
<221> NAME/KEY: MOD_RES
<222> LOCATION: (27)
<223> OTHER INFORMATION: Ala or Lys
<220> FEATURE:
<221> NAME/KEY: MOD_RES
<222> LOCATION: (28)
<223> OTHER INFORMATION: Ala or Asn
<220> FEATURE:
<221> NAME/KEY: MOD_RES
<222> LOCATION: (29)
<223> OTHER INFORMATION: Gly or not present
<220> FEATURE:
```

```
<221> NAME/KEY: MOD_RES
<222> LOCATION: (30)
<223> OTHER INFORMATION: Gly or not present
<220> FEATURE:
<221> NAME/KEY: MOD_RES
<222> LOCATION: (31)
<223> OTHER INFORMATION: Pro, homoproline, 3Hyp, 4Hyp, thioproline,
      N-alkylglycine, N-alkylpentylglycine,
      N-alkylalanine, or not present
<220> FEATURE:
<221> NAME/KEY: MOD_RES
<222> LOCATION: (32)
<223> OTHER INFORMATION: Ser or not present
<220> FEATURE:
<221> NAME/KEY: MOD_RES
<222> LOCATION: (33)
<223> OTHER INFORMATION: Ser or not present
<220> FEATURE:
<221> NAME/KEY: MOD_RES
<222> LOCATION: (34)
<223> OTHER INFORMATION: Gly or not present
<220> FEATURE:
<221> NAME/KEY: MOD_RES
<222> LOCATION: (35)
<223> OTHER INFORMATION: Ala or not present
<220> FEATURE:
<221> NAME/KEY: MOD_RES
<222> LOCATION: (36)
<223> OTHER INFORMATION: Pro, homoproline, 3Hyp, 4Hyp, thioproline,
      N-alkylglycine, N-alkylpentylglycine,
      N-alkylalanine, or not present
<220> FEATURE:
<221> NAME/KEY: MOD_RES
<222> LOCATION: (37)
<223> OTHER INFORMATION: Pro, homoproline, 3Hyp, 4Hyp, thioproline,
      N-alkylglycine, N-alkylpentylglycine,
      N-alkylalanine, or not present
<220> FEATURE:
<221> NAME/KEY: MOD_RES
<222> LOCATION: (38)
<223> OTHER INFORMATION: Pro, homoproline, 3Hyp, 4Hyp, thioproline,
      N-alkylglycine, N-alkylpentylglycine,
      N-alkylalanine, or not present
<220> FEATURE:
<223> OTHER INFORMATION: May be c-term amidated

<400> SEQUENCE: 4

Xaa Xaa Xaa Gly Xaa Xaa Xaa Xaa Xaa Xaa Xaa Xaa Xaa Xaa Xaa Xaa
 1               5                   10                  15

Xaa Ala Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa
        35

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 5

His Gly Glu Gly Thr Phe Thr Ser Asp Leu Ser Lys Gln Met Glu Glu
 1               5                   10                  15

Glu Ala Val Arg Leu Phe Ile Glu Trp Leu Lys Asn Gly Gly
            20                  25                  30

<210> SEQ ID NO 6
<211> LENGTH: 28
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 6

His Gly Glu Gly Thr Phe Thr Ser Asp Leu Ser Lys Gln Met Glu Glu
 1               5                  10                  15

Glu Ala Val Arg Leu Ala Ile Glu Phe Leu Lys Asn
            20                  25

<210> SEQ ID NO 7
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 7

His Gly Glu Gly Thr Phe Thr Ser Asp Leu Ser Lys Gln Leu Glu Glu
 1               5                  10                  15

Glu Ala Val Arg Leu Ala Ile Glu Phe Leu Lys Asn
            20                  25

<210> SEQ ID NO 8
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 8

His Ala Glu Gly Thr Phe Thr Ser Asp Leu Ser Lys Gln Leu Glu Glu
1                5                  10                  15

Glu Ala Val Arg Leu Phe Ile Glu Phe Leu Lys Asn
            20                  25

<210> SEQ ID NO 9
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 9

His Gly Glu Gly Ala Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 10
<211> LENGTH: 28
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<223> OTHER INFORMATION: May be c-term amidated

<400> SEQUENCE: 10

His Gly Glu Gly Thr Ala Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 11
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 11

His Gly Glu Gly Thr Phe Thr Ala Asp Leu Ser Lys Gln Leu Glu Glu
1               5                   10                  15

Glu Ala Val Arg Leu Phe Ile Glu Phe Leu Lys Asn
            20                  25

<210> SEQ ID NO 12
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 12

His Gly Glu Gly Thr Phe Thr Ser Asp Ala Ser Lys Gln Leu Glu Glu
1               5                   10                  15

Glu Ala Val Arg Leu Phe Ile Glu Phe Leu Lys Asn
            20                  25

<210> SEQ ID NO 13
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 13

His Gly Glu Gly Thr Phe Thr Ser Asp Leu Ala Lys Gln Leu Glu Glu
1               5                   10                  15

Glu Ala Val Arg Leu Phe Ile Glu Phe Leu Lys Asn
            20                  25

<210> SEQ ID NO 14
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:

<223> OTHER INFORMATION: May be c-term amidated

<400> SEQUENCE: 14

His Gly Glu Gly Thr Phe Thr Ser Asp Leu Ser Ala Gln Leu Glu Glu
 1               5                  10                  15

Glu Ala Val Arg Leu Phe Ile Glu Phe Leu Lys Asn
            20                  25

<210> SEQ ID NO 15
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 15

His Gly Glu Gly Thr Phe Thr Ser Asp Leu Ser Lys Ala Leu Glu Glu
 1               5                  10                  15

Glu Ala Val Arg Leu Phe Ile Glu Phe Leu Lys Asn
            20                  25

<210> SEQ ID NO 16
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 16

His Gly Glu Gly Thr Phe Thr Ser Asp Leu Ser Lys Gln Ala Glu Glu
 1               5                  10                  15

Glu Ala Val Arg Leu Phe Ile Glu Phe Leu Lys Asn
            20                  25

<210> SEQ ID NO 17
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 17

His Gly Glu Gly Thr Phe Thr Ser Asp Leu Ser Lys Gln Leu Ala Glu
 1               5                  10                  15

Glu Ala Val Arg Leu Phe Ile Glu Phe Leu Lys Asn
            20                  25

<210> SEQ ID NO 18
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 18

His Gly Glu Gly Thr Phe Thr Ser Asp Leu Ser Lys Gln Leu Glu Ala
1               5                   10                  15

Glu Ala Val Arg Leu Phe Ile Glu Phe Leu Lys Asn
            20                  25

<210> SEQ ID NO 19
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 19

His Gly Glu Gly Thr Phe Thr Ser Asp Leu Ser Lys Gln Leu Glu Glu
1               5                   10                  15

Ala Ala Val Arg Leu Phe Ile Glu Phe Leu Lys Asn
            20                  25

<210> SEQ ID NO 20
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 20

His Gly Glu Gly Thr Phe Thr Ser Asp Leu Ser Lys Gln Leu Glu Glu
1               5                   10                  15

Glu Ala Ala Arg Leu Phe Ile Glu Phe Leu Lys Asn
            20                  25

<210> SEQ ID NO 21
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 21

His Gly Glu Gly Thr Phe Thr Ser Asp Leu Ser Lys Gln Leu Glu Glu
1               5                   10                  15

Glu Ala Val Ala Leu Phe Ile Glu Phe Leu Lys Asn
            20                  25

<210> SEQ ID NO 22
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 22

His Gly Glu Gly Thr Phe Thr Ser Asp Leu Ser Lys Gln Leu Glu Glu
1               5                   10                  15

Glu Ala Val Arg Ala Phe Ile Glu Phe Leu Lys Asn
            20                  25

<210> SEQ ID NO 23
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 23

His Gly Glu Gly Thr Phe Thr Ser Asp Leu Ser Lys Gln Leu Glu Glu
 1               5                  10                  15

Glu Ala Val Arg Leu Phe Ile Ala Phe Leu Lys Asn
            20                  25

<210> SEQ ID NO 24
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 24

His Gly Glu Gly Thr Phe Thr Ser Asp Leu Ser Lys Gln Leu Glu Glu
 1               5                  10                  15

Glu Ala Val Arg Leu Phe Ile Glu Ala Leu Lys Asn
            20                  25

<210> SEQ ID NO 25
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 25

His Gly Glu Gly Thr Phe Thr Ser Asp Leu Ser Lys Gln Leu Glu Glu
 1               5                  10                  15

Glu Ala Val Arg Leu Phe Ile Glu Phe Ala Lys Asn
            20                  25

<210> SEQ ID NO 26
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 26

His Gly Glu Gly Thr Phe Thr Ser Asp Leu Ser Lys Gln Leu Glu Glu
 1               5                  10                  15

Glu Ala Val Arg Leu Phe Ile Glu Phe Leu Ala Asn
            20                  25

```
<210> SEQ ID NO 27
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 27

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Ala
            20                  25

<210> SEQ ID NO 28
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 28

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro
        35

<210> SEQ ID NO 29
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 29

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro Pro
        35

<210> SEQ ID NO 30
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 30

His Gly Glu Gly Thr Phe Thr Ser Asp Leu Ser Lys Gln Met Glu Glu
 1               5                  10                  15
```

```
Glu Ala Val Arg Leu Phe Ile Glu Trp Leu Lys Asn Gly Gly Pro Ser
            20                  25                  30

Ser Gly Ala Pro Pro
        35

<210> SEQ ID NO 31
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 31

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro
        35

<210> SEQ ID NO 32
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 32

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro
        35

<210> SEQ ID NO 33
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 33

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro
        35

<210> SEQ ID NO 34
<211> LENGTH: 35
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: May be c-term amidated

<400> SEQUENCE: 34

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala
        35

<210> SEQ ID NO 35
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 35

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala
        35

<210> SEQ ID NO 36
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 36

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly

<210> SEQ ID NO 37
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 37

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly
```

```
<210> SEQ ID NO 38
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 38

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser

<210> SEQ ID NO 39
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 39

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser

<210> SEQ ID NO 40
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 40

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

<210> SEQ ID NO 41
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 41

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
```

```
<210> SEQ ID NO 42
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 42

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro
            20                  25                  30

<210> SEQ ID NO 43
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 43

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro
            20                  25                  30

<210> SEQ ID NO 44
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 44

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly
            20                  25                  30

<210> SEQ ID NO 45
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 45

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly
            20                  25
```

```
<210> SEQ ID NO 46
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 46

His Gly Glu Gly Thr Phe Thr Ser Asp Leu Ser Lys Gln Leu Glu Glu
  1               5                  10                  15

Glu Ala Val Arg Leu Phe Ile Glu Phe Leu Lys Asn Gly
             20                  25

<210> SEQ ID NO 47
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)
<223> OTHER INFORMATION: thioproline
<220> FEATURE:
<221> NAME/KEY: MOD_RES
<222> LOCATION: (36)..(38)
<223> OTHER INFORMATION: thioproline
<220> FEATURE:
<223> OTHER INFORMATION: May be c-term amidated

<400> SEQUENCE: 47

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Xaa Ser
             20                  25                  30

Ser Gly Ala Xaa Xaa Xaa
         35

<210> SEQ ID NO 48
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (36)..(38)
<223> OTHER INFORMATION: thioproline
<220> FEATURE:
<223> OTHER INFORMATION: May be c-term amidated

<400> SEQUENCE: 48

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala Xaa Xaa Xaa
         35

<210> SEQ ID NO 49
<211> LENGTH: 37
<212> TYPE: PRT
<213> ORGANISM: Artificial Sequence
```

<220> FEATURE:
<223> OTHER INFORMATION: Description of Artificial Sequence: Synthetic
      peptide
<220> FEATURE:
<221> NAME/KEY: MOD_RES
<222> LOCATION: (31)
<223> OTHER INFORMATION: N-methylalanine
<220> FEATURE:
<223> OTHER INFORMATION: May be c-term amidated

<400> SEQUENCE: 49

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
             20                  25                  30

Ser Gly Ala Pro Pro
         35

<210> SEQ ID NO 50
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)
<223> OTHER INFORMATION: N-methylalanine
<220> FEATURE:
<221> NAME/KEY: MOD_RES
<222> LOCATION: (36)..(37)
<223> OTHER INFORMATION: N-methylalanine
<220> FEATURE:
<223> OTHER INFORMATION: May be c-term amidated

<400> SEQUENCE: 50

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
             20                  25                  30

Ser Gly Ala Xaa Xaa
         35

<210> SEQ ID NO 51
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)
<223> OTHER INFORMATION: homoproline
<220> FEATURE:
<221> NAME/KEY: MOD_RES
<222> LOCATION: (36)..(37)
<223> OTHER INFORMATION: homoproline
<220> FEATURE:
<223> OTHER INFORMATION: May be c-term amidated

<400> SEQUENCE: 51

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
             20                  25                  30

Ser Gly Ala Xaa Xaa

-continued

35

<210> SEQ ID NO 52
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)
<223> OTHER INFORMATION: homoproline
<220> FEATURE:
<221> NAME/KEY: MOD_RES
<222> LOCATION: (36)
<223> OTHER INFORMATION: homoproline
<220> FEATURE:
<223> OTHER INFORMATION: May be c-term amidated

<400> SEQUENCE: 52

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Xaa Ser
             20                  25                  30

Ser Gly Ala Xaa
          35

<210> SEQ ID NO 53
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 53

Arg Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala
          35

<210> SEQ ID NO 54
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 54

His Gly Asp Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly
             20                  25                  30

<210> SEQ ID NO 55
<211> LENGTH: 28
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: napthylalanine
<220> FEATURE:
<223> OTHER INFORMATION: May be c-term amidated

<400> SEQUENCE: 55

His Gly Glu Gly Thr Xaa Thr Ser Asp Leu Ser Lys Gln Leu Glu Glu
  1               5                  10                  15

Glu Ala Val Arg Leu Phe Ile Glu Phe Leu Lys Asn
             20                  25

<210> SEQ ID NO 56
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 56

His Gly Glu Gly Thr Phe Ser Ser Asp Leu Ser Lys Gln Met Glu Glu
  1               5                  10                  15

Glu Ala Val Arg Leu Phe Ile Glu Trp Leu Lys Asn
             20                  25

<210> SEQ ID NO 57
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 57

His Gly Glu Gly Thr Phe Ser Thr Asp Leu Ser Lys Gln Met Glu Glu
  1               5                  10                  15

Glu Ala Val Arg Leu Phe Ile Glu Trp Leu Lys Asn
             20                  25

<210> SEQ ID NO 58
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 58

His Gly Glu Gly Thr Phe Thr Ser Glu Leu Ser Lys Gln Met Ala Glu
  1               5                  10                  15

Glu Ala Val Arg Leu Phe Ile Glu Trp Leu Lys Asn
             20                  25

<210> SEQ ID NO 59
<211> LENGTH: 28
<212> TYPE: PRT
<213> ORGANISM: Artificial Sequence
```

-continued

```
<220> FEATURE:
<223> OTHER INFORMATION: Description of Artificial Sequence: Synthetic
      peptide
<220> FEATURE:
<221> NAME/KEY: MOD_RES
<222> LOCATION: (10)
<223> OTHER INFORMATION: pentylglycine
<220> FEATURE:
<223> OTHER INFORMATION: May be c-term amidated

<400> SEQUENCE: 59

His Gly Glu Gly Thr Phe Thr Ser Asp Xaa Ser Lys Gln Leu Glu Glu
 1               5                  10                  15

Glu Ala Val Arg Leu Phe Ile Glu Phe Leu Lys Asn
            20                  25

<210> SEQ ID NO 60
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)
<223> OTHER INFORMATION: napthylalanine
<220> FEATURE:
<223> OTHER INFORMATION: May be c-term amidated

<400> SEQUENCE: 60

His Gly Glu Gly Thr Phe Thr Ser Asp Leu Ser Lys Gln Leu Glu Glu
 1               5                  10                  15

Glu Ala Val Arg Leu Xaa Ile Glu Phe Leu Lys Asn
            20                  25

<210> SEQ ID NO 61
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)
<223> OTHER INFORMATION: tertiary-butylglycine
<220> FEATURE:
<223> OTHER INFORMATION: May be c-term amidated

<400> SEQUENCE: 61

His Gly Glu Gly Thr Phe Thr Ser Asp Leu Ser Lys Gln Met Glu Glu
 1               5                  10                  15

Glu Ala Val Arg Leu Phe Xaa Glu Trp Leu Lys Asn
            20                  25

<210> SEQ ID NO 62
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 62

His Gly Glu Gly Thr Phe Thr Ser Asp Leu Ser Lys Gln Leu Glu Glu
 1               5                  10                  15
```

```
Glu Ala Val Arg Leu Phe Ile Asp Phe Leu Lys Asn
            20                  25
```

<210> SEQ ID NO 63
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 63

```
His Gly Glu Gly Thr Phe Thr Ser Asp Ala Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser
```

<210> SEQ ID NO 64
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May be c-term amidated

<400> SEQUENCE: 64

```
His Gly Glu Gly Thr Phe Thr Ser Asp Ala Ser Lys Gln Met Glu Glu
 1               5                  10                  15

Glu Ala Val Arg Leu Phe Ile Glu Trp Leu Lys Asn Gly
            20                  25
```

<210> SEQ ID NO 65
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)
<223> OTHER INFORMATION: homoproline
<220> FEATURE:
<221> NAME/KEY: MOD_RES
<222> LOCATION: (36)..(37)
<223> OTHER INFORMATION: homoproline
<220> FEATURE:
<223> OTHER INFORMATION: May be c-term amidated

<400> SEQUENCE: 65

```
His Gly Glu Gly Thr Phe Thr Ser Asp Ala Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Xaa Xaa
        35
```

<210> SEQ ID NO 66
<211> LENGTH: 40
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: His, Arg, Tyr, or 4-imidazopropionyl
<220> FEATURE:
<221> NAME/KEY: MOD_RES
<222> LOCATION: (2)
<223> OTHER INFORMATION: Ser, Gly, Ala, or Thr
<220> FEATURE:
<221> NAME/KEY: MOD_RES
<222> LOCATION: (3)
<223> OTHER INFORMATION: Ala, Asp, or Glu
<220> FEATURE:
<221> NAME/KEY: MOD_RES
<222> LOCATION: (5)
<223> OTHER INFORMATION: Ala or Thr
<220> FEATURE:
<221> NAME/KEY: MOD_RES
<222> LOCATION: (6)
<223> OTHER INFORMATION: Ala, Phe, Tyr, or naphthylalanine
<220> FEATURE:
<221> NAME/KEY: MOD_RES
<222> LOCATION: (7)
<223> OTHER INFORMATION: Thr or Ser
<220> FEATURE:
<221> NAME/KEY: MOD_RES
<222> LOCATION: (8)
<223> OTHER INFORMATION: Ala, Ser, or Thr
<220> FEATURE:
<221> NAME/KEY: MOD_RES
<222> LOCATION: (9)
<223> OTHER INFORMATION: Asp or Glu
<220> FEATURE:
<221> NAME/KEY: MOD_RES
<222> LOCATION: (10)
<223> OTHER INFORMATION: Ala, Leu, Ile, Val, pentylglycine, or Met
<220> FEATURE:
<221> NAME/KEY: MOD_RES
<222> LOCATION: (11)
<223> OTHER INFORMATION: Ala or Ser
<220> FEATURE:
<221> NAME/KEY: MOD_RES
<222> LOCATION: (12)
<223> OTHER INFORMATION: Ala or Lys
<220> FEATURE:
<221> NAME/KEY: MOD_RES
<222> LOCATION: (13)
<223> OTHER INFORMATION: Ala or Gln
<220> FEATURE:
<221> NAME/KEY: MOD_RES
<222> LOCATION: (14)
<223> OTHER INFORMATION: Ala, Leu, Ile, pentylglycine, Val, or Met
<220> FEATURE:
<221> NAME/KEY: MOD_RES
<222> LOCATION: (15)
<223> OTHER INFORMATION: Ala or Glu
<220> FEATURE:
<221> NAME/KEY: MOD_RES
<222> LOCATION: (16)
<223> OTHER INFORMATION: Ala or Glu
<220> FEATURE:
<221> NAME/KEY: MOD_RES
<222> LOCATION: (17)
<223> OTHER INFORMATION: Ala or Glu
<220> FEATURE:
<221> NAME/KEY: MOD_RES
<222> LOCATION: (19)
<223> OTHER INFORMATION: Ala or Val
<220> FEATURE:
<221> NAME/KEY: MOD_RES
<222> LOCATION: (20)
<223> OTHER INFORMATION: Ala or Arg
<220> FEATURE:
<221> NAME/KEY: MOD_RES
<222> LOCATION: (21)
<223> OTHER INFORMATION: Ala, Leu, or Lys-NH
```

```
<220> FEATURE:
<221> NAME/KEY: MOD_RES
<222> LOCATION: (22)
<223> OTHER INFORMATION: Lys, Arg, or not present
<220> FEATURE:
<221> NAME/KEY: MOD_RES
<222> LOCATION: (23)
<223> OTHER INFORMATION: Phe, Tyr, or naphthylalanine
<220> FEATURE:
<221> NAME/KEY: MOD_RES
<222> LOCATION: (24)
<223> OTHER INFORMATION: Ile, Val, Leu, pentylglycine,
      tert-butylglycine, or Met
<220> FEATURE:
<221> NAME/KEY: MOD_RES
<222> LOCATION: (25)
<223> OTHER INFORMATION: Ala, Glu, or Asp
<220> FEATURE:
<221> NAME/KEY: MOD_RES
<222> LOCATION: (26)
<223> OTHER INFORMATION: Ala, Trp, Phe, Tyr, or naphthylalanine
<220> FEATURE:
<221> NAME/KEY: MOD_RES
<222> LOCATION: (27)
<223> OTHER INFORMATION: Ala or Leu
<220> FEATURE:
<221> NAME/KEY: MOD_RES
<222> LOCATION: (28)
<223> OTHER INFORMATION: Lys, Asn, Lys-NH, or Ala
<220> FEATURE:
<221> NAME/KEY: MOD_RES
<222> LOCATION: (29)
<223> OTHER INFORMATION: Asn, Lys, Arg, or Lys-NH
<220> FEATURE:
<221> NAME/KEY: MOD_RES
<222> LOCATION: (30)
<223> OTHER INFORMATION: Asn, Lys, Arg, Ala, or not present
<220> FEATURE:
<221> NAME/KEY: MOD_RES
<222> LOCATION: (31)
<223> OTHER INFORMATION: Gly or not present
<220> FEATURE:
<221> NAME/KEY: MOD_RES
<222> LOCATION: (32)
<223> OTHER INFORMATION: Gly or not present
<220> FEATURE:
<221> NAME/KEY: MOD_RES
<222> LOCATION: (33)
<223> OTHER INFORMATION: Pro, homoproline, 3Hyp, 4Hyp, thioproline,
      N-alkylglycine, N-alkylpentylglycine,
      N-alkylalanine, or not present
<220> FEATURE:
<221> NAME/KEY: MOD_RES
<222> LOCATION: (34)
<223> OTHER INFORMATION: Ser or not present
<220> FEATURE:
<221> NAME/KEY: MOD_RES
<222> LOCATION: (35)
<223> OTHER INFORMATION: Ser or not present
<220> FEATURE:
<221> NAME/KEY: MOD_RES
<222> LOCATION: (36)
<223> OTHER INFORMATION: Gly or not present
<220> FEATURE:
<221> NAME/KEY: MOD_RES
<222> LOCATION: (37)
<223> OTHER INFORMATION: Ala or not present
<220> FEATURE:
<221> NAME/KEY: MOD_RES
<222> LOCATION: (38)
<223> OTHER INFORMATION: Pro, homoproline, 3Hyp, 4Hyp, thioproline,
      N-alkylglycine, N-alkylpentylglycine,
      N-alkylalanine, or not present
<220> FEATURE:
<221> NAME/KEY: MOD_RES
<222> LOCATION: (39)
<223> OTHER INFORMATION: Pro, homoproline, 3Hyp, 4Hyp, thioproline,
      N-alkylglycine, N-alkylpentylglycine,
      N-alkylalanine, or not present
```

```
<220> FEATURE:
<221> NAME/KEY: MOD_RES
<222> LOCATION: (40)
<223> OTHER INFORMATION: Pro, homoproline, 3Hyp, 4Hyp, thioproline,
      N-alkylglycine, N-alkylpentylglycine,
      N-alkylalanine, or not present
<220> FEATURE:
<223> OTHER INFORMATION: May be c-term amidated

<400> SEQUENCE: 66

Xaa Xaa Xaa Gly Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa
            35                  40

<210> SEQ ID NO 67
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 4-imidazolylpropionyl-Gly
<220> FEATURE:
<221> NAME/KEY: MOD_RES
<222> LOCATION: (26)
<223> OTHER INFORMATION: Lys-NH-octanoyl
<220> FEATURE:
<223> OTHER INFORMATION: May be c-term amidated

<400> SEQUENCE: 67

Xaa Glu Gly Thr Phe Thr Ser Asp Leu Ser Lys Gln Met Glu Glu
1               5                   10                  15

Glu Ala Val Arg Leu Phe Ile Glu Trp Leu Xaa Asn
            20                  25

<210> SEQ ID NO 68
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 4-imidazolylpropionyl-Gly
<220> FEATURE:
<221> NAME/KEY: MOD_RES
<222> LOCATION: (26)
<223> OTHER INFORMATION: Lys-NH-octanoyl
<220> FEATURE:
<223> OTHER INFORMATION: May be c-term amidated

<400> SEQUENCE: 68

Xaa Glu Gly Thr Phe Thr Ser Asp Leu Ser Lys Gln Leu Glu Glu
1               5                   10                  15

Glu Ala Val Arg Leu Phe Ile Glu Phe Leu Xaa Asn
            20                  25

<210> SEQ ID NO 69
<211> LENGTH: 29
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 4-imidazolylpropionyl-Gly
<220> FEATURE:
<221> NAME/KEY: MOD_RES
<222> LOCATION: (26)
<223> OTHER INFORMATION: Lys-NH-octanoyl
<220> FEATURE:
<223> OTHER INFORMATION: May be c-term amidated

<400> SEQUENCE: 69

Xaa Glu Gly Thr Phe Thr Ser Asp Leu Ser Lys Gln Met Glu Glu
 1               5                  10                  15

Glu Ala Val Arg Leu Phe Ile Glu Trp Leu Xaa Asn Gly Gly
                20                  25

<210> SEQ ID NO 70
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 4-imidazolylpropionyl-Gly
<220> FEATURE:
<221> NAME/KEY: MOD_RES
<222> LOCATION: (26)
<223> OTHER INFORMATION: Lys-NH-octanoyl
<220> FEATURE:
<223> OTHER INFORMATION: May be c-term amidated

<400> SEQUENCE: 70

Xaa Glu Gly Thr Phe Thr Ser Asp Leu Ser Lys Gln Leu Glu Glu
 1               5                  10                  15

Glu Ala Val Arg Leu Phe Ile Glu Phe Leu Xaa Asn Gly Gly
                20                  25

<210> SEQ ID NO 71
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 4-imidazolylpropionyl-Gly
<220> FEATURE:
<221> NAME/KEY: MOD_RES
<222> LOCATION: (27)
<223> OTHER INFORMATION: Lys-NH-octanoyl
<220> FEATURE:
<223> OTHER INFORMATION: May be c-term amidated

<400> SEQUENCE: 71

Xaa Glu Gly Thr Phe Thr Ser Asp Leu Ser Lys Gln Met Glu Glu
 1               5                  10                  15

Glu Ala Val Arg Leu Phe Ile Glu Trp Leu Asn Xaa
                20                  25

<210> SEQ ID NO 72
<211> LENGTH: 27
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 4-imidazolylpropionyl-Gly
<220> FEATURE:
<221> NAME/KEY: MOD_RES
<222> LOCATION: (27)
<223> OTHER INFORMATION: Lys-NH-octanoyl
<220> FEATURE:
<223> OTHER INFORMATION: May be c-term amidated

<400> SEQUENCE: 72

Xaa Glu Gly Thr Phe Thr Ser Asp Leu Ser Lys Gln Leu Glu Glu
 1               5                  10                  15

Glu Ala Val Arg Leu Phe Ile Glu Phe Leu Asn Xaa
                20                  25

<210> SEQ ID NO 73
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 4-imidazolylpropionyl-Gly
<220> FEATURE:
<221> NAME/KEY: MOD_RES
<222> LOCATION: (27)
<223> OTHER INFORMATION: Lys-NH-octanoyl
<220> FEATURE:
<223> OTHER INFORMATION: May be c-term amidated

<400> SEQUENCE: 73

Xaa Glu Gly Thr Phe Thr Ser Asp Leu Ser Lys Gln Met Glu Glu
 1               5                  10                  15

Glu Ala Val Arg Leu Phe Ile Glu Trp Leu Asn Xaa Gly Gly
                20                  25

<210> SEQ ID NO 74
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 4-imidazolylpropionyl-Gly
<220> FEATURE:
<221> NAME/KEY: MOD_RES
<222> LOCATION: (27)
<223> OTHER INFORMATION: Lys-NH-octanoyl
<220> FEATURE:
<223> OTHER INFORMATION: May be c-term amidated

<400> SEQUENCE: 74

Xaa Glu Gly Thr Phe Thr Ser Asp Leu Ser Lys Gln Leu Glu Glu
 1               5                  10                  15

Glu Ala Val Arg Leu Phe Ile Glu Phe Leu Asn Xaa Gly Gly
                20                  25
```

```
<210> SEQ ID NO 75
<211> LENGTH: 5
<212> TYPE: PRT
<213> ORGANISM: Artificial Sequence
<220> FEATURE:
<221> NAME/KEY: MOD_RES
<222> LOCATION: (3)
<223> OTHER INFORMATION: Pro, homoproline, 3Hyp, 4Hyp, thioproline,
      N-Alkylglycine, N-alkylpentylglycine,
      or N-alklalanine
<220> FEATURE:
<223> OTHER INFORMATION: May be c-term amidated

<400> SEQUENCE: 75

Gly Gly Xaa Ser Ser
 1               5

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, 3Hyp, 4Hyp, thioproline,
      N-Alkylglycine, N-alkylpentylglycine,
      or N-alklalanine
<220> FEATURE:
<223> OTHER INFORMATION: May be c-term amidated

<400> SEQUENCE: 76

Gly Gly Xaa Ser Ser Gly
 1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, 3Hyp, 4Hyp, thioproline,
      N-Alkylglycine, N-alkylpentylglycine,
      or N-alklalanine
<220> FEATURE:
<223> OTHER INFORMATION: May be c-term amidated

<400> SEQUENCE: 77

Gly Gly Xaa Ser Ser Gly Ala
 1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, 3Hyp, 4Hyp, thioproline,
      N-Alkylglycine, N-alkylpentylglycine,
      or N-alklalanine
<220> FEATURE:
<221> NAME/KEY: MOD_RES
<222> LOCATION: (8)
```

```
<223> OTHER INFORMATION: Pro, homoproline, 3Hyp, 4Hyp, thioproline,
      N-alkylglycine, N-alkylpentylglycine,
      or N-alkylalanine
<220> FEATURE:
<223> OTHER INFORMATION: May be c-term amidated

<400> SEQUENCE: 78

Gly Gly Xaa Ser Ser Gly Ala Xaa
  1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, 3Hyp, 4Hyp, thioproline,
      N-Alkylglycine, N-alkylpentylglycine,
      or N-alklalanine
<220> FEATURE:
<221> NAME/KEY: MOD_RES
<222> LOCATION: (8)
<223> OTHER INFORMATION: Pro, homoproline, 3Hyp, 4Hyp, thioproline,
      N-alkylglycine, N-alkylpentylglycine,
      or N-alkylalanine
<220> FEATURE:
<221> NAME/KEY: MOD_RES
<222> LOCATION: (9)
<223> OTHER INFORMATION: Pro, homoproline, 3Hyp, 4Hyp, thioproline,
      N-alkylglycine, N-alkylpentylglycine,
      or N-alkylalanine
<220> FEATURE:
<223> OTHER INFORMATION: May be c-term amidated

<400> SEQUENCE: 79

Gly Gly Xaa Ser Ser Gly Ala Xaa Xaa
  1               5

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, 3Hyp, 4Hyp, thioproline,
      N-Alkylglycine, N-alkylpentylglycine,
      or N-alklalanine
<220> FEATURE:
<221> NAME/KEY: MOD_RES
<222> LOCATION: (8)
<223> OTHER INFORMATION: Pro, homoproline, 3Hyp, 4Hyp, thioproline,
      N-alkylglycine, N-alkylpentylglycine,
      or N-alkylalanine
<220> FEATURE:
<221> NAME/KEY: MOD_RES
<222> LOCATION: (9)
<223> OTHER INFORMATION: Pro, homoproline, 3Hyp, 4Hyp, thioproline,
      N-alkylglycine, N-alkylpentylglycine,
      or N-alkylalanine
<220> FEATURE:
<221> NAME/KEY: MOD_RES
<222> LOCATION: (10)
<223> OTHER INFORMATION: Pro, homoproline, 3Hyp, 4Hyp, thioproline,
      N-alkylglycine, N-alkylpentylglycine,
      or N-alkylalanine
<220> FEATURE:
<223> OTHER INFORMATION: May be c-term amidated
```

```
<400> SEQUENCE: 80

Gly Gly Xaa Ser Ser Gly Ala Xaa Xaa Xaa
 1               5                  10

<210> SEQ ID NO 81
<211> LENGTH: 5
<212> TYPE: PRT
<213> ORGANISM: Artificial Sequence
<220> FEATURE:
<221> NAME/KEY: MOD_RES
<222> LOCATION: (3)
<223> OTHER INFORMATION: Pro, homoproline, thioproline,
      or N-methylalanine
<220> FEATURE:
<223> OTHER INFORMATION: May be c-term amidated

<400> SEQUENCE: 81

Gly Gly Xaa Ser Ser
 1               5

<210> SEQ ID NO 82
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, thioproline,
      or N-methylalanine
<220> FEATURE:
<223> OTHER INFORMATION: May be c-term amidated

<400> SEQUENCE: 82

Gly Gly Xaa Ser Ser Gly
 1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, thioproline,
      or N-methylalanine
<220> FEATURE:
<223> OTHER INFORMATION: May be c-term amidated

<400> SEQUENCE: 83

Gly Gly Xaa Ser Ser Gly Ala
 1               5

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, thioproline,
      or N-methylalanine
```

```
<220> FEATURE:
<221> NAME/KEY: MOD_RES
<222> LOCATION: (8)
<223> OTHER INFORMATION: Pro, homoproline, thioproline,
      or N-methylalanine
<220> FEATURE:
<223> OTHER INFORMATION: May be c-term amidated

<400> SEQUENCE: 84

Gly Gly Xaa Ser Ser Gly Ala Xaa
 1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, thioproline,
      or N-methylalanine
<220> FEATURE:
<221> NAME/KEY: MOD_RES
<222> LOCATION: (8)
<223> OTHER INFORMATION: Pro, homoproline, thioproline,
      or N-methylalanine
<220> FEATURE:
<221> NAME/KEY: MOD_RES
<222> LOCATION: (9)
<223> OTHER INFORMATION: Pro, homoproline, thioproline,
      or N-methylalanine
<220> FEATURE:
<223> OTHER INFORMATION: May be c-term amidated

<400> SEQUENCE: 85

Gly Gly Xaa Ser Ser Gly Ala Xaa Xaa
 1               5

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, thioproline,
      or N-methylalanine
<220> FEATURE:
<221> NAME/KEY: MOD_RES
<222> LOCATION: (8)
<223> OTHER INFORMATION: Pro, homoproline, thioproline,
      or N-methylalanine
<220> FEATURE:
<221> NAME/KEY: MOD_RES
<222> LOCATION: (9)
<223> OTHER INFORMATION: Pro, homoproline, thioproline,
      or N-methylalanine
<220> FEATURE:
<221> NAME/KEY: MOD_RES
<222> LOCATION: (10)
<223> OTHER INFORMATION: Pro, homoproline, thioproline,
      or N-methylalanine
<220> FEATURE:
<223> OTHER INFORMATION: May be c-term amidated

<400> SEQUENCE: 86

Gly Gly Xaa Ser Ser Gly Ala Xaa Xaa Xaa
 1               5                  10
```

```
<210> SEQ ID NO 87
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: His, Arg or Tyr
<220> FEATURE:
<221> NAME/KEY: MOD_RES
<222> LOCATION: (2)
<223> OTHER INFORMATION: Ser, Gly, Ala or Thr
<220> FEATURE:
<221> NAME/KEY: MOD_RES
<222> LOCATION: (3)
<223> OTHER INFORMATION: Ala, Asp, or Glu
<220> FEATURE:
<221> NAME/KEY: MOD_RES
<222> LOCATION: (5)
<223> OTHER INFORMATION: Ala or Thr
<220> FEATURE:
<221> NAME/KEY: MOD_RES
<222> LOCATION: (6)
<223> OTHER INFORMATION: Ala, Phe, Tyr or naphthylalanine
<220> FEATURE:
<221> NAME/KEY: MOD_RES
<222> LOCATION: (7)
<223> OTHER INFORMATION: Thr or Ser
<220> FEATURE:
<221> NAME/KEY: MOD_RES
<222> LOCATION: (8)
<223> OTHER INFORMATION: Ala, Ser or Thr
<220> FEATURE:
<221> NAME/KEY: MOD_RES
<222> LOCATION: (9)
<223> OTHER INFORMATION: Asp or Glu
<220> FEATURE:
<221> NAME/KEY: MOD_RES
<222> LOCATION: (10)
<223> OTHER INFORMATION: Ala, Leu, Ile, Val, pentylglycine, or Met
<220> FEATURE:
<221> NAME/KEY: MOD_RES
<222> LOCATION: (11)
<223> OTHER INFORMATION: Ala or Ser
<220> FEATURE:
<221> NAME/KEY: MOD_RES
<222> LOCATION: (12)
<223> OTHER INFORMATION: Ala or Lys
<220> FEATURE:
<221> NAME/KEY: MOD_RES
<222> LOCATION: (13)
<223> OTHER INFORMATION: Ala or Gln
<220> FEATURE:
<221> NAME/KEY: MOD_RES
<222> LOCATION: (14)
<223> OTHER INFORMATION: Ala, Leu, Ile pentylglycine, Val, or Met
<220> FEATURE:
<221> NAME/KEY: MOD_RES
<222> LOCATION: (15)
<223> OTHER INFORMATION: Ala or Glu
<220> FEATURE:
<221> NAME/KEY: MOD_RES
<222> LOCATION: (16)
<223> OTHER INFORMATION: Ala or Glu
<220> FEATURE:
<221> NAME/KEY: MOD_RES
<222> LOCATION: (17)
<223> OTHER INFORMATION: Ala or Glu
<220> FEATURE:
<221> NAME/KEY: MOD_RES
<222> LOCATION: (19)
<223> OTHER INFORMATION: Ala or Val
<220> FEATURE:
<221> NAME/KEY: MOD_RES
```

```
<222> LOCATION: (20)
<223> OTHER INFORMATION: Ala or Arg
<220> FEATURE:
<221> NAME/KEY: MOD_RES
<222> LOCATION: (21)
<223> OTHER INFORMATION: Ala or Leu
<220> FEATURE:
<221> NAME/KEY: MOD_RES
<222> LOCATION: (22)
<223> OTHER INFORMATION: Phe, Tyr, or naphthylalanine
<220> FEATURE:
<221> NAME/KEY: MOD_RES
<222> LOCATION: (23)
<223> OTHER INFORMATION: Ile, Val, Leu, pentylglycine,
      tert-butylglycine, or Met
<220> FEATURE:
<221> NAME/KEY: MOD_RES
<222> LOCATION: (24)
<223> OTHER INFORMATION: Ala, Glu, or Asp
<220> FEATURE:
<221> NAME/KEY: MOD_RES
<222> LOCATION: (25)
<223> OTHER INFORMATION: Ala, Trp, Phe, Tyr, or naphthylalanine
<220> FEATURE:
<221> NAME/KEY: MOD_RES
<222> LOCATION: (26)
<223> OTHER INFORMATION: Ala or Leu
<220> FEATURE:
<221> NAME/KEY: MOD_RES
<222> LOCATION: (27)
<223> OTHER INFORMATION: Ala or Lys
<220> FEATURE:
<221> NAME/KEY: MOD_RES
<222> LOCATION: (28)
<223> OTHER INFORMATION: Ala or Asn
<220> FEATURE:
<221> NAME/KEY: MOD_RES
<222> LOCATION: (29)
<223> OTHER INFORMATION: Gly or not present
<220> FEATURE:
<221> NAME/KEY: MOD_RES
<222> LOCATION: (30)
<223> OTHER INFORMATION: Gly or not present
<220> FEATURE:
<221> NAME/KEY: MOD_RES
<222> LOCATION: (31)
<223> OTHER INFORMATION: Pro, homoproline, thioproline,
      or N-methylalanine, or not present
<220> FEATURE:
<221> NAME/KEY: MOD_RES
<222> LOCATION: (32)
<223> OTHER INFORMATION: Ser or not present
<220> FEATURE:
<221> NAME/KEY: MOD_RES
<222> LOCATION: (33)
<223> OTHER INFORMATION: Ser or not present
<220> FEATURE:
<221> NAME/KEY: MOD_RES
<222> LOCATION: (34)
<223> OTHER INFORMATION: Gly or not present
<220> FEATURE:
<221> NAME/KEY: MOD_RES
<222> LOCATION: (35)
<223> OTHER INFORMATION: Ala or not present
<220> FEATURE:
<221> NAME/KEY: MOD_RES
<222> LOCATION: (36)
<223> OTHER INFORMATION: Pro, homoproline, thioproline,
      or N-methylalanine, or not present
<220> FEATURE:
<221> NAME/KEY: MOD_RES
<222> LOCATION: (37)
<223> OTHER INFORMATION: Pro, homoproline, thioproline,
      or N-methylalanine, or not present
<220> FEATURE:
<221> NAME/KEY: MOD_RES
<222> LOCATION: (38)
<223> OTHER INFORMATION: Pro, homoproline, thioproline,
      or N-methylalanine, or not present
```

-continued

```
<220> FEATURE:
<223> OTHER INFORMATION: May be c-term amidated

<400> SEQUENCE: 87

Xaa Xaa Xaa Gly Xaa Xaa Xaa Xaa Xaa Xaa Xaa Xaa Xaa Xaa Xaa
 1               5                   10                  15

Xaa Ala Xaa Xaa Xaa Xaa Xaa Xaa Xaa Xaa Xaa Xaa Xaa Xaa
            20                  25                  30

Xaa Xaa Xaa Xaa Xaa Xaa
            35
```